(12) United States Patent
Kirkpatrick

(10) Patent No.: US 12,384,744 B2
(45) Date of Patent: Aug. 12, 2025

(54) ENZYME-CLEAVABLE METHADONE PRODRUGS AND METHODS OF USE THEREOF

(71) Applicant: Ensysce Biosciences Inc., La Jolla, CA (US)

(72) Inventor: Lynn Kirkpatrick, La Jolla, CA (US)

(73) Assignee: Ensysce Biosciences Inc., La Jolla, CA (US)

( * ) Notice: Subject to any disclaimer, the term of this patent is extended or adjusted under 35 U.S.C. 154(b) by 0 days.

(21) Appl. No.: 17/955,270

(22) Filed: Sep. 28, 2022

(65) Prior Publication Data

US 2023/0159441 A1 May 25, 2023

Related U.S. Application Data

(60) Provisional application No. 63/250,041, filed on Sep. 29, 2021.

(51) Int. Cl.
| | |
|---|---|
| *C07C 279/12* | (2006.01) |
| *A61K 45/06* | (2006.01) |
| *C07D 207/09* | (2006.01) |
| *C07D 207/50* | (2006.01) |
| *C07D 211/98* | (2006.01) |
| *C07D 265/30* | (2006.01) |

(52) U.S. Cl.
CPC ............ *C07C 279/12* (2013.01); *A61K 45/06* (2013.01); *C07D 207/09* (2013.01); *C07D 207/50* (2013.01); *C07D 211/98* (2013.01); *C07D 265/30* (2013.01)

(58) Field of Classification Search
CPC .. C07C 279/12; C07D 207/09; C07D 207/50; C07D 211/98; C07D 265/30; A61K 45/06
See application file for complete search history.

(56) References Cited

U.S. PATENT DOCUMENTS

| | | | |
|---|---|---|---|
| 3,842,064 A | 10/1974 | Greven | |
| 3,850,904 A | 11/1974 | Greven | |
| 3,853,836 A | 12/1974 | Greven | |
| 3,853,838 A | 12/1974 | Greven | |
| 3,875,137 A | 4/1975 | Jones et al. | |
| 4,104,371 A | 8/1978 | Greven et al. | |
| 4,297,346 A | 10/1981 | Rips et al. | |
| 4,454,338 A | 6/1984 | Fujii et al. | |
| 4,532,255 A | 7/1985 | Fujii et al. | |
| 5,109,118 A | 4/1992 | Mizushima et al. | |
| 5,217,987 A | 6/1993 | Berger | |
| 5,352,704 A | 10/1994 | Okuyama et al. | |
| 6,245,802 B1 | 6/2001 | Iyengar et al. | |
| 6,388,122 B1 | 5/2002 | Kido et al. | |
| 6,586,196 B1 | 7/2003 | Bronstein et al. | |
| 7,060,290 B1 | 6/2006 | Morimoto et al. | |
| 7,105,486 B2 | 9/2006 | Mickle et al. | |
| 7,189,414 B2 | 3/2007 | Rubinstein et al. | |
| 7,223,735 B2 | 5/2007 | Mickle et al. | |
| 7,655,630 B2 | 2/2010 | Mickle et al. | |
| 7,893,105 B2 | 2/2011 | Xiang et al. | |
| 8,163,701 B2 | 4/2012 | Jenkins et al. | |
| 8,217,005 B2 | 7/2012 | Jenkins et al. | |
| 8,497,237 B2 | 7/2013 | Jenkins et al. | |
| 8,569,228 B2 | 10/2013 | Jenkins et al. | |
| 8,614,346 B2 | 12/2013 | Jass et al. | |
| 8,685,916 B2 | 4/2014 | Jenkins et al. | |
| 8,802,681 B2 | 8/2014 | Jenkins et al. | |
| 8,921,418 B2 | 12/2014 | Jenkins et al. | |
| 8,962,547 B2 | 2/2015 | Jenkins et al. | |
| 9,023,860 B2 | 5/2015 | Jenkins et al. | |
| 9,040,032 B2 | 5/2015 | Jenkins et al. | |
| 9,095,627 B2 | 8/2015 | Jenkins et al. | |
| 9,139,612 B2 | 9/2015 | Jenkins et al. | |
| 2003/0035831 A1 | 2/2003 | Modi | |
| 2003/0180352 A1 | 9/2003 | Patel et al. | |
| 2004/0063628 A1 | 4/2004 | Piccariello et al. | |
| 2005/0054561 A1 | 3/2005 | Mickle et al. | |
| 2005/0080012 A1 | 4/2005 | Mickle et al. | |
| 2005/0176644 A1 | 8/2005 | Mickle et al. | |
| 2005/0176645 A1 | 8/2005 | Mickle et al. | |
| 2007/0042955 A1 | 2/2007 | Mickle et al. | |

(Continued)

FOREIGN PATENT DOCUMENTS

| | | |
|---|---|---|
| DE | 1041052 | 10/1958 |
| DE | 1493824 | 5/1969 |
| EP | 1782834 | 5/2007 |
| EP | 2433655 | 2/2008 |
| GB | 1425099 | 2/1976 |
| WO | WO 1997012903 | 4/1997 |
| WO | WO 2002043767 | 6/2002 |
| WO | WO 2004082620 | 9/2004 |

(Continued)

OTHER PUBLICATIONS

Jenkins, Husfeld et al. (390) Abuse-resistant opioid prodrugs that demonstrate oral overdose protection. The Journal of Pain vol. 13, Issue 4, Supplement, S73, Apr. 2012 (Year: 2012).*

(Continued)

*Primary Examiner* — Kortney L. Klinkel
*Assistant Examiner* — Richard Grant Peckham
(74) *Attorney, Agent, or Firm* — Khin K. Chin; Bozicevic, Field & Francis LLP

(57) ABSTRACT

The present disclosure provides methadone prodrugs, pharmaceutical compositions, and their methods of use, where the pharmaceutical compositions comprise a methadone prodrug that provides enzymatically-controlled release of methadone, and an optional enzyme inhibitor that interacts with the enzyme(s) that mediates the enzymatically-controlled release of methadone from the prodrug so as to attenuate enzymatic cleavage of the prodrug.

3 Claims, 13 Drawing Sheets

(56) References Cited

U.S. PATENT DOCUMENTS

| | | |
|---|---|---|
| 2007/0082929 A1 | 4/2007 | Gant et al. |
| 2007/0093420 A1 | 4/2007 | Yeomans et al. |
| 2007/0123468 A1 | 5/2007 | Jenkins et al. |
| 2007/0203055 A1 | 8/2007 | Mickle et al. |
| 2008/0139653 A1 | 6/2008 | Mickle et al. |
| 2009/0013768 A1 | 1/2009 | Pouteau et al. |
| 2009/0136980 A1 | 5/2009 | Bebbington et al. |
| 2009/0137618 A1 | 5/2009 | Jenkins et al. |
| 2009/0192093 A1 | 7/2009 | Mickle et al. |
| 2009/0209569 A1 | 8/2009 | Arnelle et al. |
| 2010/0022792 A1 | 1/2010 | Shen |
| 2010/0035826 A1 | 2/2010 | Jenkins et al. |
| 2010/0080797 A1 | 4/2010 | Yeomans et al. |
| 2010/0092562 A1 | 4/2010 | Hollenbeck et al. |
| 2010/0227921 A1 | 9/2010 | Franklin et al. |
| 2010/0267614 A1 | 10/2010 | Jenkins |
| 2010/0286186 A1 | 11/2010 | Franklin et al. |
| 2011/0262355 A1 | 10/2011 | Jenkins et al. |
| 2011/0262359 A1 | 10/2011 | Jenkins et al. |
| 2011/0262360 A1 | 10/2011 | Jenkins et al. |
| 2011/0281886 A1 | 11/2011 | Jenkins et al. |
| 2012/0178772 A1 | 7/2012 | Jenkins et al. |
| 2012/0178773 A1 | 7/2012 | Jenkins et al. |
| 2012/0230916 A1 | 9/2012 | Jenkins et al. |
| 2012/0270847 A1 | 10/2012 | Franklin et al. |
| 2013/0059914 A1 | 3/2013 | Jenkins et al. |
| 2013/0210700 A1 | 8/2013 | Jenkins et al. |
| 2013/0210701 A1 | 8/2013 | Jenkins et al. |
| 2013/0210854 A1 | 8/2013 | Jenkins et al. |
| 2014/0121152 A1 | 5/2014 | Jenkins et al. |
| 2014/0206597 A1 | 7/2014 | Jenkins et al. |
| 2015/0031635 A1 | 1/2015 | Jenkins et al. |
| 2020/0009064 A1 | 1/2020 | Wengner |

FOREIGN PATENT DOCUMENTS

| | | |
|---|---|---|
| WO | WO 2005032474 | 4/2005 |
| WO | WO 2005042772 | 5/2005 |
| WO | WO 2007022535 | 2/2007 |
| WO | WO 2007120864 | 10/2007 |
| WO | WO 2007140272 | 12/2007 |
| WO | WO 2008012046 | 1/2008 |
| WO | WO 2007120648 | 7/2008 |
| WO | WO 2008101187 | 8/2008 |
| WO | WO 2008101202 | 8/2008 |
| WO | WO 2009067703 | 5/2009 |
| WO | WO 2009080030 | 7/2009 |
| WO | WO 2009092073 | 7/2009 |
| WO | WO 2009136392 | 11/2009 |
| WO | WO 2010045599 | 4/2010 |
| WO | WO 2010100477 | 9/2010 |
| WO | WO 2010148305 | 12/2010 |
| WO | WO 2011031350 | 3/2011 |
| WO | WO 2011133346 | 4/2011 |
| WO | WO 2011133149 | 10/2011 |
| WO | WO 2011133178 | 10/2011 |

OTHER PUBLICATIONS

Zachariah Thomas, MD, and Eduardo Bruera, MD. Use of Methadone in a Highly Tolerant Patient Receiving Parenteral Hydromorphone. Journal of Pain and Symptom Management. vol. 10 No. 4 May 1995. 315-317. (Year: 1995).*

Duggan (Tetrahedron Letters Ro. 7, pp. 595-598.) (Year: 1979).*

Bak et al. (1999) "Acyloxyalkoxy-Based Cyclic Prodrugs of Opioid Peptides: Evaluation of the Chemical and Enzymatic Stability as Well as Their Transport Properties Across Caco-2 Cell Monolayers" *Pharm Res* 16(1):24-29.

Bernkop-Schnurch (1998) "The use of inhibitory agents to overcome the enzymatic barrier to perorally administered therapeutic peptides and proteins" *J Control Release* 50(1-2):1-16.

Bioavailability and Bioequivalence Studies for Orally Administered Drug Products—General Considerations, Guidance for Industry, Food and Drug Administration , published on Oct. 2000.

Birk et al. (1976) "Trypsin and chymotrypsin inhibitors from soybeans" *Methods in Enzymology* 45:700-707.

Camostat Mediate (http://www.scbt.com/datasheet-203867-camostat-mesylate.html (downloaded on Nov. 14, 2013).

Danziger and Dean; (1989) "Automated site-directed drug design: a general algorithm for knowledge acquisition about hydrogen-bonding regions at protein surfaces"; Proc R Soc Lond B Biol Sci. 236(1283); pp. 101-113.

Database Internet [Online]Apr. 5, 2005 (Apr. 5, 2005), XP002350634 retrieved from Internet accession No. http://onlineethics.org/reseth/helsinki.html.

Database Registry (2001) Abstract, Database accession No. 339089-42-8.

De Nardo et al. (1976) "Studies on chemical structure and sweet taste. Note XIII. L-Acylamidosuccinilic acid derivatives" *Farmaco, Ed. Sci* 31(12): 906-916.

De Nardo et al. (1977) "Studies on chemical structure and sweet taste. Note XIII. L-Acylamidosuccinilic acid derivatives" Database Caplus, Abstract, Database accession No. 1977:119365.

Definition of "ex vivo" from thefreedictionary.com, accessed Oct. 7, 2014.

Geratz et al. (1976) "Novel bis(benzamidine) compounds with an aromatic central link. Inhibitors of thrombin, pancreatic kallikrein, trypsin, and complement" *J. Med. Chem.* 19:634-639.

Göke et al. (1984) "Effect of a Specific Serine Protease Inhibitor on the Rat Pancreas: Systemic Administration of Camostate and Exocrine" *Digestion* 30:171-178.

Gomes et al. (2007) "Cyclization-activated prodrugs" *Molecules* 12:2484-2506.

Gotoh et al. (2005) "The advantages of the Ussing chamber in drug absorption studies" *Journal of Biomolecular Screening* 10(5):517-523.

Gottschalk, et al., (2001), "New Concepts inAcute Pain Therapy: Preemptive Analgesia", American Family Physician, 63(10):1979-1984.

Hansch et al. (1990) "Comprehensive Medicinal Chemistry, vol. 5 Biopharmaceutics" *Rational Design, Mechanistic Study And Therapeutic Application Of Chemical Compounds, Oxford, Pergamon Press* 5:251-278.

Hijikata-Okunomiya et al. (2000) "Selective Inhibition of Trypsin by (2R,4R)-4-Phenyl-1-[$N^\alpha$-(7-methoxy-2-naphthalenesulfonyl)-L-arginyl]-2-piperidinecarboxylic Acid" *J. Biochem.* 275:18995-18999.

Hyams (downloaded on Nov. 21, 2014 from URL: <http://www.pediatricweb.com/webpost/iframe/MedicalConditions_465.asp?tArticleId=94>).

Iwanowicz et al. (2002) "Retro-Binding Thrombin Active Site Inhibitors: Identification of an Orally Active Inhibitor of Thrombin Catalytic Activity" *Bioorganic and Medicinal Chemistry Letters* 12:3183-3186.

Katragadda et al. (2006) "Simultaneous Modulation of Transport and Metabolism of Acyclovir Prodrugs across Rabbit Cornea: An approach Involving Enzyme Inhibitors" *Int J Pharm* 320(1-2):104-113.

Kunze et al. (1983) "Effects of the serine protease inhibitors FOY and FOY 305 on phospholipase A I (EC 3.1.1.32) activity in rat-liver lysosomes" *Pharm. Research Com.* 15: 451-459.

Lapidus and Sweeney (1973) "L-4'-Cyano-3-(2.2.2-trifluoroacetamideo)s uccinanilic Acid and Related Synthetic Sweetening Agents" *J. Med. Chem.* 16(2):163-166.

Lin et al. (1993) "The 0.25-nm X-ray structure of the Bowman-Birk type inhibitor from mung bean in ternary complex with porcine trypsin" *Eur. J. Biochem.* 212:549-555.

Markwardt et al. (1968) "Comparative studies on the inhibition of trypsin, plasmin, and thrombin by derivatives of benzylamine and benzylamidine" *Eur. J. Biochem*, 6:502-506.

Nafamostat (PubChem, National Center for Biotechnology Information dated Dec. 20, 2005).

Nechab et al. (2008) "N-Acylglycinates as acyl donors in serine protease-catalyzed kinetic resolution of amines. Improvement of selectivity and reaction rates." *Org. Biol. Chem.* 6:3917-3920.

(56) References Cited

OTHER PUBLICATIONS

Opiois911 (downloaded on Nov. 21, 2014 from URL: <http://opioids911.org/safety.php>).
Ozawa et al. (1966) "The reactive site of trypsin inhibitors" *J. Biol. Chem.* 241:3955-3961.
Pain Doctor (downloaded on Nov. 21, 2014 from URL: <http://paindoctor.com/conditions/common/phantom-limb-pain/>).
Pauletti, Giovanni et al. (1997) "Esterase-Sensitive Cyclic Prodrugs of Peptides: Evaluation of a Phenylpropionic Acid Promoiety in a Model Hexapeptide" *Pharm Res* 14(1):11-17.
Perona et a l. (1995) "Structural basis of substrate specificity in the serine proteases"; Protein Science vol. 4; pp. 337-360.
Plummer et al. (1997) "Design of peptidomimetic ligands for the pp60srcSH2 domain" *Bioorganic and Medicinal Chemistry* 5(1):41-47.
Prater et al. (2002) "Successful Pain Management for the Recovering Addicted Patient" *Primary Care Companion J Clin Psychiatry* 4(4):125-131.
Ramjee et al. (2000) "The Kinetic and Structural Characterization of the Reaction of Nafamostat with Bovine Pancreatic Trypsin" *Thrmb Res.* 98(6):559-569.
Reddy et al. (2012) "An improved process for the preparation of lisdexamfetamine and its pharmaceutically acceptable salts" Database Caplus, Abstract, Database accession No. 2012:654913.
Renatus et al. (1998) "Structural and Functional Analyses of Benzamidine-Based Inhibitors in Complex with Trypsin: Implications for the Inhibition of Factor Xa, tPA, and Urokinase" *J. Med. Chem.* 41(27):5445-5456.
Schanker et al. (1958) "Absorption of drugs from the rat small intestine" *Journal of Pharmacology and Experimental Therapeutics* 123(1):81-88.
Senoo et al. (1966) "Glutamic acid amides" Database Caplus, Abstract, Database accession No. 1966:19804.
Simone Joseph; "Oncology (Introduction)" Textbook of Medicine, 20(1), pp. 1004-1010 (Year: 1997).
Song, Xiaoping et al. (2002) "Synthesis of a Novel Cyclic Prodrug of RGD Peptidomimetic to Improve Its Cell Membrane Permeation" *Bioorg Chem* 30(4):285-301.
Tanizawa et al. (1987) "Inverse Substrates for Tryspin and Tryspin-like Enzymes" *Acc. Chem. Res.* 20:337-343.
Testa et al. (2003) "Hydrolysis in Drug and Prodrug Metabolism" Verlag Helvetica Chimica Acta, Postfach, CH-8042, Switzerland, pp. 420-534.
Tirkkonen et al. (2004) "Drug interactions with the potential to prevent prodrug activation as a common source of irrational prescribing in hospital inpatients" *Clinical Pharmacology and Therapeutics* 76(6):639-647.
Umezawa (1976) "Structure and activities of protease inhibitors of microbial origin" *Methods in Enzymology* 45:678-695.
Van Gelder et al. (2002) "Intestinal absorption enhancement of the ester prodrug tenofovir disoproxil fumarate through modulation of the biochemical barrier by defined ester mixtures" *Drug Metabolism and Disposition* 30(8):924-930.

\* cited by examiner

ENZYME-CLEAVABLE METHADONE PRODRUGS AND METHODS OF USE THEREOF

CROSS-REFERENCE TO RELATED APPLICATIONS

Pursuant to 35 U.S.C. § 119(e), this application claims priority to the filing date of U.S. Provisional Patent Application Ser. No. 63/250,041 filed Sep. 29, 2021; the disclosure of which application is incorporated herein by reference in their entirety.

INTRODUCTION

Methadone is a synthetic opioid agonist that is often used for opioid maintenance therapy in opioid dependence and for chronic pain management. Opioids like methadone are susceptible to misuse, abuse, or overdose. Use of and access to methadone often needs to be controlled. The control of access to methadone is expensive to administer and can result in denial of treatment for patients that are not able to present themselves for dosing. For example, patients suffering from acute pain may be denied treatment with a pain drug unless they have been admitted to a hospital. Furthermore, control of use is often ineffective, leading to substantial morbidity and deleterious social consequences.

SUMMARY

The present disclosure provides pharmaceutical compositions, and their methods of use, where the pharmaceutical compositions comprise a methadone prodrug that provides enzymatically-controlled release of methadone, and an optional enzyme inhibitor that interacts with the enzyme(s) that mediates the enzymatically-controlled release of methadone from the prodrug so as to attenuate enzymatic cleavage of the prodrug.

The present disclosure also provides a composition, such as a pharmaceutical composition, that comprises a methadone prodrug of the embodiments. Such a composition can optionally provide an inhibitor that interacts with the enzyme that mediates the controlled release of methadone from the prodrug so as to attenuate enzymatic cleavage of the methadone prodrug. The disclosure provides for the enzyme being a gastrointestinal (GI) enzyme, such as trypsin. Also provided are methods of use, such as a method of providing patients with controlled release of methadone using a methadone prodrug of the embodiments. Aspects further include a controlled release composition of nafamostat or pharmaceutically acceptable salt thereof where nafamostat or pharmaceutically acceptable salt mediates enzymatically-controlled release of methadone from the methadone prodrug following oral ingestion of the composition. Such cleavage can initiate, contribute to or effect drug release.

The embodiments include a methadone prodrug that is a compound of formula MD-(I):

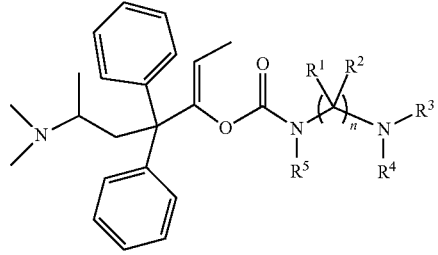

(MD-(I))

wherein:

$R^5$ is selected from hydrogen, alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 2 to 4;

$R^3$ is hydrogen, alkyl, substituted alkyl, arylalkyl, substituted arylalkyl, aryl and substituted aryl;

$R^4$ is

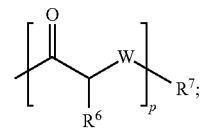

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include a methadone prodrug that is a compound of formula MD-(II):

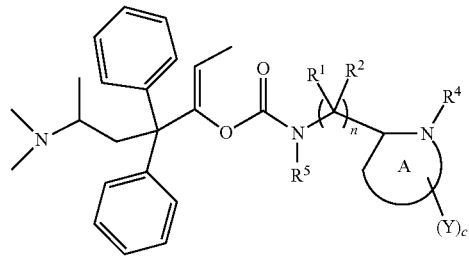

(MD-(II))

wherein:
R⁵ is selected from hydrogen, alkyl, substituted alkyl, arylalkyl, substituted arylalkyl, aryl and substituted aryl;
each R¹ is independently selected from hydrogen, alkyl, substituted alkyl, aryl, substituted aryl, acyl, and aminoacyl;
each R² is independently selected from hydrogen, alkyl, substituted alkyl, aryl, substituted aryl, acyl, and aminoacyl;
or R¹ and R² together with the carbon to which they are attached form a cycloalkyl, substituted cycloalkyl, aryl, or substituted aryl group, or two R² or R³ groups on adjacent carbon atoms, together with the carbon atoms to which they are attached, form a cycloalkyl, substituted cycloalkyl, aryl, or substituted aryl group;
n is an integer from 1 to 4;
the A ring is a heterocyclic 5 to 12-membered ring;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
R⁴ is

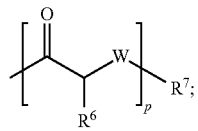

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R⁶ and R⁷ together with the atoms to which they are bonded form a cycloheteroalkyl or substituted cycloheteroalkyl ring;
each W is independently —NR⁸—, —O— or —S—;
each R⁸ is independently selected from hydrogen, alkyl, substituted alkyl, aryl and substituted aryl, or optionally, each R⁶ and R⁸ independently together with the atoms to which they are bonded form a cycloheteroalkyl or substituted cycloheteroalkyl ring;
p is an integer from one to 100; and
R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

In certain embodiments, the methadone prodrug is a compound of formulate MD-(IIa):

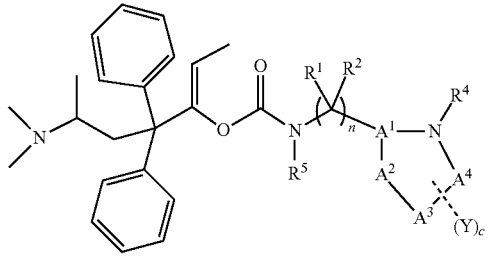

(MD-(IIa))

wherein:
R⁵ is selected from hydrogen, alkyl, substituted alkyl, arylalkyl, substituted arylalkyl, aryl and substituted aryl;
each R¹ is independently selected from hydrogen, alkyl, substituted alkyl, aryl, substituted aryl, acyl, and aminoacyl;
each R² is independently selected from hydrogen, alkyl, substituted alkyl, aryl, substituted aryl, acyl, and aminoacyl;
or R¹ and R² together with the carbon to which they are attached form a cycloalkyl, substituted cycloalkyl, aryl, or substituted aryl group, or two R² or R³ groups on adjacent carbon atoms, together with the carbon atoms to which they are attached, form a cycloalkyl, substituted cycloalkyl, aryl, or substituted aryl group;
n is an integer from 1 to 4;
A¹, A², A³, and A⁴ are independently selected from carbon, nitrogen, oxygen, and sulfur;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
R⁴ is

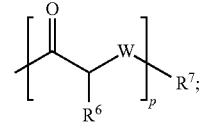

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R⁶ and R⁷ together with the atoms to which they are bonded form a cycloheteroalkyl or substituted cycloheteroalkyl ring;
each W is independently —NR⁸—, —O— or —S—;
each R⁸ is independently selected from hydrogen, alkyl, substituted alkyl, aryl and substituted aryl, or optionally, each R⁶ and R⁸ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IIb):

(MD-(IIb))

wherein:

R$^5$ is selected from hydrogen, alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n is an integer from 1 to 4;

A$^1$, A$^2$, A$^3$, A$^4$ and A$^5$ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

R$^4$ is each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include a methadone prodrug that is a compound of formula MD-(III):

(MD-(III))

wherein:

R$^5$ is selected from hydrogen, alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n is an integer from 1 to 4;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

R$^4$ is each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IIIa):

(MD-(IIIa))

[Chemical structure]

wherein:

R$^5$ is selected from hydrogen, alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n is an integer from 1 to 4;

A$^1$, A$^2$, A$^3$, and A$^4$ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

R$^4$ is

[Chemical structure]

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IIIb):

(MD-IIIb))

[Chemical structure]

wherein:

R$^5$ is selected from hydrogen, alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n is an integer from 1 to 4;

A$^1$, A$^2$, A$^3$, A$^4$ and A$^5$ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

R$^4$ is

[Chemical structure]

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include a methadone prodrug that is a compound of formula MD-(IV):

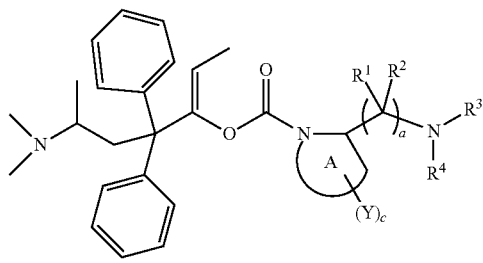

(MD-(IV))

wherein:

$R^3$ is selected from hydrogen, alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 1 to 4;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3; $R^4$ is

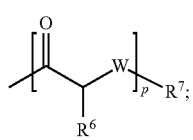

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IVa):

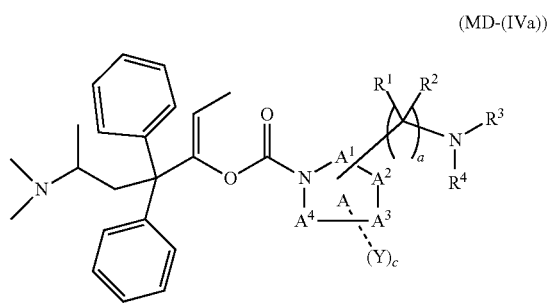

(MD-(IVa))

wherein:

$R^3$ is selected from hydrogen, alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 1 to 4;

$A^1, A^2, A^3$ and $A^4$ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
$R^4$ is

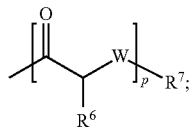

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;
each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;
p is an integer from one to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

In certain embodiments, the methadone prodrug is a compound of formulate MD-(IVb):

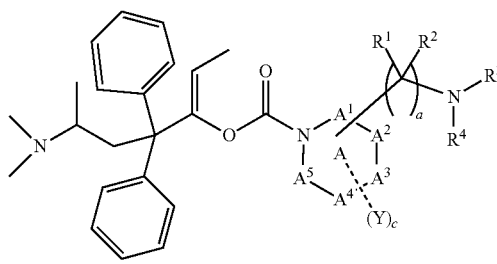

(MD-IVb))

wherein:
$R^3$ is selected from hydrogen, alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
n is an integer from 1 to 4;
$A^1$, $A^2$, $A^3$, $A^4$ and $A^5$ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
$R^4$ is

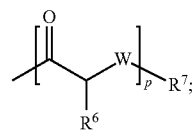

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;
each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;
p is an integer from one to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

The embodiments include a methadone prodrug that is a compound of formula MD-(IV):

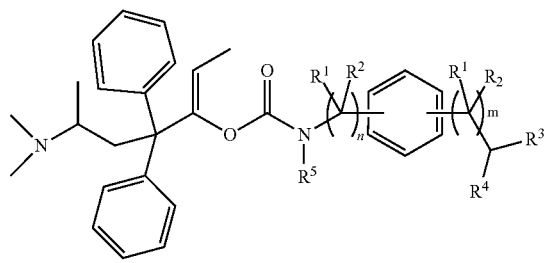

(MD-(V))

wherein:
$R^5$ is selected from hydrogen, alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
n is an integer from 0 to 4;
m is an integer from 0 to 4;
the A ring is a heterocyclic 5 to 12-membered ring;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
$R^4$ is

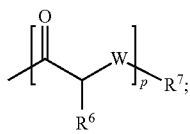

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;
each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;
p is an integer from one to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

The present disclosure also provides pharmaceutical compositions, and their methods of use, where the pharmaceutical compositions comprise a methadone prodrug that provides controlled release of methadone via enzyme cleavage (e.g., followed by intramolecular cyclization). Such compositions can optionally provide an inhibitor, such as a trypsin inhibitor, that interacts with the enzyme that mediates the controlled release of methadone from the prodrug so as to attenuate enzymatic cleavage of the methadone prodrug. The disclosure provides for the enzyme being a gastrointestinal (GI) enzyme, such as trypsin.

Aspects of the present disclosure also include oral compositions of nafamostat or a pharmaceutically acceptable salt thereof where the composition provides for controlled release of the nafamostat or pharmaceutically acceptable salt thereof to a subject for an extended period of time. In some embodiments, the oral composition of nafamostat or a pharmaceutically acceptable salt thereof includes a plurality of controlled release beads where each bead includes a core, an active agent layer having nafamostat or a pharmaceutically acceptable salt thereof and a controlled release layer having one or more polymers formulated in an amount sufficient to provide for controlled release of the nafamostat or pharmaceutically acceptable salt thereof. In some embodiments, the plurality of controlled release nafamostat beads are encapsulated in a capsule. In certain embodiments, the capsule further includes one or more of the methadone prodrugs as described above.

Aspects of the present disclosure also include methods for orally administering to a subject in need thereof a methadone prodrug and one or more of the controlled release nafamostat compositions described herein. In some instances, the methadone prodrug is administered simultaneously with the controlled release nafamostat composition. In other instances, the methadone prodrug and the controlled release nafamostat composition are administered sequentially. In some cases, the controlled release nafamostat composition is orally administered to the subject a predetermined period of time before administering the methadone prodrug. In some cases, the controlled release nafamostat composition is orally administered to the subject a predetermined period of time after administering the methadone prodrug.

The embodiments of the present disclosure provide for improved patient compliance with a therapy prescribed by a clinician comprising directing administration of any of the compositions or dose units described herein to a patient in need thereof. Such embodiments can provide for improved patient compliance with a prescribed therapy as compared to patient compliance with a prescribed therapy using drug and/or using prodrug without the controlled release nafamostat or pharmaceutically acceptable salt thereof as compared to prodrug with the controlled release nafamostat or pharmaceutically acceptable salt thereof. The embodiments also provide for reduced risk of unintended overdose of methadone comprising directing administration of any of the pharmaceutical compositions or dose units described herein to a patient in need of treatment.

The embodiments also include methods of making a dose unit comprising combining a methadone prodrug and a controlled release nafamostat composition in a dose unit, wherein the methadone prodrug and controlled release nafamostat composition are present in the dose unit in an amount effective to attenuate release of methadone from the prodrug.

DEFINITIONS

Figure 1:
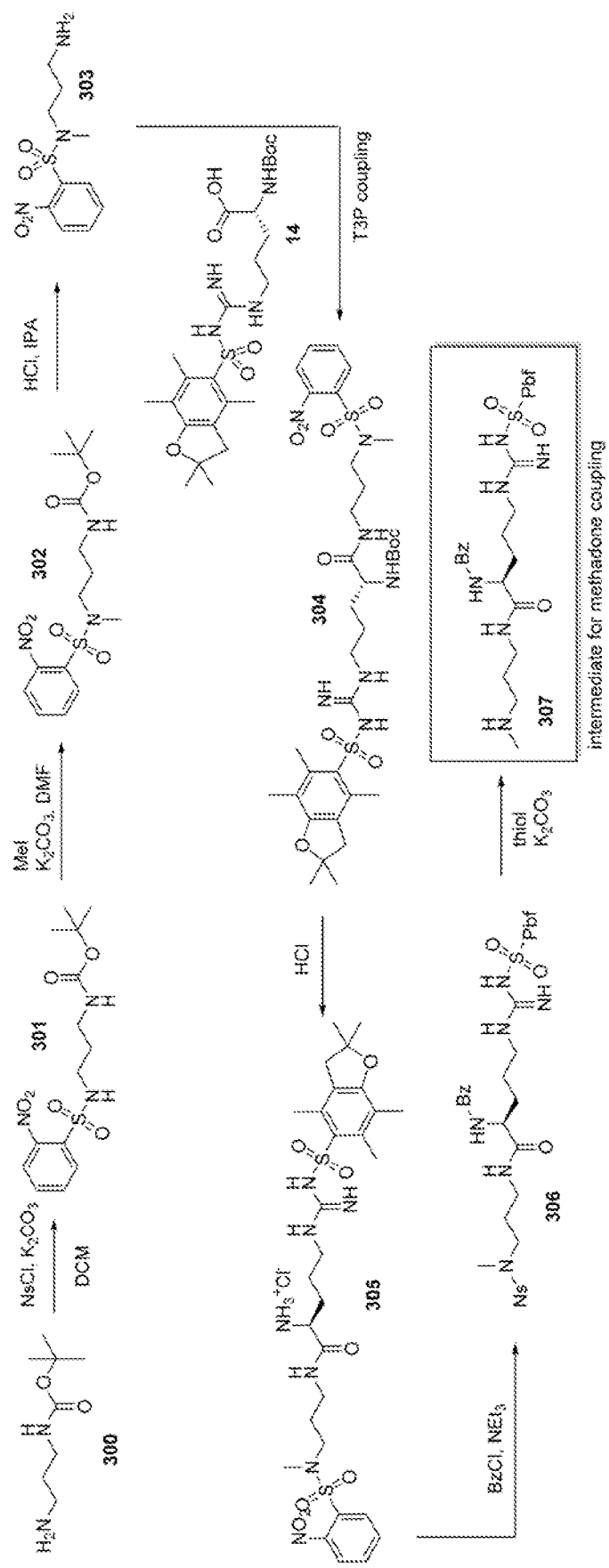
FIG. 1 depicts an example synthetic scheme of an intermediate for methadone prodrug according to certain embodiments.

The following terms have the following meaning unless otherwise indicated. Any undefined terms have their art recognized meanings.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene ($-CH_2-$), ethylene ($-CH_2CH_2-$), the propylene isomers (e.g., $-CH_2CH_2CH_2-$ and $-CH(CH_3)CH_2-$) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical $-C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, propionyl, succinyl, and malonyl, and the like.

The term "aminoacyl" refers to the group $-C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical $-OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical $-C(O)OR^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp³ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —O—, =O, —$OR^{60}$, —$SR^{60}$, —S, =S, —$NR^{60}R^{61}$, =$NR^{60}$, —$CF_3$, —CN, —OCN, —SCN, —NO, —$NO_2$, =$N_2$, —$N_3$, —$S(O)_2O$—, —$S(O)_2OH$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, —$OR^{60}$, —$SR^{60}$, —S—, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

"Dose unit" as used herein refers to a combination of a GI enzyme-cleavable prodrug (e.g., trypsin-cleavable prodrug) and a GI enzyme inhibitor (e.g., a trypsin inhibitor). A "single dose unit" is a single unit of a combination of a GI enzyme-cleavable prodrug (e.g., trypsin-cleavable prodrug) and a GI enzyme inhibitor (e.g., trypsin inhibitor), where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"Pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax) and side effects.

"Gastrointestinal enzyme" or "GI enzyme" refers to an enzyme located in the gastrointestinal (GI) tract, which encompasses the anatomical sites from mouth to anus. Trypsin is an example of a GI enzyme.

"Gastrointestinal enzyme-cleavable moiety" or "GI enzyme-cleavable moiety" refers to a group comprising a site susceptible to cleavage by a GI enzyme. For example, a "trypsin-cleavable moiety" refers to a group comprising a site susceptible to cleavage by trypsin.

"Gastrointestinal enzyme inhibitor" or "GI enzyme inhibitor" refers to any agent capable of inhibiting the action of a gastrointestinal enzyme on a substrate. The term also encompasses salts of gastrointestinal enzyme inhibitors. For example, a "trypsin inhibitor" refers to any agent capable of inhibiting the action of trypsin on a substrate.

"Pharmaceutical composition" refers to at least one compound and can further comprise a pharmaceutically acceptable carrier, with which the compound is administered to a patient.

"Pharmaceutically acceptable carrier" refers to a diluent, adjuvant, excipient or vehicle with, or in which a compound is administered.

"Preventing" or "prevention" or "prophylaxis" refers to a reduction in risk of occurrence of a condition, such as pain.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Treating" or "treatment" of any condition, such as pain, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound (e.g. prodrug) that, when administered to a patient for preventing or treating a condition such as pain, is sufficient to effect such treatment. The "therapeutically effective amount" will vary depending on the compound, the condition and its severity and the age, weight, etc., of the patient.

DETAILED DESCRIPTION

Aspects of the present disclosure include methadone prodrugs, pharmaceutical compositions, and their methods of use, where the pharmaceutical compositions comprise a methadone prodrug that provides enzymatically-controlled release of methadone, and an optional enzyme inhibitor that interacts with the enzyme(s) that mediates the enzymatically-controlled release of methadone from the prodrug so as to attenuate enzymatic cleavage of the prodrug.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As used herein, the singular forms "a", "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of," "consists essentially of," "consisting," and "consists" can be used interchangeably.

The term "about" or "approximately" means within an acceptable error range for the particular value as determined by one of ordinary skill in the art, which will depend in part on how the value is measured or determined, i.e., the limitations of the measurement system. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Methadone Prodrugs

As summarized above, aspects of the present disclosure include methadone prodrugs that provide enzymatically-controlled release of methadone.

Representative Embodiments

Reference will now be made in detail to various embodiments. It will be understood that the invention is not limited to these embodiments. To the contrary, it is intended to cover alternatives, modifications, and equivalents as may be included within the spirit and scope of the allowed claims.

The present disclosure provides pharmaceutical compositions, and their methods of use, where the pharmaceutical compositions comprise a methadone prodrug that provides enzymatically-controlled release of methadone and an optional enzyme inhibitor that interacts with the enzyme(s) that mediates the enzymatically-controlled release of methadone from the prodrug so as to attenuate enzymatic cleavage of the prodrug. The disclosure provides pharmaceutical compositions which comprise an optional trypsin inhibitor and a methadone prodrug that contains a trypsin-cleavable moiety that, when cleaved, facilitates release of methadone.

According to one aspect, the embodiments include pharmaceutical compositions, which comprise a trypsin-cleavable methadone prodrug and an optional trypsin inhibitor. Examples of methadone prodrugs and trypsin inhibitors are described below. The disclosure provides for a methadone prodrug in which the promoiety comprises a cyclizable spacer leaving group and a cleavable moiety. In certain embodiments, the methadone prodrug is a corresponding compound in which the enolic hydrogen atom has been substituted with a spacer leaving group bearing a nitrogen nucleophile that is protected with an enzymatically-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide methadone.

The enzyme capable of cleaving the enzymatically-cleavable moiety may be a peptidase, also referred to as a protease—the promoiety comprising the enzymatically-cleavable moiety being linked to the nucleophilic nitrogen through an amide (e.g. a peptide: —NHC(O)—) bond. In some embodiments, the enzyme is a digestive enzyme of a protein.

The corresponding prodrug provides post administration-activated, controlled release of methadone. The prodrug requires enzymatic cleavage to initiate release of methadone and thus the rate of release of methadone depends upon both the rate of enzymatic cleavage and the rate of cyclization.

Accordingly, the methadone prodrug has reduced susceptibility to accidental methadone overdosing or abuse, whether by deliberate overdosing, administration through an inappropriate route, such as by injection, or by chemical modification using readily available household chemicals. The prodrug is configured so that it will not provide excessively high plasma levels of methadone if it is administered inappropriately, and cannot readily be decomposed to afford active methadone other than by enzymatic cleavage (e.g., followed by controlled cyclization).

The enzyme-cleavable moiety linked to the nitrogen nucleophile through an amide bond can be, for example, a residue of an amino acid or a peptide, or an (alpha)N-acyl derivative of an amino acid or peptide (for example an N-acyl derivative of a pharmaceutically acceptable carboxylic acid). The peptide can contain, for example, up to about 100 amino acid residues. Each amino acid can advantageously be a naturally occurring amino acid, such as an L-amino acid. Examples of naturally occurring amino acids are alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. Accordingly, examples of enzyme-cleavable moieties include residues of the L-amino acids listed hereinabove and N-acyl derivatives thereof, and peptides formed from at least two of the L-amino acids listed hereinabove, and the N-acyl derivatives thereof.

The cyclic group formed when methadone is released is conveniently pharmaceutically acceptable, for example a pharmaceutically acceptable cyclic urea. It will be appreciated that cyclic ureas are generally very stable and have low toxicity.

In embodiments, "salts" of the compounds of the present disclosure may include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In some embodiments, salts of interest include sodium salts.

The term "solvate" as used herein refers to a complex or aggregate formed by one or more molecules of a solute, e.g. a compound of Formula MD-(I) or a salt thereof, and one or more molecules of a solvent. Such solvates may be crystalline solids having a substantially fixed molar ratio of solute and solvent. Representative solvents include by way of example, water, methanol, ethanol, isopropanol, acetic acid, and the like. When the solvent is water, the solvate formed is a hydrate.

The embodiments include a methadone prodrug that is a compound of formula MD-(I):

(MD-(I))

wherein:
$R^5$ is selected from hydrogen, alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
n is an integer from 2 to 4;
$R^3$ is hydrogen, alkyl, substituted alkyl, arylalkyl, substituted arylalkyl, aryl and substituted aryl;
$R^4$ is each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;
each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and
$R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;
or a salt, hydrate or solvate thereof.

The embodiments include a methadone prodrug that is a compound of formula MD-(II):

(MD-(II))

wherein:
$R^5$ is selected from hydrogen, alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
n is an integer from 1 to 4;
the A ring is a heterocyclic 5 to 12-membered ring;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
$R^4$ is each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;
each W is independently —$NR^8$—, —O— or —S—;
each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IIa):

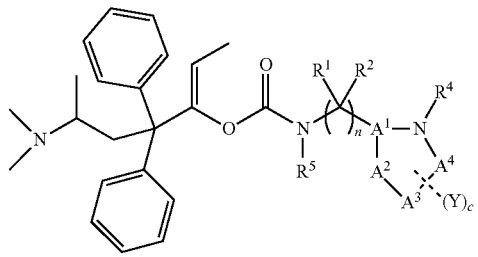

(MD-(IIa))

wherein:
$R^5$ is selected from hydrogen, alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
n is an integer from 1 to 4;
$A^1$, $A^2$, $A^3$, and $A^4$ are independently selected from carbon, nitrogen, oxygen, and sulfur; each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
$R^4$ is

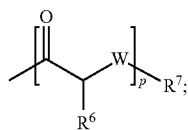

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl; or a salt, hydrate or solvate thereof.

In certain embodiments, the methadone prodrug is a compound of formulate MD-(IIb):

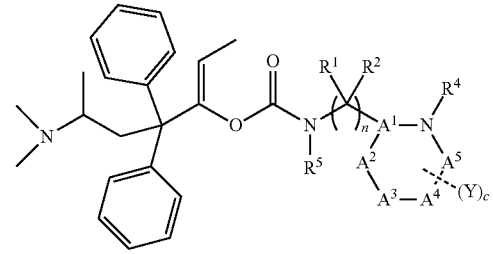

(MD-(IIb))

wherein:
$R^5$ is selected from hydrogen, alkyl, substituted alkyl, arylalkyl, substituted arylalkyl, aryl and substituted aryl;
each $R^1$ is independently selected from hydrogen, alkyl, substituted alkyl, aryl, substituted aryl, acyl, and aminoacyl;
each $R^2$ is independently selected from hydrogen, alkyl, substituted alkyl, aryl, substituted aryl, acyl, and aminoacyl;
or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;
n is an integer from 1 to 4;
$A^1$, $A^2$, $A^3$, $A^4$ and $A^5$ are independently selected from carbon, nitrogen, oxygen, and sulfur;
each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;
c is a number from zero to 3;
$R^4$ is

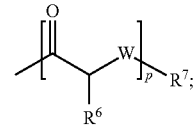

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include a methadone prodrug that is a compound of formula MD-(III):

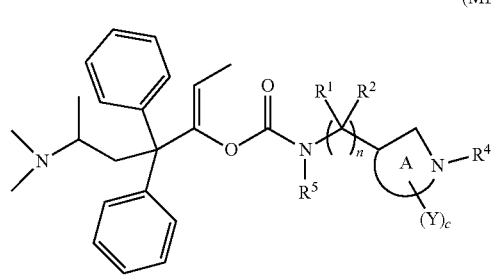

(MD-(III))

wherein:

R$^5$ is selected from hydrogen, alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n is an integer from 1 to 4;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

R$^4$ is

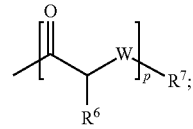

each R$^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R$^6$ and R$^7$ together with the atoms to which they are bonded form a cycloheteroalkyl or substituted cycloheteroalkyl ring;

each W is independently —NR$^8$—, —O— or —S—;

each R$^8$ is independently selected from hydrogen, alkyl, substituted alkyl, aryl and substituted aryl, or optionally, each R$^6$ and R$^8$ independently together with the atoms to which they are bonded form a cycloheteroalkyl or substituted cycloheteroalkyl ring;

p is an integer from one to 100; and

R$^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IIIa):

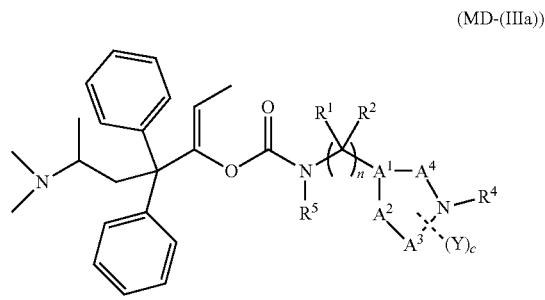

(MD-(IIIa))

wherein:

R$^5$ is selected from hydrogen, alkyl, substituted alkyl, arylalkyl, substituted arylalkyl, aryl and substituted aryl;

each R$^1$ is independently selected from hydrogen, alkyl, substituted alkyl, aryl, substituted aryl, acyl, and aminoacyl;

each R$^2$ is independently selected from hydrogen, alkyl, substituted alkyl, aryl, substituted aryl, acyl, and aminoacyl;

or R$^1$ and R$^2$ together with the carbon to which they are attached form a cycloalkyl, substituted cycloalkyl, aryl, or substituted aryl group, or two R$^2$ or R$^3$ groups on adjacent carbon atoms, together with the carbon atoms to which they are attached, form a cycloalkyl, substituted cycloalkyl, aryl, or substituted aryl group;

n is an integer from 1 to 4;

A$^1$, A$^2$, A$^3$, and A$^4$ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

$R^4$ is

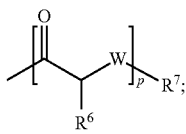

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IIIb):

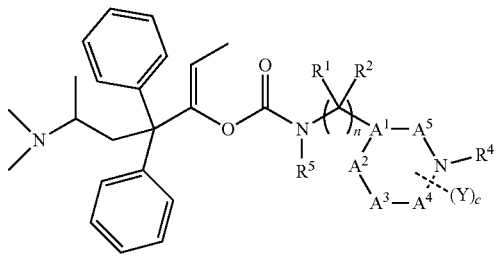

(MD-(IIIb))

wherein:

$R^5$ is selected from hydrogen, alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 1 to 4;

$A^1$, $A^2$, $A^3$, $A^4$ and $A^5$ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

$R^4$ is

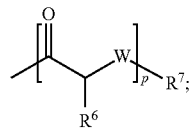

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include a methadone prodrug that is a compound of formula MD-(IV):

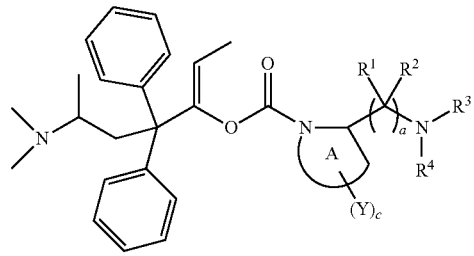

(MD-(IV))

wherein:

$R^3$ is selected from hydrogen, alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or R¹ and R² together with the carbon to which they are attached form a cycloalkyl, substituted cycloalkyl, aryl, or substituted aryl group, or two R² or R³ groups on adjacent carbon atoms, together with the carbon atoms to which they are attached, form a cycloalkyl, substituted cycloalkyl, aryl, or substituted aryl group;

n is an integer from 1 to 4;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

R⁴ is

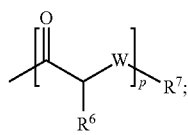

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R⁶ and R⁷ together with the atoms to which they are bonded form a cycloheteroalkyl or substituted cycloheteroalkyl ring;

each W is independently —NR⁸—, —O— or —S—;

each R⁸ is independently selected from hydrogen, alkyl, substituted alkyl, aryl and substituted aryl, or optionally, each R⁶ and R⁸ independently together with the atoms to which they are bonded form a cycloheteroalkyl or substituted cycloheteroalkyl ring;

p is an integer from one to 100; and

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IVa):

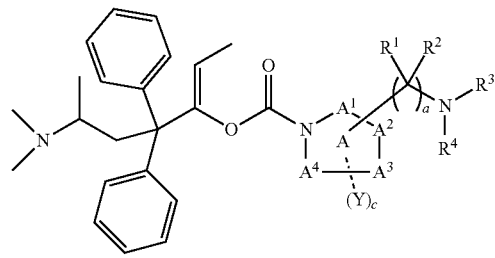

(MD-(IVa))

wherein:

R³ is selected from hydrogen, alkyl, substituted alkyl, arylalkyl, substituted arylalkyl, aryl and substituted aryl;

each R¹ is independently selected from hydrogen, alkyl, substituted alkyl, aryl, substituted aryl, acyl, and aminoacyl;

each R² is independently selected from hydrogen, alkyl, substituted alkyl, aryl, substituted aryl, acyl, and aminoacyl;

or R¹ and R² together with the carbon to which they are attached form a cycloalkyl, substituted cycloalkyl, aryl, or substituted aryl group, or two R² or R³ groups on adjacent carbon atoms, together with the carbon atoms to which they are attached, form a cycloalkyl, substituted cycloalkyl, aryl, or substituted aryl group;

n is an integer from 1 to 4;

A¹, A², A³ and A⁴ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

R⁴ is

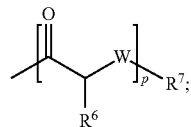

each R⁶ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R⁶ and IV together with the atoms to which they are bonded form a cycloheteroalkyl or substituted cycloheteroalkyl ring;

each W is independently —NR⁸—, —O— or —S—;

each R⁸ is independently selected from hydrogen, alkyl, substituted alkyl, aryl and substituted aryl, or optionally, each R⁶ and R⁸ independently together with the atoms to which they are bonded form a cycloheteroalkyl or substituted cycloheteroalkyl ring;

p is an integer from one to 100; and

R⁷ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In certain embodiments, the methadone prodrug is a compound of formulate MD-(IVb):

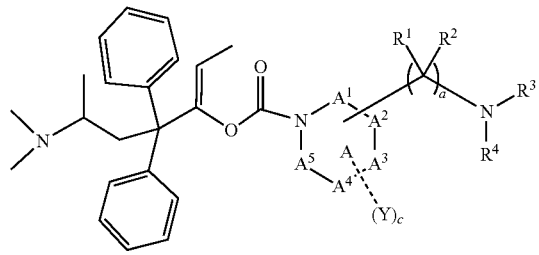

(MD-(IVb))

wherein:

R³ is selected from hydrogen, alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 1 to 4;

$A^1$, $A^2$, $A^3$, $A^4$ and $A^5$ are independently selected from carbon, nitrogen, oxygen, and sulfur;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

$R^4$ is

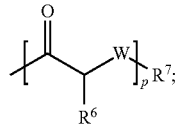

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

The embodiments include a methadone prodrug that is a compound of formula MD-(IV):

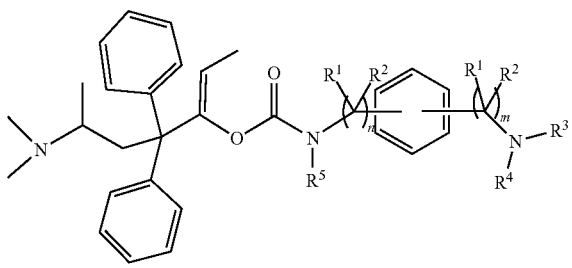

(MD-(V))

wherein:

$R^5$ is selected from hydrogen, alkyl, substituted alkyl, arylalkyl, substituted arylalkyl, aryl and substituted aryl;

each $R^1$ is independently selected from hydrogen, alkyl, substituted alkyl, aryl, substituted aryl, acyl, and aminoacyl;

each $R^2$ is independently selected from hydrogen, alkyl, substituted alkyl, aryl, substituted aryl, acyl, and aminoacyl;

or $R^1$ and $R^2$ together with the carbon to which they are attached form a cycloalkyl, substituted cycloalkyl, aryl, or substituted aryl group, or two $R^2$ or $R^3$ groups on adjacent carbon atoms, together with the carbon atoms to which they are attached, form a cycloalkyl, substituted cycloalkyl, aryl, or substituted aryl group;

n is an integer from 0 to 4;

m is an integer from 0 to 4;

the A ring is a heterocyclic 5 to 12-membered ring;

each Y is independently selected from alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

c is a number from zero to 3;

$R^4$ is

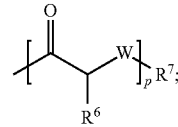

each $R^6$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and $R^7$ together with the atoms to which they are bonded form a cycloheteroalkyl or substituted cycloheteroalkyl ring;

each W is independently —$NR^8$—, —O— or —S—;

each $R^8$ is independently selected from hydrogen, alkyl, substituted alkyl, aryl and substituted aryl, or optionally, each $R^6$ and $R^8$ independently together with the atoms to which they are bonded form a cycloheteroalkyl or substituted cycloheteroalkyl ring;

p is an integer from one to 100; and $R^7$ is selected from hydrogen, alkyl, substituted alkyl, acyl, substituted acyl, alkoxycarbonyl, substituted alkoxycarbonyl, aryl, substituted aryl, arylalkyl, and substituted arylalkyl;

or a salt, hydrate or solvate thereof.

In some instances, $R^3$ can be selected from hydrogen, alkyl, substituted alkyl, arylalkyl, substituted arylalkyl, aryl and substituted aryl. In certain instances, $R^3$ is hydrogen. In certain instances, $R^3$ is (1-6C)alkyl. In other instances, $R^3$ is (1-4C)alkyl. In some instances, $R^3$ is selected from methyl, ethyl, n-propyl, isopropyl, n-butyl, t-butyl, pentyl and hexyl. In other instances, $R^3$ is methyl or ethyl. In other instances, $R^3$ is methyl. In certain instances, $R^3$ is ethyl.

In some instances, $R^5$ can be selected from hydrogen, alkyl, substituted alkyl, arylalkyl, substituted arylalkyl, aryl and substituted aryl. In certain instances, $R^5$ is hydrogen. In certain instances, $R^5$ is (1-6C)alkyl. In other instances, $R^5$ is (1-4C)alkyl. In some instances, $R^5$ is selected from methyl, ethyl, n-propyl, isopropyl, n-butyl, t-butyl, pentyl and hexyl. In other instances, $R^5$ is methyl or ethyl. In other instances, $R^5$ is methyl. In certain instances, $R^5$ is ethyl.

In certain instances, $R^5$ is substituted alkyl. In certain instances, $R^5$ is an alkyl group substituted with a carboxylic group such as a carboxylic acid, carboxylic ester or carboxylic amide. In certain instances, $R^5$ is —$(CH_2)_n$—COOH, —$(CH_2)_n$—$COOCH_3$, or —$(CH_2)_n$—$COOCH_2CH_3$, wherein n is a number form one to 10. In certain instances, $R^1$ is —$(CH_2)_5$—COOH, —$(CH_2)_5$—$COOCH_3$, or —$(CH_2)_5$—$COOCH_2CH_3$.

In certain instances, $R^5$ is arylalkyl or substituted arylalkyl. In certain instances, $R^5$ is arylalkyl. In certain instances, $R^5$ is substituted arylalkyl. In certain instances, $R^5$ is an arylalkyl group substituted with a carboxylic group such as a carboxylic acid, carboxylic ester or carboxylic amide. In certain instances, $R^5$ is —$(CH_2)_q(C_6H_4)$—COOH, —$(CH_2)_q(C_6H_4)$—$COOCH_3$, or —$(CH_2)_q(C_6H_4)$—$COOCH_2CH_3$, where q is an integer from one to 10. In certain instances, $R^5$ is —$CH_2(C_6H_4)$—COOH, —$CH_2(C_6H_4)$—$COOCH_3$, or —$CH_2(C_6H_4)$—$COOCH_2CH_3$.

In certain instances, $R^5$ is aryl. In certain instances, $R^5$ is substituted aryl. In certain instances, $R^5$ is an aryl group ortho, meta or para-substituted with a carboxylic group such as a carboxylic acid, carboxylic ester or carboxylic amide. In certain instances, $R^5$ is —$(C_6H_4)$—COOH, —$(C_6H_4)$—$COOCH_3$, or —$(C_6H_4)$—$COOCH_2CH_3$.

In some embodiments, each $R^1$ can be independently selected from hydrogen, alkyl, substituted alkyl, aryl, substituted aryl, acyl, and aminoacyl. In certain instances, $R^1$ is hydrogen or alkyl. In certain instances, $R^1$ is hydrogen. In certain instances, $R^1$ is alkyl. In certain instances, $R^1$ is (1-6C)alkyl. In other instances, $R^1$ is (1-4C)alkyl. In some instances, $R^1$ is selected from methyl, ethyl, n-propyl, isopropyl, n-butyl, t-butyl, pentyl and hexyl. In other instances, $R^1$ is methyl or ethyl. In other instances, $R^1$ is methyl. In certain instances, $R^1$ is ethyl. In certain instances, $R^1$ is acyl. In certain instances, $R^1$ is aminoacyl.

In some embodiments, each $R^2$ can be independently selected from hydrogen, alkyl, substituted alkyl, aryl, substituted aryl, acyl, and aminoacyl. In certain instances, $R^2$ is hydrogen or alkyl. In certain instances, $R^2$ is hydrogen. In certain instances, $R^2$ is alkyl. In certain instances, $R^2$ is (1-6C)alkyl. In other instances, $R^2$ is (1-4C)alkyl. In some instances, $R^2$ is selected from methyl, ethyl, n-propyl, isopropyl, n-butyl, t-butyl, pentyl and hexyl. In other instances, $R^2$ is methyl or ethyl. In other instances, $R^2$ is methyl. In certain instances, $R^2$ is ethyl. In certain instances, $R^2$ is acyl. In certain instances, $R^2$ is aminoacyl.

In certain instances, $R^1$ and $R^2$ are hydrogen. In certain instances, $R^1$ and $R^2$ on the same carbon are both alkyl. In certain instances, $R^1$ and $R^2$ on the same carbon are both (1-6C)alkyl. In other instances, $R^1$ and $R^2$ on the same carbon are both (1-4C)alkyl. In some instances, $R^1$ and $R^2$ on the same carbon are both selected from methyl, ethyl, n-propyl, isopropyl, n-butyl, t-butyl, pentyl and hexyl. In certain instances, $R^1$ and $R^2$ on the same carbon are methyl. In certain instances, $R^1$ and $R^2$ on the same carbon are ethyl.

In certain instances, $R^1$ and $R^1$ which are vicinal are both alkyl and $R^2$ and $R^2$ which are vicinal are both hydrogen. In certain instances, $R^1$ and $R^1$ which are vicinal are both ethyl and $R^2$ and $R^2$ which are vicinal are both hydrogen. In certain instances, $R^1$ and $R^1$ which are vicinal are both methyl and $R^2$ and $R^2$ which are vicinal are both hydrogen.

In certain instances, in the chain of —$[C(R^1)(R^2)]_n$— not every carbon is substituted. In certain instances, in the chain of —$[C(R^1)(R^2)]_n$—, there is a combination of different alkyl substituents, such as methyl or ethyl.

In certain instances, one of $R^1$ and $R^2$ is methyl, ethyl or other alkyl and $R^5$ is alkyl. In certain instances, $R^1$ and $R^1$ which are vicinal are both alkyl and $R^2$ and $R^2$ which are vicinal are both hydrogen and $R^5$ is alkyl. In certain instances, $R^1$ and $R^1$ which are vicinal are both ethyl and $R^2$ and $R^2$ which are vicinal are both hydrogen and $R^5$ is alkyl. In certain instances, $R^1$ and $R^1$ which are vicinal are both methyl and $R^2$ and $R^2$ which are vicinal are both hydrogen and $R^5$ is alkyl.

In certain instances, one of $R^1$ and $R^2$ is methyl, ethyl or other alkyl and $R^5$ is substituted alkyl. In certain instances, one of $R^1$ and $R^2$ is methyl, ethyl or other alkyl and $R^5$ is an alkyl group substituted with a carboxylic group such as a carboxylic acid, carboxylic ester or carboxylic amide. In certain instances, one of $R^1$ and $R^2$ is methyl, ethyl or other alkyl and $R^5$ is —$(CH_2)_q(C_6H_4)$—COOH, —$(CH_2)_q(C_6H_4)$—$COOCH_3$, or —$(CH_2)_q(C_6H_4)$—$COOCH_2CH_3$, where q is an integer from one to 10. In certain instances, one of $R^1$ and $R^2$ is methyl, ethyl or other alkyl and $R^5$ is an alkyl group substituted with carboxamide.

In some instances, $R^1$ and $R^2$ together with the carbon to which they are attached can form a cycloalkyl or substituted cycloalkyl group, or two $R^1$ or $R^2$ groups on adjacent carbon atoms, together with the carbon atoms to which they are attached, can form a cycloalkyl or substituted cycloalkyl group. In certain instances, $R^1$ and $R^2$ together with the carbon to which they are attached can form a cycloalkyl group. Thus, in certain instances, $R^1$ and $R^2$ on the same carbon form a spirocycle. In certain instances, $R^1$ and $R^2$ together with the carbon to which they are attached can form a substituted cycloalkyl group. In certain instances, two $R^1$ or $R^2$ groups on adjacent carbon atoms, together with the carbon atoms to which they are attached, can form a cycloalkyl group. In certain instances, two $R^1$ or $R^2$ groups on adjacent carbon atoms, together with the carbon atoms to which they are attached, can form a substituted cycloalkyl group.

In some embodiments, $R^1$ and $R^2$ together with the carbon to which they are attached can form an aryl or substituted aryl group, or two $R^1$ or $R^2$ groups on adjacent carbon atoms, together with the carbon atoms to which they are attached, can form an aryl or substituted aryl group. In certain instances, two $R^1$ or $R^2$ groups on adjacent carbon atoms, together with the carbon atoms to which they are attached, form a phenyl ring. In certain instances, two $R^1$ or $R^2$ groups on adjacent carbon atoms, together with the carbon atoms to which they are attached, form a substituted phenyl ring. In certain instances, two $R^1$ or $R^2$ groups on adjacent carbon atoms, together with the carbon atoms to which they are attached, form a naphthyl ring.

In certain instances, one of $R^1$ and $R^2$ is aminoacyl. In certain instances, one or both of $R^1$ and $R^2$ is aminoacyl comprising phenylenediamine. In certain instances, one of $R^1$ and $R^2$ is

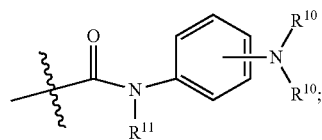

wherein each $R^{10}$ is independently selected from hydrogen, alkyl, substituted alkyl, and acyl and $R^{11}$ is alkyl or substituted alkyl. In certain instances, at least one of $R^{10}$ is acyl. In certain instances, at least one of $R^{10}$ is alkyl or substituted alkyl. In certain instances, at least one of $R^{10}$ is hydrogen. In certain instances, both of $R^{10}$ are hydrogen.

In certain instances, one of $R^1$ and $R^2$ is

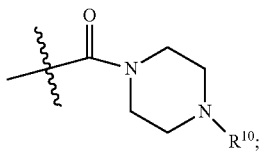

wherein $R^{10}$ is hydrogen, alkyl, substituted alkyl, or acyl. In certain instances, $R^{10}$ is acyl. In certain instances, $R^{10}$ is alkyl or substituted alkyl. In certain instances, $R^{10}$ is hydrogen.

In certain instances, one of $R^1$ and $R^2$ is

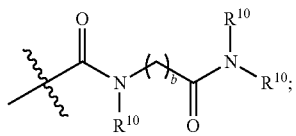

wherein each $R^{10}$ is independently hydrogen, alkyl, substituted alkyl, or acyl and b is a number from one to 5. In certain instances, one of $R^1$ and $R^2$ is

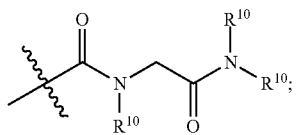

wherein each $R^{10}$ is independently hydrogen, alkyl, substituted alkyl, or acyl. In certain instances, one of $R^1$ and $R^2$ is

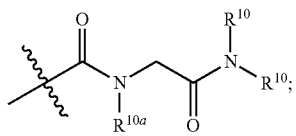

wherein $R^{10a}$ is alkyl and each $R^{10}$ is independently hydrogen, alkyl, substituted alkyl, or acyl.

In certain instances, one of $R^1$ and $R^2$ is

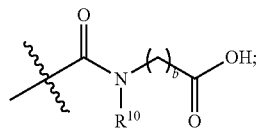

wherein $R^{10}$ is independently hydrogen, alkyl, substituted alkyl, or acyl and b is a number from one to 5. In certain instances, one of $R^1$ and $R^2$ is

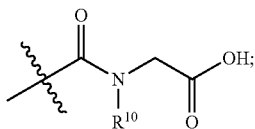

wherein $R^{10}$ is independently hydrogen, alkyl, substituted alkyl, or acyl.

In certain instances, one of $R^1$ and $R^2$ is an aminoacyl group, such as —C(O)NR$^{10a}$R$^{10b}$, wherein each $R^{10a}$ and $R^{10b}$ is independently selected from hydrogen, alkyl, substituted alkyl, and acyl. In certain instances, one of $R^1$ and $R^2$ is an aminoacyl group, such as —C(O)NR$^{10a}$R$^{10b}$, wherein $R^{10a}$ is an alkyl and $R^{10b}$ is substituted alkyl. In certain instances, one of $R^1$ and $R^2$ is an aminoacyl group, such as —C(O)NR$^{10a}$R$^{10b}$, wherein $R^{10a}$ is an alkyl and $R^{10b}$ is alkyl substituted with a carboxylic acid or carboxyl ester. In certain instances, one of $R^1$ and $R^2$ is an aminoacyl group, such as —C(O)NR$^{10a}$R$^{10b}$, wherein $R^{10a}$ is methyl and $R^{10b}$ is alkyl substituted with a carboxylic acid or carboxyl ester.

In certain instances, $R^1$ or $R^2$ can modulate a rate of intramolecular cyclization. $R^1$ or $R^2$ can speed up a rate of intramolecular cyclization, when compared to the corresponding molecule where $R^1$ and $R^2$ are both hydrogen. In certain instances, $R^1$ or $R^2$ comprise an electron-withdrawing group or an electron-donating group. In certain instances, $R^1$ or $R^2$ comprise an electron-withdrawing group. In certain instances, $R^1$ or $R^2$ comprise an electron-donating group.

Atoms and groups capable of functioning as electron withdrawing substituents are well known in the field of organic chemistry. They include electronegative atoms and groups containing electronegative atoms. Such groups function to lower the basicity or protonation state of a nucleophilic nitrogen in the beta position via inductive withdrawal of electron density. Such groups can also be positioned on other positions along the alkylene chain. Examples include halogen atoms (for example, a fluorine atom), acyl groups (for example an alkanoyl group, an aroyl group, a carboxyl group, an alkoxycarbonyl group, an aryloxycarbonyl group or an aminocarbonyl group (such as a carbamoyl, alkylaminocarbonyl, dialkylaminocarbonyl or arylaminocarbonyl group)), an oxo (=O) substituent, a nitrile group, a nitro group, ether groups (for example an alkoxy group) and phenyl groups bearing a substituent at the ortho position, the para position or both the ortho and the para positions, each substituent being selected independently from a halogen atom, a fluoroalkyl group (such as trifluoromethyl), a nitro group, a cyano group and a carboxyl group. Each of the electron withdrawing substituents can be selected independently from these.

In certain instances, —[C(R$^1$)(R$^2$)]$_n$— is selected from —CH(CH$_2$F)CH(CH$_2$F)—; —CH(CHF$_2$)CH(CHF$_2$)—; —CH(CF$_3$)CH(CF$_3$)—; —CH$_2$CH(CF$_3$)—; —CH$_2$CH(CHF$_2$)—; —CH$_2$CH(CH$_2$F)—; —CH$_2$CH(F)CH$_2$—; —CH$_2$C(F$_2$)CH$_2$—; —CH$_2$CH(C(O)NR$^{20}$R$^{21}$)—; —CH$_2$CH(C(O)OR$^{22}$)—; —CH$_2$CH(C(O)OH)—; —CH(CH$_2$F)CH$_2$CH(CH$_2$F)—; —CH(CHF$_2$)CH$_2$CH(CHF$_2$)—; —CH(CF$_3$)CH$_2$CH(CF$_3$)—; —CH$_2$CH$_2$CH(CF$_3$)—; —CH$_2$CH$_2$CH(CHF$_2$)—; —CH$_2$CH$_2$CH(CH$_2$F)—; —CH$_2$CH$_2$CH(C(O)NR$^{23}$R$^{24}$)—; —CH$_2$CH$_2$CH(C(O)OR$^{25}$)—; and —CH$_2$CH$_2$CH(C(O)OH)—, in which R$^{20}$, $R^{21}$, $R^{22}$ and $R^{23}$ each independently represents hydrogen or (1-6C)alkyl, and $R^{24}$ and $R^{25}$ each independently represents (1-6C)alkyl.

In methadone prodrug compounds according to embodiments of the present disclosure, n can be an integer from 1 to 10. In certain instances, n is one. In certain instances, n is two. In other instances, n is three. In other instances, n is four. In certain instances, n is five.

In methadone prodrug compounds according to embodiments of the present disclosure, a can be an integer from 1 to 10. In certain instances, a is one. In certain instances, a is two. In other instances, a is three. In other instances, a is four. In certain instances, a is five.

In methadone prodrug compounds according to embodiments of the present disclosure, a can be an integer from 1 to 10. In certain instances, m is one. In certain instances, m is two. In other instances, m is three. In other instances, m is four. In certain instances, m is five.

In methadone prodrug compounds according to embodiments of the present disclosure, c can be an integer from 1 to 10. In certain instances, c is one. In certain instances, c is two. In other instances, c is three. In other instances, c is four. In certain instances, c is five.

In embodiments, $R^4$ is

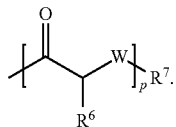

In some embodiments, each $R^6$ can be independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^6$ and 127 together with the atoms to which they are bonded form a cycloheteroalkyl or substituted cycloheteroalkyl ring.

In certain instances, $R^6$ is selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl. In certain instances, $R^6$ is selected from hydrogen, alkyl, substituted alkyl, arylalkyl, substituted arylalkyl, heteroarylalkyl, and substituted heteroarylalkyl. In certain instances, $R^6$ is hydrogen. In certain instances, $R^6$ is alkyl. In certain instances, $R^6$ is substituted alkyl. In certain instances, $R^6$ is arylalkyl or substituted arylalkyl. In certain instances, $R^6$ is heteroarylalkyl or substituted heteroarylalkyl.

In certain instances, $R^6$ is a side chain of an amino acid, such as alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine. In certain instances, $R^6$ is a side chain of an L-amino acid, such as L-alanine, L-arginine, L-asparagine, L-aspartic acid, L-cysteine, L-glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine or L-valine. In certain instances, $R^6$ is —$CH_2CH_2CH_2NH(C=NH)NH_2$.

In some embodiments, each W can be independently —O— or —S—. In certain instances, W is —$NR^8$—. In certain instances, W is —O—. In certain instances, W is —S—. In some instances, each $R^8$ can be independently hydrogen, alkyl, substituted alkyl, aryl or substituted aryl, or optionally, each $R^6$ and $R^8$ independently together with the atoms to which they are bonded form a cycloheteroalkyl or substituted cycloheteroalkyl ring.

In certain instances, $R^8$ is hydrogen or alkyl. In certain instances, $R^8$ is hydrogen. In certain instances, $R^8$ is alkyl. In certain instances, $R^8$ is aryl. In certain instances, $R^6$ and $R^8$ independently together with the atoms to which they are bonded form a cycloheteroalkyl or substituted cycloheteroalkyl ring.

In some embodiments, p can be an integer from one to 100 and each $R^6$ can be selected independently from a side chain of any amino acid. In certain instances, p is an integer from one to 50. In certain instances, p is an integer from one to 90, 80, 70, 60, 50, 40, 30, 20, or 10. In certain instances, p is about 100. In certain instances, p is about 75. In certain instances, p is about 50. In certain instances, p is about 25. In certain instances, p is about 20. In certain instances, p is about 15. In certain instances, p is about 10. In certain instances, p is about 9. In certain instances, p is about 8. In certain instances, p is about 7. In certain instances, p is about 6. In certain instances, p is about 5. In certain instances, p is about 4. In certain instances, p is about 3. In certain instances, p is about 2. In certain instances, p is about one.

In certain instances, the $R^6$ of $R^4$ adjacent to the nitrogen of —$N(R^3)(R^4)$ is —$CH_2CH_2CH_2NH(C=NH)NH_2$ or —$CH_2CH_2CH_2CH_2NH_2$, and any additional $R^6$ can be a side chain of any amino acid independently selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine or valine.

In some embodiments, $R^7$ can be selected from hydrogen, alkyl, substituted alkyl, acyl, substituted acyl, alkoxycarbonyl, substituted alkoxycarbonyl, aryl, substituted aryl, arylalkyl, and substituted arylalkyl. In certain instances, $R^7$ is hydrogen, alkyl, acyl, or substituted acyl. In certain instances, $R^7$ is hydrogen. In certain instances, $R^7$ is alkyl. In certain instances, $R^7$ is acyl or substituted acyl. In certain instances, $R^7$ is acyl. In certain instances, $R^7$ is substituted acyl. In certain instances, $R^7$ can be formyl, acetyl, benzoyl, propionyl, malonyl, succinyl, benzoyl or piperonyl.

In some embodiments, $R^4$ can be a residue of an L-amino acid selected from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine, or a residue of an N-acyl derivative of any of said amino acids; or a residue of a peptide composed of at least two L-amino acid residues selected independently from alanine, arginine, asparagine, aspartic acid, cysteine, glycine, glutamine, glutamic acid, histidine, isoleucine, leucine, lysine, methionine, phenylalanine, proline, threonine, tryptophan, tyrosine and valine or a residue of an N-acyl derivative thereof. Such a peptide can be from 2 to about 100 amino acids in length. Examples of N-acyl derivatives include formyl, acetyl, benzoyl, propionyl, malonyl, succinyl, benzoyl or piperonyl derivatives.

In some instances, $R^4$ is a residue of L-arginine or a residue of an N-acyl derivative of L-arginine.

In certain instances, the N-acyl derivative is a formyl, acetyl, benzoyl, propionyl, malonyl, succinyl, benzoyl or piperonyl derivative.

In certain instances, when p is greater than one, then the $R^4$ adjacent to the nitrogen of —$N(R^3)(R^4)$ is a residue of L-arginine or L-lysine. In certain instances, when p is greater than one, the $R^4$ adjacent to the nitrogen of $-N(R^3)(R^4)$ is a residue of L-arginine or L-lysine and the first residue is joined to at least one additional L-amino acid residue selected independently from alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. The terminal residue of the peptide can be an N-acyl derivative of any of such L-amino acids. In certain instances $R^4$ is a dipeptide or an N-acyl derivative thereof. In certain instances R is a tripeptide or an N-acyl derivative thereof.

In some embodiments, the A ring is a heterocyclic 5 to 12-membered ring. In some instances, the A ring is a 5-membered ring. In some instances, the A ring is a 6-membered ring. In certain instances, the A ring is a 5-membered nitrogen-containing ring. In certain instances, the A ring is a 5-membered oxygen-containing ring. In certain instances, the A ring is a 5-membered sulfur-containing ring. In certain instances, the A ring is a 6-membered nitrogen-containing ring. In certain instances, the A ring is a 6-membered oxygen-containing ring. In certain instances, the A ring is a 6-membered sulfur-containing ring.

In some embodiments, $A^1$, $A^2$, $A^4$, and $A^5$ are independently selected from carbon, nitrogen, oxygen, and sulfur. In some instances, $A^1$ is carbon. In some instances, $A^1$ is oxygen In some instances, $A^1$ is nitrogen. In some instances, $A^1$ is sulfur. In some instances, $A^2$ is carbon. In some instances, $A^2$ is oxygen. In some instances, $A^2$ is nitrogen. In some instances, $A^2$ is sulfur. In some instances, $A^3$ is carbon. In some instances, $A^3$ is oxygen. In some instances, $A^3$ is nitrogen. In some instances, $A^3$ is sulfur. In some instances, $A^4$ is carbon. In some instances, $A^4$ is oxygen. In some instances, $A^4$ is nitrogen. In some instances, $A^4$ is sulfur. In some instances, $A^5$ is carbon. In some instances, $A^5$ is oxygen. In some instances, $A^5$ is nitrogen. In some instances, $A^5$ is sulfur.

In some instances, the chain of $-[C(R^1)(R^2)]_a$ is substituted at $A^1$. In some instances, the chain of $[C(R^1)(R^2)]_a$ is substituted at $A^2$. In some instances, the chain of $[C(R^1)(R^2)]_a-$ is substituted at $A^3$. In some instances, the chain of $-[C(R^1)(R^2)]_a-$ is substituted at $A^4$. In some instances, the chain of $-[C(R^1)(R^2)]_a-$ is substituted at $A^5$.

In some instances, the chain of $-[C(R^1)(R^2)]_n-$ is substituted ortho to the chain of $-[C(R^1)(R^2)]_m-$. In some instances, the chain of $-[C(R^1)(R^2)]_n-$ is substituted meta to the chain of $-[C(R^1)(R^2)]_m-$. In some instances, the chain of $-[C(R^1)(R^2)]_n-$ is substituted para to the chain of $-[C(R^1)(R^2)]_m-$.

In certain embodiments, the methadone prodrug is Compound MD-101:

Compound MD-101 or a salt, hydrate or solvate thereof.

In certain embodiments, the methadone prodrug is Compound MD-102:

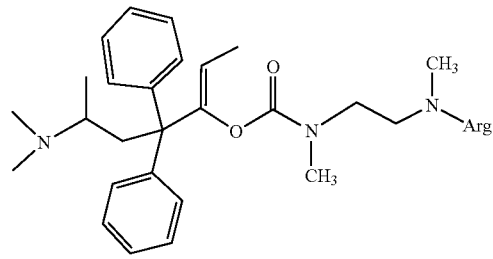

Compound MD-102 or a salt, hydrate or solvate thereof.

In certain embodiments, the methadone prodrug is Compound MD-103:

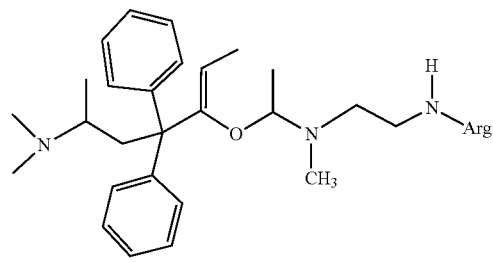

Compound MD-103 or a salt, hydrate or solvate thereof.

In certain embodiments, the methadone prodrug is Compound MD-104:

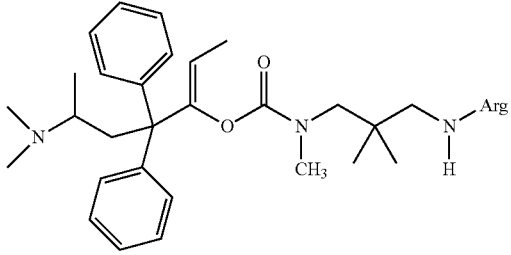

Compound MD-104 or a salt, hydrate or solvate thereof.

In certain embodiments, the methadone prodrug is Compound MD-105:

Compound MD-105

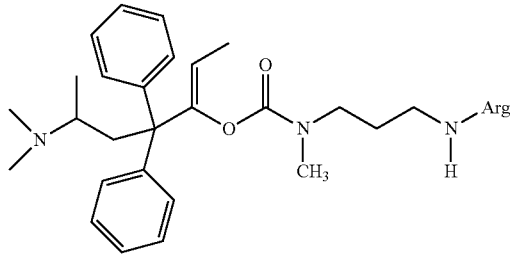

or a salt, hydrate or solvate thereof.

In certain embodiments, the methadone prodrug is Compound MD-106:

Compound MD-106

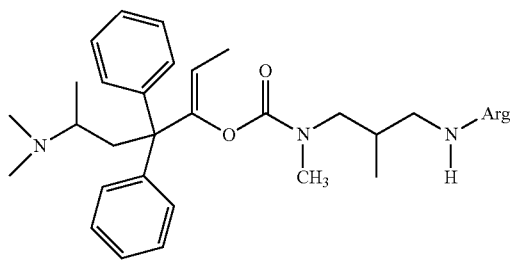

or a salt, hydrate or solvate thereof.

In certain embodiments, the methadone prodrug is Compound MD-107:

Compound MD-107

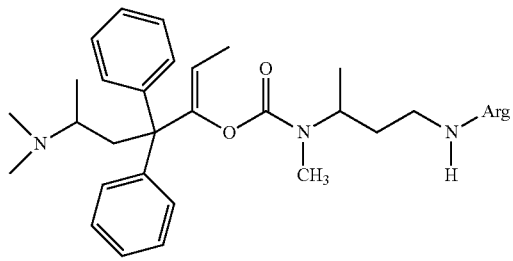

or a salt, hydrate or solvate thereof.

In certain embodiments, the methadone prodrug is Compound MD-108:

Compound MD-108

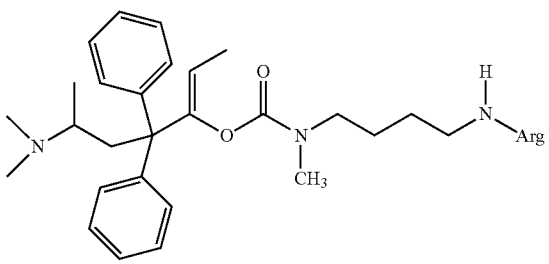

or a salt, hydrate or solvate thereof.

In certain embodiments, the methadone prodrug is Compound MD-109:

Compound MD-109

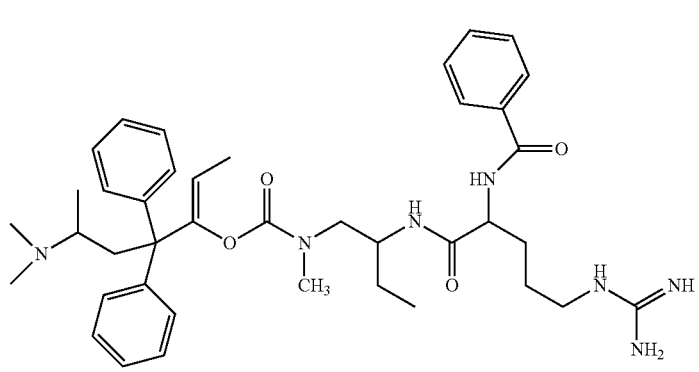

or a salt, hydrate or solvate thereof.

In certain embodiments, the methadone prodrug is Compound MD-110:
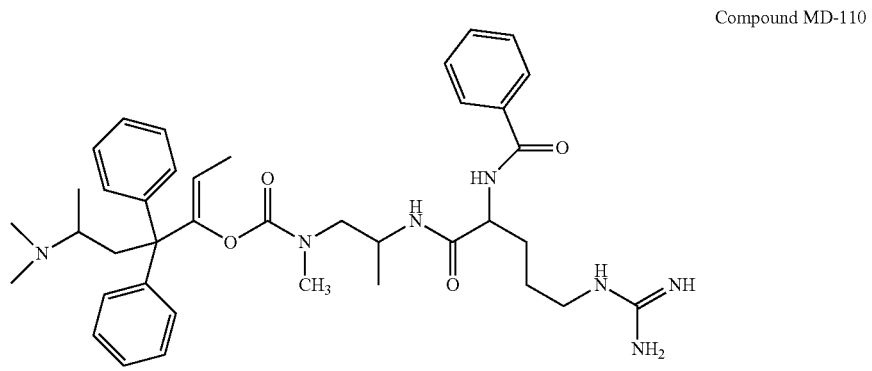 [SMILES: C/C=C(\OC(=O)N(C)CC(C)NC(=O)C(CCCNC(=N)N)NC(=O)c1ccccc1)C(CC(C)N(C)C)(c1ccccc1)c1ccccc1]
Compound MD-110
or a salt, hydrate or solvate thereof.
In certain embodiments, the methadone prodrug is Compound MD-111:
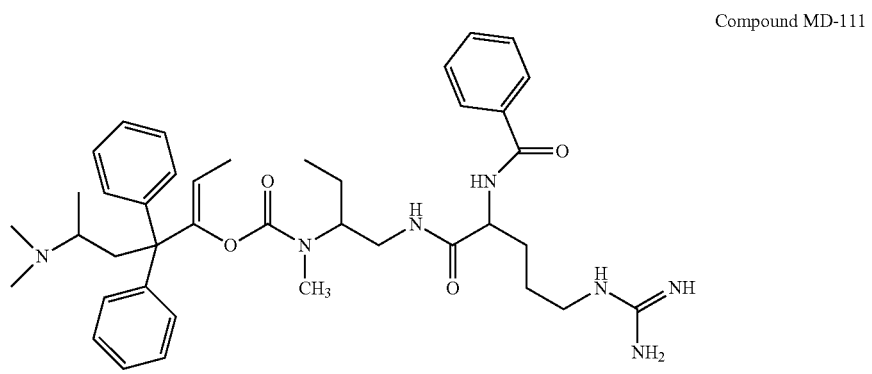 [SMILES: C/C=C(\OC(=O)N(C)C(CC)CNC(=O)C(CCCNC(=N)N)NC(=O)c1ccccc1)C(CC(C)N(C)C)(c1ccccc1)c1ccccc1]
Compound MD-111
or a salt, hydrate or solvate thereof.
In certain embodiments, the methadone prodrug is Compound MD-112:
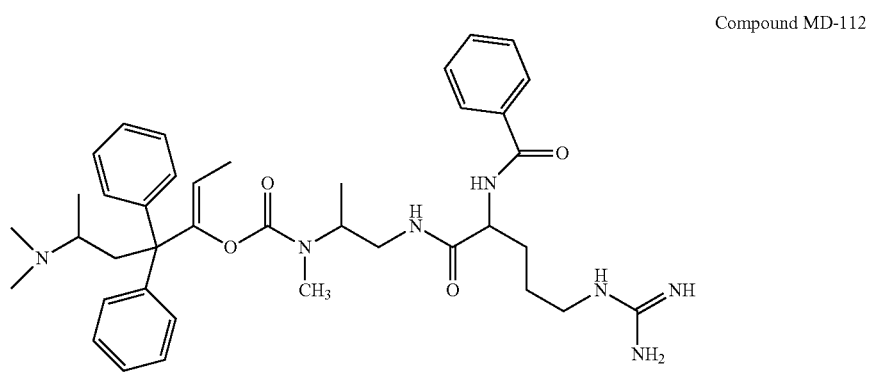 [SMILES: C/C=C(\OC(=O)N(C)C(C)CNC(=O)C(CCCNC(=N)N)NC(=O)c1ccccc1)C(CC(C)N(C)C)(c1ccccc1)c1ccccc1]
Compound MD-112
or a salt, hydrate or solvate thereof.

In certain embodiments, the methadone prodrug is Compound MD-113:
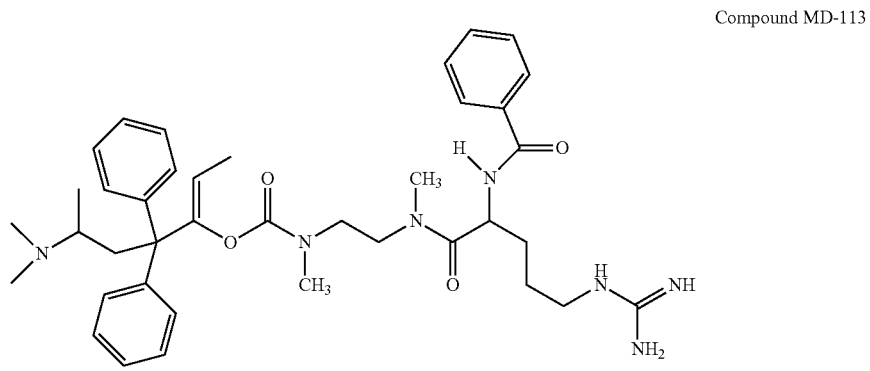 [SMILES: C/C=C(\OC(=O)N(C)CCN(C)C(=O)C(CCCNC(=N)N)NC(=O)c1ccccc1)C(CC(C)N(C)C)(c1ccccc1)c1ccccc1]
Compound MD-113
or a salt, hydrate or solvate thereof.
In certain embodiments, the methadone prodrug is Compound MD-114:
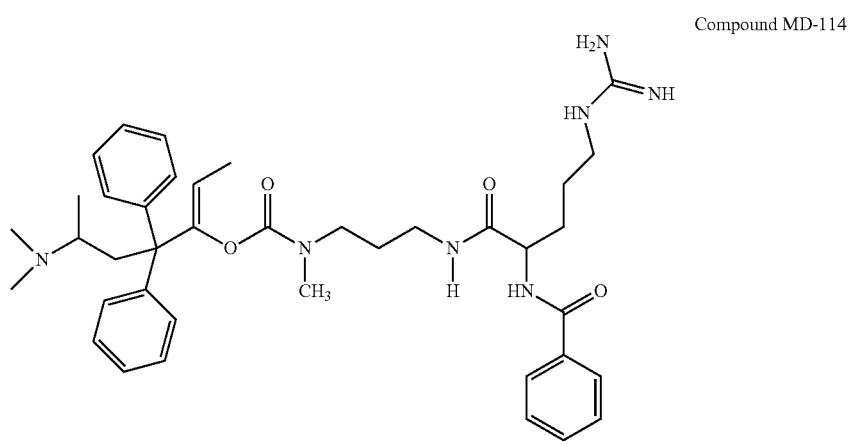 [SMILES: C/C=C(\OC(=O)N(C)CCCNC(=O)C(CCCNC(=N)N)NC(=O)c1ccccc1)C(CC(C)N(C)C)(c1ccccc1)c1ccccc1]
Compound MD-114
or a salt, hydrate or solvate thereof.
In certain embodiments, the methadone prodrug is Compound MD-115:
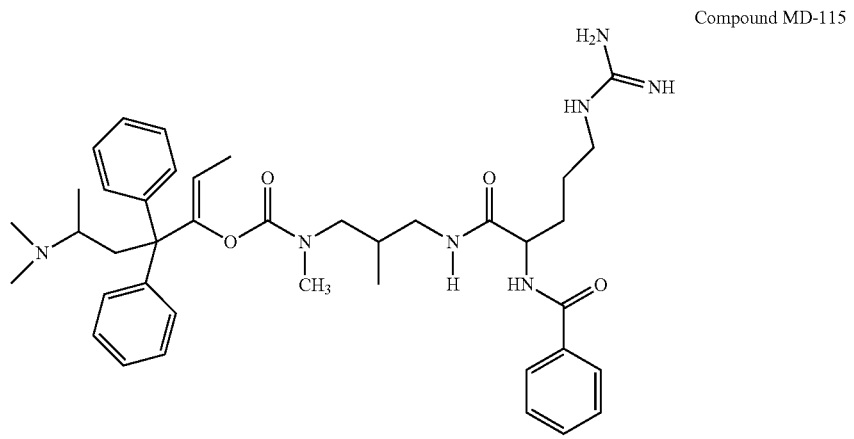 [SMILES: C/C=C(\OC(=O)N(C)CC(C)CNC(=O)C(CCCNC(=N)N)NC(=O)c1ccccc1)C(CC(C)N(C)C)(c1ccccc1)c1ccccc1]
Compound MD-115
or a salt, hydrate or solvate thereof.

In certain embodiments, the methadone prodrug is Compound MD-116:
Compound MD-116
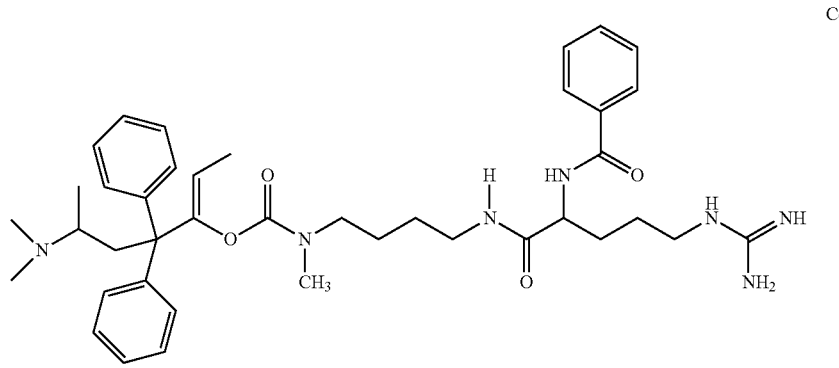
or a salt, hydrate or solvate thereof.
In certain embodiments, the methadone prodrug is Compound MD-117:
Compound MD-117
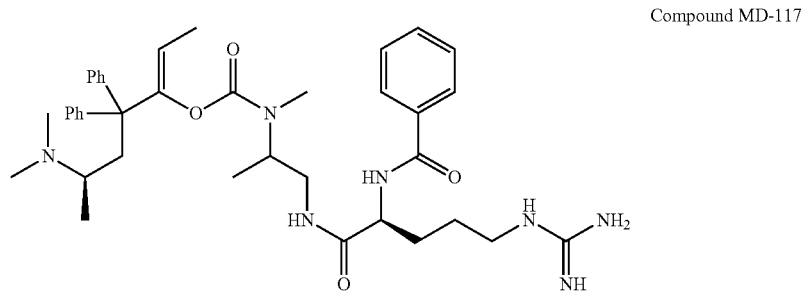 [SMILES: C/C=C(\OC(=O)N(C)C(C)CNC(=O)[C@H](CCCNC(=N)N)NC(=O)c1ccccc1)C(C[C@@H](C)N(C)C)(c1ccccc1)c1ccccc1]
or a salt, hydrate or solvate thereof.
In certain embodiments, the methadone prodrug is Compound MD-118:
Compound MD-118
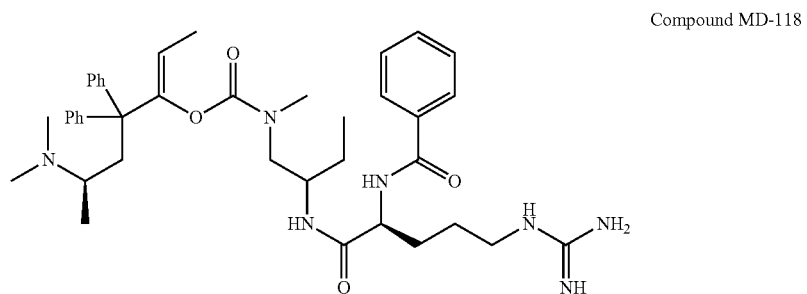 [SMILES: C/C=C(\OC(=O)N(C)CC(CC)NC(=O)[C@H](CCCNC(=N)N)NC(=O)c1ccccc1)C(C[C@@H](C)N(C)C)(c1ccccc1)c1ccccc1]
or a salt, hydrate or solvate thereof.

In certain embodiments, the methadone prodrug is Compound MD-119:

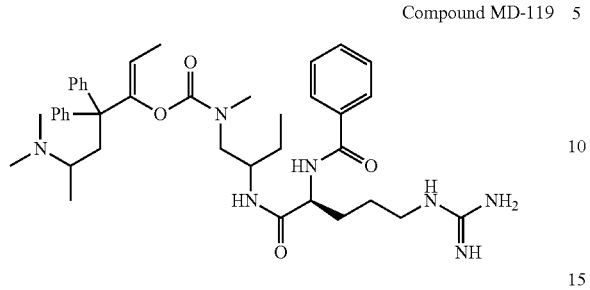

Compound MD-119 or a salt, hydrate or solvate thereof.

In certain embodiments, the methadone prodrug is Compound MD-120:

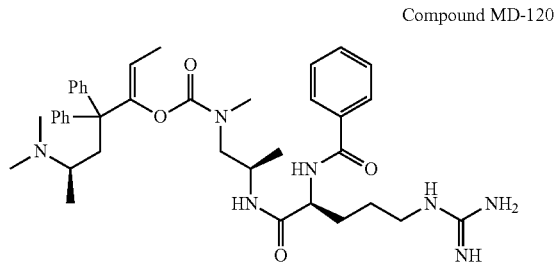 [SMILES: C/C=C(\OC(=O)N(C)C[C@@H](C)NC(=O)[C@H](CCCNC(=N)N)NC(=O)c1ccccc1)C(C[C@@H](C)N(C)C)(c1ccccc1)c1ccccc1]

Compound MD-120 or a salt, hydrate or solvate thereof.

In certain embodiments, the methadone prodrug is Compound MD-121:

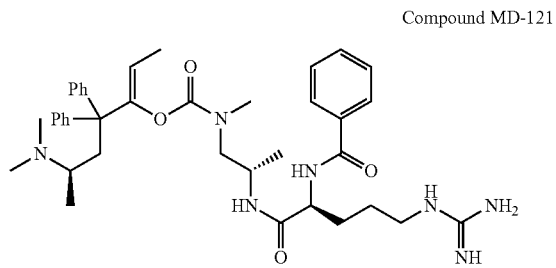 [SMILES: C/C=C(\OC(=O)N(C)C[C@H](C)NC(=O)[C@H](CCCNC(=N)N)NC(=O)c1ccccc1)C(C[C@@H](C)N(C)C)(c1ccccc1)c1ccccc1]

Compound MD-121 or a salt, hydrate or solvate thereof.

In certain embodiments, the methadone prodrug is Compound MD-122:

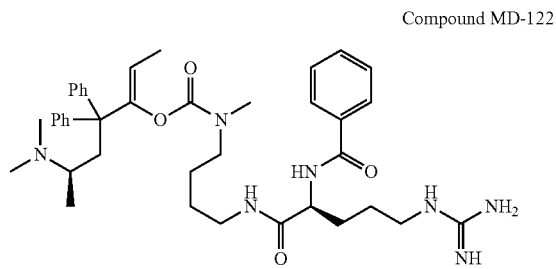 [SMILES: C/C=C(\OC(=O)N(C)CCCCNC(=O)[C@H](CCCNC(=N)N)NC(=O)c1ccccc1)C(C[C@@H](C)N(C)C)(c1ccccc1)c1ccccc1]

Compound MD-122 or a salt, hydrate or solvate thereof.

In certain embodiments, the methadone prodrug is Compound MD-301:

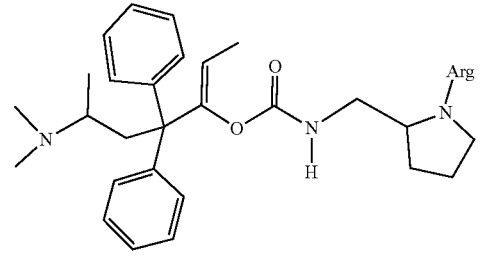

Compound MD-301 or a salt, hydrate or solvate thereof.

In certain embodiments, the methadone prodrug is Compound MD-302:

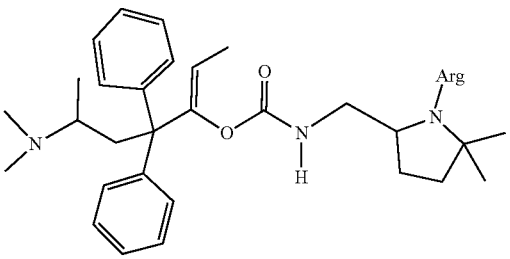

Compound MD-302 or a salt, hydrate or solvate thereof.

In certain embodiments, the methadone prodrug is Compound MD-303:

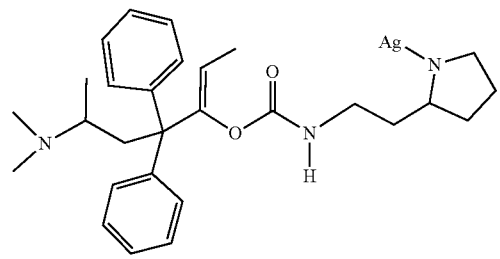

Compound MD-303 or a salt, hydrate or solvate thereof.

In certain embodiments, the methadone prodrug is Compound 304:

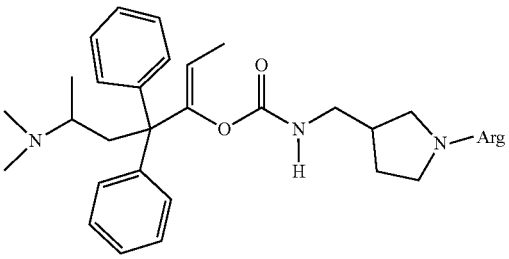

Compound MD-304 or a salt, hydrate or solvate thereof.

In certain embodiments, the methadone prodrug is Compound MD-305:

Compound MD-305

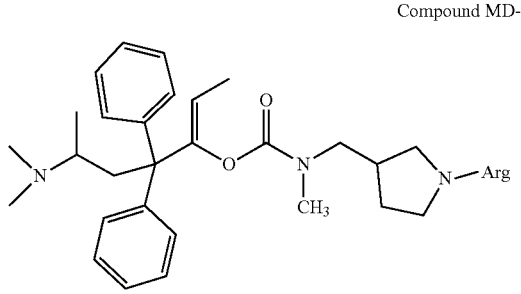

or a salt, hydrate or solvate thereof.

In certain embodiments, the methadone prodrug is Compound MD-306:

Compound MD-306

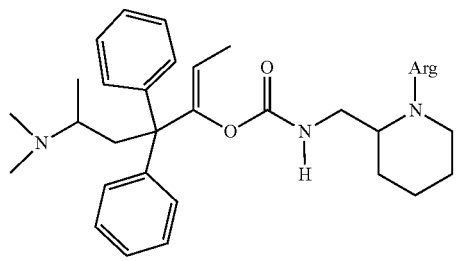

or a salt, hydrate or solvate thereof.

In certain embodiments, the methadone prodrug is Compound MD-307:

Compound MD-307

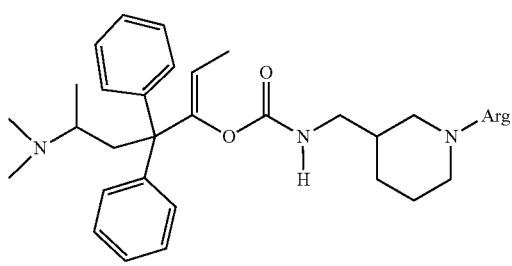

or a salt, hydrate or solvate thereof.

In certain embodiments, the methadone prodrug is Compound MD-308:

Compound MD-308

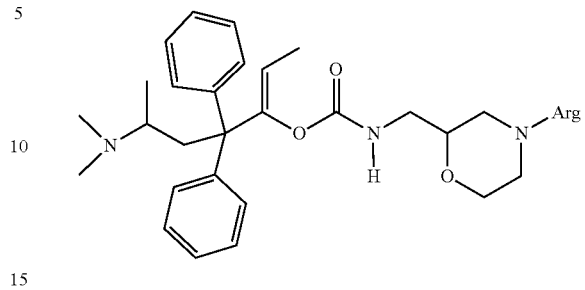

or a salt, hydrate or solvate thereof.

In certain embodiments, the methadone prodrug is Compound MD-309:

Compound MD-309

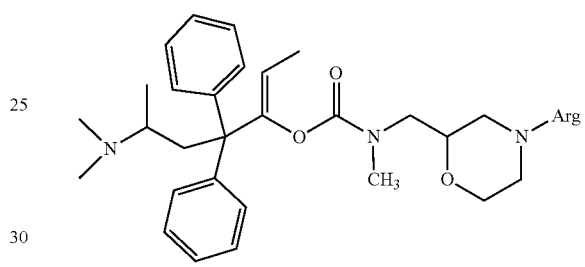

or a salt, hydrate or solvate thereof.

In certain embodiments, the methadone prodrug is Compound MD-310:

Compound MD-310

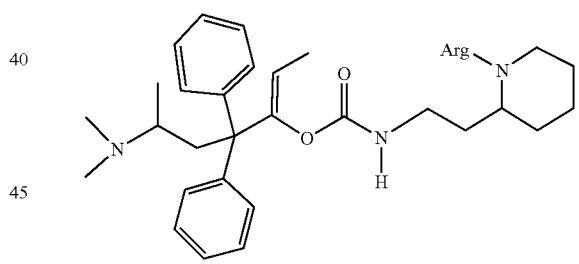

or a salt, hydrate or solvate thereof.

In certain embodiments, the methadone prodrug is Compound MD-401:

Compound MD-401

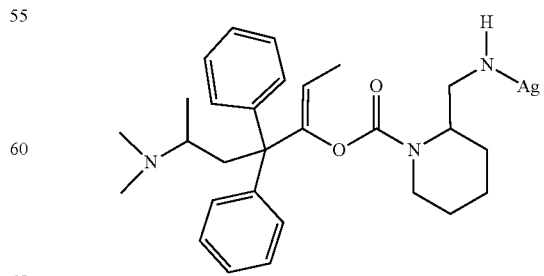

or a salt, hydrate or solvate thereof.

In certain embodiments, the methadone prodrug is Compound MD-402:

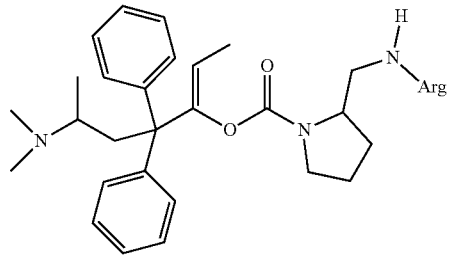

Compound MD-402 or a salt, hydrate or solvate thereof.

In certain embodiments, the methadone prodrug is Compound MD-403:

Compound MD-403

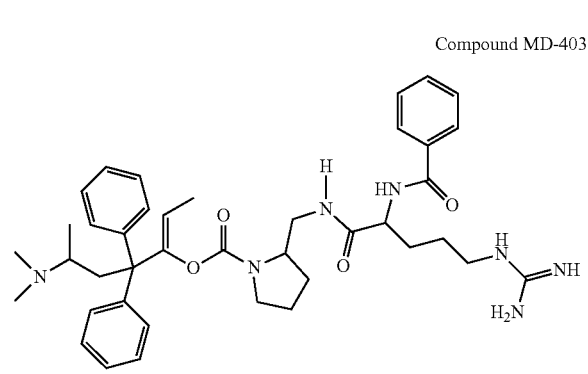 [SMILES: C/C=C(\OC(=O)N1CCCC1CNC(=O)C(CCCNC(=N)N)NC(=O)c1ccccc1)C(CC(C)N(C)C)(c1ccccc1)c1ccccc1]

or a salt, hydrate or solvate thereof.

In certain embodiments, the methadone prodrug is Compound MD-404:

Compound MD-404

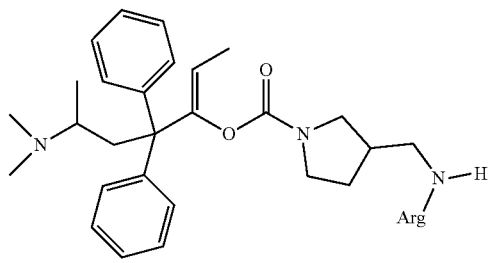

or a salt, hydrate or solvate thereof.

In certain embodiments, the methadone prodrug is Compound MD-405:

Compound MD-405

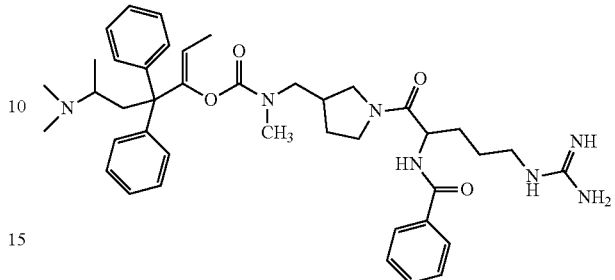

or a salt, hydrate or solvate thereof.

In certain embodiments, the methadone prodrug is Compound MD-406:

Compound MD-406

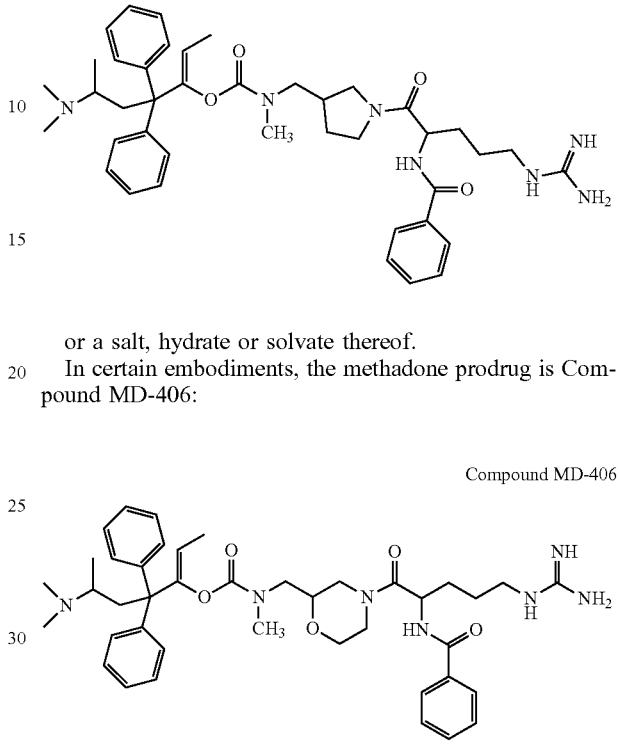

or a salt, hydrate or solvate thereof.

Amino Acids Found in Prodrugs

"Amino acid" means a building block of a polypeptide. As used herein, "amino acid" includes the 20 common naturally occurring L-amino acids and all amino acids variants. In certain embodiments, an amino acid is a cleavable substrate for a gastrointestinal enzyme.

"Naturally occurring amino acids" means the 20 common naturally occurring L-amino acids, that is, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

"Amino acid variants" means an amino acid other than any of the 20 common naturally occurring L-amino acids that is hydrolysable by a protease in a manner similar to the ability of a protease to hydrolyze a naturally occurring L-amino acid. Amino acid variants, thus, include amino acids or analogs of amino acids other than the 20 naturally-occurring amino acids. Amino acid variants include synthetic amino acids. Amino acid variants also include amino acid derivatives. A derivative refers to a substance that has been altered from another substance by modification, partial substitution, homologation, truncation, or a change in oxidation state while retaining the ability to be cleaved by a GI enzyme.

Certain examples of amino acid variants include, but are not limited to:
2-aminoindane-2-carboxylic acid, 2-aminoisobutyric acid, 4-amino-phenylalanine, 5-hydroxylysine, biphenylalanine, citrulline, cyclohexylalanine, cyclohexylglycine, diethylglycine, dipropylglycine, homoarginine, homocitrulline, homophenylalanine, homoproline, homoserine, homotyrosine, hydroxyproline, lanthionine, naphthylalanine, norleucine, ornithine, phenylalanine(4-fluoro), phenylalanine(4-nitro), phenylglycine, pipecolic acid, tert-butylalanine, tert-butylglycine, tert-leucine, tetrahydroisoquinoline-3-carboxylic acid, α-aminobutyric acid, γ-amino butyric acid, 2,3-diaminoproprionic acid, phenylalanine(2,3,4,5,6 pentafluoro), aminohexanoic acid and derivatives thereof.

Certain examples of amino acid variants include, but are not limited to, N-methyl amino acids. For example, N-methyl-alanine, N-methyl aspartic acid, N-methyl-glutamic acid, N-methyl-glycine (sarcosine) are N-methyl amino acids.

Certain examples of amino acid variants include, but are not limited to: dehydroalanine, ethionine, hypusine, lanthionine, pyrrolysine, α-aminoisobutyric acid, selenomethionine and derivatives thereof.

Certain examples of amino acid variants include, but are not limited to: (3, 2-amino benzoic acid, 2-amino methyl benzoic acid, 2-amino-3-guanidinopropionic acid, 2-amino-3-methoxy benzoic acid, 2-amino-3-ureidopropionic acid, 3-amino benzoic acid, 4-amino benzoic acid, 4-amino methyl benzoic acid, 4-nitroanthranillic acid, 5-acetamido-2-aminobenzoic acid, butanoic acid (HMB), glutathione, homocysteine, statine, taurine, β-alanine, 2-hydroxy-4-(methylthio), (3,4)-diamino benzoic acid, (3,5)-diamino benzoic acid and derivatives thereof.

Certain examples of amino acid variants include, but are not limited to: (2 amino ethyl) cysteine, 2-amino-3-ethyoxybutanoic acid, buthionine, cystathion, cysteic acid, ethionine, ethoxytheorine, methylserine, N-ε-ε-dimethyl-lysine, N-ω-nitro-arginine, saccharopine, isoserine derivatives thereof, and combinations thereof.

Certain examples of amino acid variants include, but are not limited to: l-carnitine, selenocysteine, l-sarcosine, l-lysinol, benzoic acid, citric acid, choline, EDTA or succinic acid and derivatives thereof.

Certain examples of amino acid variants are amino alcohols. Examples of amino alcohols include, but are not limited to: alaninol, indano, norephedrine, asparaginol, aspartimol, glutamol, leucinol, methioninol, phenylalaninol, prolinol, tryptophanol, valinol, isoleucinol, argininol, serinol, tyrosinol, threoninol, cysteinol, lysinol, histidinol and derivatives thereof.

In some embodiments, the methadone prodrugs are formulated in any convenient form suitable for oral (including buccal and sublingual) administration for example as a tablet, capsule, powder, suspension, dispersion or emulsion. Pharmaceutical compositions of the methadone prodrug may include one or more pharmaceutically acceptable carriers. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc. For example, the one or more excipients may include sucrose, starch, mannitol, sorbitol, lactose, glucose, cellulose, talc, calcium phosphate or calcium carbonate, a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

The amount of methadone prodrug in a unit composition, for example, a capsule or tablet of the methadone prodrug or pharmaceutically acceptable salt thereof, may include from 1 mg and 400 mg of methadone prodrug or pharmaceutically acceptable salt thereof, for example, between: 1 and 10 mg, 10 and 20 mg, 20 and 30 mg, 30 and 40 mg, 40 and 50 mg, 50 and 60 mg, 60 and 70 mg, 70 and 80 mg, 80 and 90 mg, 90 and 100 mg, 100 and 110 mg, 110 and 120 mg, 120 and 130 mg, 130 and 140 mg, 140 and 150 mg, 150 and 160 mg, 160 and 170 mg, 170 and 180 mg, 180 and 190 mg, 190 and 200 mg, 200 and 210 mg, 210 and 220 mg, 220 and 230 mg, 230 and 240 mg, 240 and 250 mg, 250 and 260 mg, 260 and 270 mg, 270 and 280 mg, 280 and 290 mg, 290 and 300 mg, 300 and 310 mg, 310 and 320 mg, 320 and 330 mg, 330 and 340 mg, 340 and 350 mg, 350 and 360 mg, 360 and 370 mg, 370 and 380 mg, 380 and 390 mg and between 390 and 400 mg.

In some embodiments, compositions of interest include an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. In some instances, compositions of interest further include a preservative. Suitable preservatives include, but are not limited to, a benzyl alcohol, phenol, chlorobutanol, benzalkonium chloride, and the like. In many cases, the composition is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, pharmaceutical compositions of the methadone prodrug include other additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Trypsin Inhibitors

As disclosed herein, the present disclosure also provides pharmaceutical compositions, and their methods of use, where the pharmaceutical compositions comprise a methadone prodrug, that provides controlled release of methadone via enzyme cleavage followed by intramolecular cyclization, and a trypsin inhibitor that interacts with the enzyme that mediates the enzymatically-mediated release of methadone from the prodrug so as to attenuate enzymatic cleavage of the prodrug. Such disclosure provides for the enzyme being trypsin.

As used herein, the term "trypsin inhibitor" refers to any agent capable of inhibiting the action of trypsin on a substrate. The term "trypsin inhibitor" also encompasses salts of trypsin inhibitors. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241, 3955 and Y. Birk, 1976, Meth. Enzymol. 45, 700. In certain instances, a trypsin inhibitor can interact with an active site of trypsin, such as the 51 pocket and the S3/4 pocket. The 51 pocket has an aspartate residue which has affinity for a positively charged moiety. The S3/4 pocket is a hydrophobic pocket. The disclosure provides for specific trypsin inhibitors and non-specific serine protease inhibitors.

There are many trypsin inhibitors known in the art, both those specific to trypsin and those that inhibit trypsin and other proteases such as chymotrypsin. The disclosure provides for trypsin inhibitors that are proteins, peptides, and small molecules. The disclosure provides for trypsin inhibitors that are irreversible inhibitors or reversible inhibitors. The disclosure provides for trypsin inhibitors that are competitive inhibitors, non-competitive inhibitors, or uncompetitive inhibitors. The disclosure provides for natural, synthetic or semi-synthetic trypsin inhibitors.

Trypsin inhibitors can be derived from a variety of animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678. A trypsin inhibitor can also be an arginine or lysine mimic or other synthetic compound: for example arylguanidine, benzamidine, 3,4-dichloroisocoumarin, diisopropylfluorophosphate, gabexate mesylate, phenylmethanesulfonyl fluoride, or substituted versions or analogs thereof. In certain embodiments, trypsin inhibitors comprise a covalently modifiable group, such as a chloroketone moiety, an aldehyde moiety, or an epoxide moiety. Other examples of trypsin inhibitors are aprotinin, camostat and pentamidine.

As used herein, an arginine or lysine mimic is a compound that is capable of binding to the $P^1$ pocket of trypsin and/or interfering with trypsin active site function. The arginine or lysine mimic can be a cleavable or non-cleavable moiety.

In one embodiment, the trypsin inhibitor is derived from soybean. Trypsin inhibitors derived from soybean (*Glycine max*) are readily available and are considered to be safe for human consumption. They include, but are not limited to, SBTI, which inhibits trypsin, and Bowman-Birk inhibitor, which inhibits trypsin and chymotrypsin. Such trypsin inhibitors are available, for example from Sigma-Aldrich, St. Louis, MO, USA.

It will be appreciated that the pharmaceutical composition according to the embodiments may further comprise one or more other trypsin inhibitors.

As stated above, a trypsin inhibitor can be an arginine or lysine mimic or other synthetic compound. In certain embodiments, the trypsin inhibitor is an arginine mimic or a lysine mimic, wherein the arginine mimic or lysine mimic is a synthetic compound.

Certain trypsin inhibitors include compounds of formula:

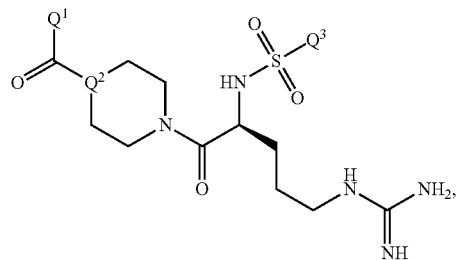

wherein:

$Q^1$ is selected from —O-$Q^4$ or -$Q^4$-COOH, where $Q^4$ is $C_1$-$C_4$ alkyl;

$Q^2$ is N or CH; and $Q^3$ is aryl or substituted aryl.

Certain trypsin inhibitors include compounds of formula:

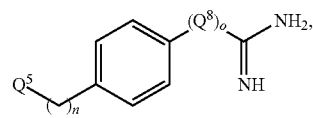

wherein:

$Q^5$ is —C(O)—COOH or —NH-$Q^6$-$Q^7$-$SO_2$—$C_6H_5$, where $Q^6$ is —$(CH_2)_p$—COOH;

$Q^7$ is —$(CH_2)_r$—$C_6H_5$;

$Q^8$ is NH;

n is a number from zero to two;

o is zero or one;

p is an integer from one to three; and r is an integer from one to three.

Certain trypsin inhibitors include compounds of formula:

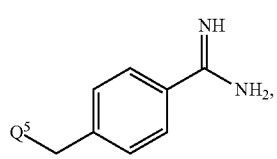

wherein:

$Q^5$ is —C(O)—COOH or —NH-$Q^6$-$Q^7$-$SO_2$—$C_6H_5$, where $Q^6$ is —$(CH_2)_p$—COOH;

$Q^7$ is —$(CH_2)_r$—$C_6H_5$; and p is an integer from one to three; and r is an integer from one to three.

Certain trypsin inhibitors include the following:

| Compound 101 | 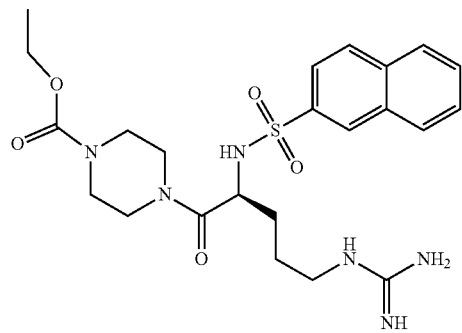 [SMILES: CCOC(=O)N1CCN(C(=O)[C@H](CCCNC(=N)N)NS(=O)(=O)c2ccc3ccccc3c2)CC1] | (S)-ethyl 4-(5-guanidino-2-(naphthalene-2-sulfonamido)pentanoyl)piperazine-1-carboxylate |
| --- | --- | --- |
| Compound 102 | 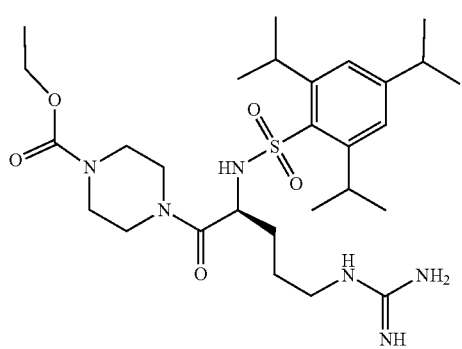 [SMILES: CCOC(=O)N1CCN(C(=O)[C@H](CCCNC(=N)N)NS(=O)(=O)c2c(C(C)C)cc(C(C)C)cc2C(C)C)CC1] | (S)-ethyl 4-(5-guanidino-2-(2,4,6-triisopropylphenylsulfonamido)pentanoyl)piperazine-1-carboxylate |
| Compound 103 | 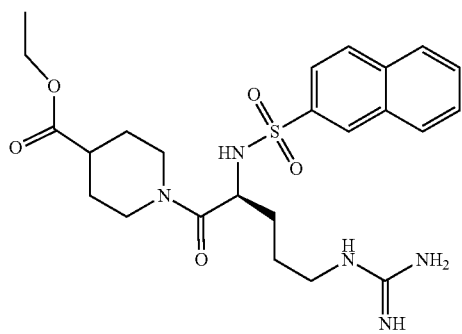 [SMILES: CCOC(=O)C1CCN(C(=O)[C@H](CCCNC(=N)N)NS(=O)(=O)c2ccc3ccccc3c2)CC1] | (S)-ethyl 1-(5-guanidino-2-(naphthalene-2-sulfonamido)pentanoyl)piperidine-4-carboxylate |
| Compound 104 | 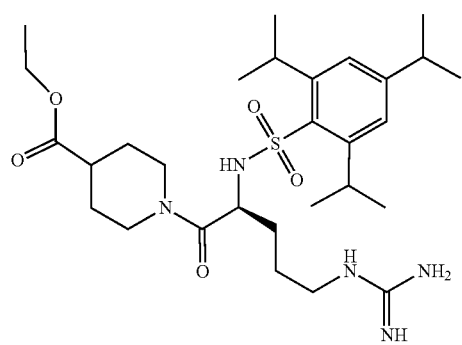 [SMILES: CCOC(=O)C1CCN(C(=O)[C@H](CCCNC(=N)N)NS(=O)(=O)c2c(C(C)C)cc(C(C)C)cc2C(C)C)CC1] | (S)-ethyl 1-(5-guanidino-2-(2,4,6-triisopropylphenylsulfonamido)pentanoyl)piperidine-4-carboxylate |

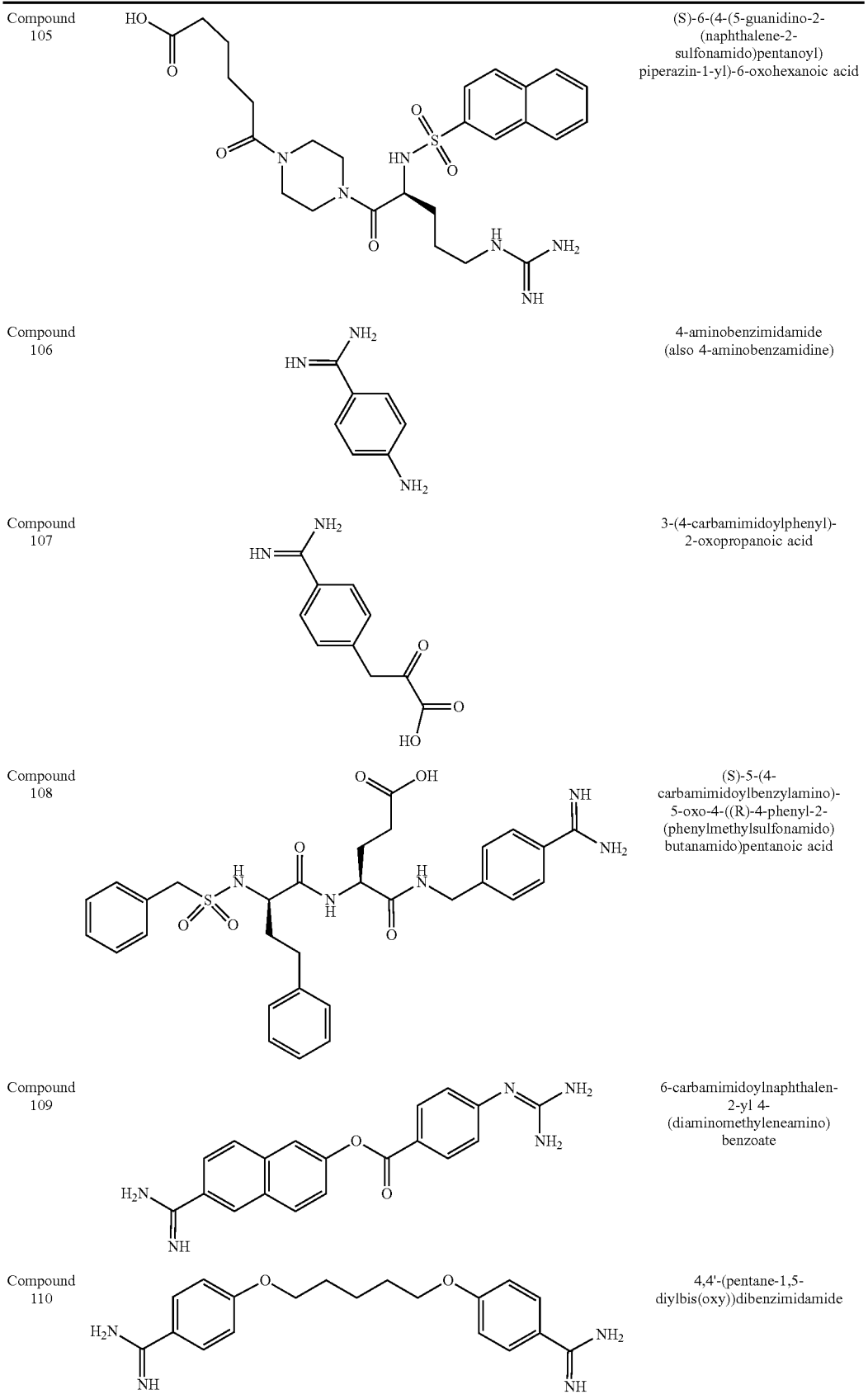

| | | |
|---|---|---|
| Compound 105 | | (S)-6-(4-(5-guanidino-2-(naphthalene-2-sulfonamido)pentanoyl)piperazin-1-yl)-6-oxohexanoic acid |
| Compound 106 | | 4-aminobenzimidamide (also 4-aminobenzamidine) |
| Compound 107 | | 3-(4-carbamimidoylphenyl)-2-oxopropanoic acid |
| Compound 108 | | (S)-5-(4-carbamimidoylbenzylamino)-5-oxo-4-((R)-4-phenyl-2-(phenylmethylsulfonamido)butanamido)pentanoic acid |
| Compound 109 | | 6-carbamimidoylnaphthalen-2-yl 4-(diaminomethyleneamino)benzoate |
| Compound 110 | | 4,4'-(pentane-1,5-diylbis(oxy))dibenzimidamide |

A description of methods to prepare Compound 101, Compound 102, Compound 103, Compound 104, Compound 105, Compound 107, and Compound 108 is provided in PCT International Publication Number WO 2010/045599A1, published 22 Apr. 2010, which is incorporated herein by reference in its entirety. Compound 106, Compound 109, and Compound 110 are commercially available, e.g., from Sigma-Aldrich, St. Louis, MO, USA.

In certain embodiments, the trypsin inhibitor is SBTI, BBSI, Compound 101, Compound 106, Compound 108, Compound 109, or Compound 110. In certain embodiments, the trypsin inhibitor is camostat.

In certain embodiments, the trypsin inhibitor is a compound of formula T-I:

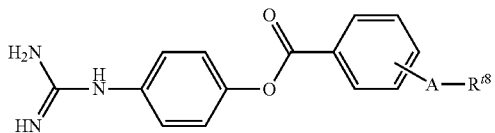

(T-I)

wherein

A represents a group of the following formula:

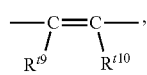

$R^{t9}$ and $R^{t10}$ each represents independently a hydrogen atom or a $C_{1-4}$ alkyl group, $R^{t8}$ represents a group selected from the following formulae:

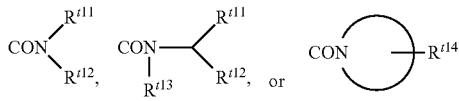

wherein $R^{t11}$, $R^{t12}$ and $R^{t13}$ each represents independently
(1) a hydrogen atom,
(2) a phenyl group,
(3) a $C_{1-4}$ alkyl group substituted by a phenyl group,
(4) a $C_{1-10}$ alkyl group,
(5) a $C_{1-10}$ alkoxyl group,
(6) a $C_{2-10}$ alkenyl group having 1 to 3 double bonds,
(7) a $C_{2-10}$ alkynyl group having 1 to 2 triple bonds,
(8) a group of formula: $R^{t15}$—C(O)X$R^{t16}$,
wherein $R^{t15}$ represents a single bond or a $C_{1-8}$ alkylene group,
X represents an oxygen atom or an NH-group, and
$R^{t16}$ represents a hydrogen atom, a $C_{1-4}$ alkyl group, a phenyl group or a $C_{1-4}$ alkyl group substituted by a phenyl group, or
(9) a $C_{3-7}$ cycloalkyl group;
the structure

represents a 4-7 membered monocyclic hetero-ring containing 1 to 2 nitrogen or oxygen atoms, $R^{t14}$ represents a hydrogen atom, a $C_{1-4}$ alkyl group substituted by a phenyl group or a group of formula: COO$R^{t17}$, wherein $R^{t17}$ represents a hydrogen atom, a $C_{1-4}$ alkyl group or a $C_{1-4}$ alkyl group substituted by a phenyl group;

provided that $R^{t11}$, $R^{t12}$ and $R^{t13}$ do not represent simultaneously hydrogen atoms;

or nontoxic salts, acid addition salts or hydrates thereof.

In certain embodiments, the trypsin inhibitor is a compound selected from the following:

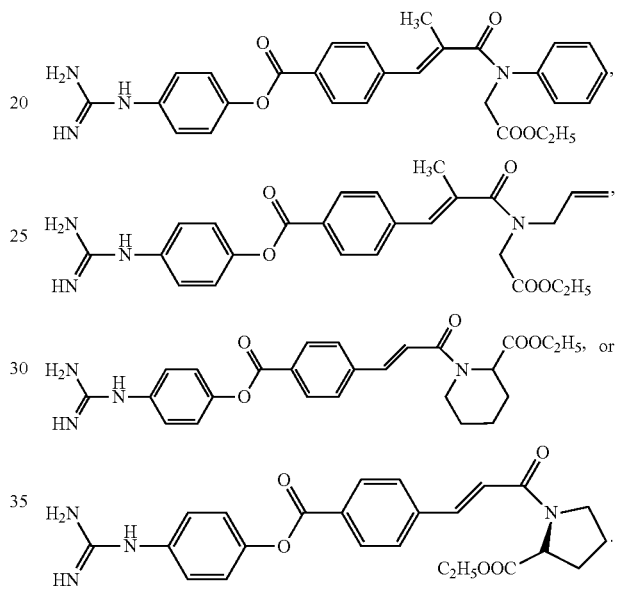

In certain embodiments, the trypsin inhibitor is a compound of formula T-II:

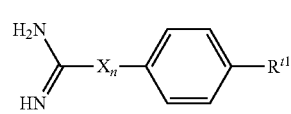

(T-II)

wherein

X is NH;

n is zero or one; and $R^{t1}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH$_2$)$_m$—C(O)—O—(CH$_2$)$_m$—C(O)—N—$R^{n1}R^{n2}$, wherein each m is independently zero to 2; and $R^{n1}$ and $R^{n2}$ are independently selected from hydrogen and $C_{1-4}$ alkyl.

In certain embodiments, in formula T-II, $R^{t1}$ is guanidino or amidino.

In certain embodiments, in formula T-II, $R^{t1}$ is —(CH$_2$)$_m$—C(O)—O—(CH$_2$)$_m$—C(O)—N—$R^{n1}R^{n2}$, wherein m is one and $R^{n1}$ and $R^{n2}$ are methyl.

In certain embodiments, the trypsin inhibitor is a compound of formula T-III:

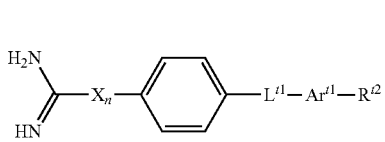

(T-III)

wherein

X is NH;

n is zero or one;

$L^{t1}$ is selected from —C(O)—O—; —O—C(O)—; —O—(CH$_2$)$_m$—O—; —OCH$_2$—Ar$^{t2}$—CH$_2$O—; —C(O)—NR$^{t3}$—; and —NR$^{t3}$—C(O)—;

$R^{t3}$ is selected from hydrogen, C$_{1-6}$ alkyl, and substituted C$_{1-6}$ alkyl;

Ar$^{t1}$ and Ar$^{t2}$ are independently a substituted or unsubstituted aryl group;

m is a number from 1 to 3; and $R^{t2}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH$_2$)$_m$—C(O)—O—(CH$_2$)$_m$—C(O)—N—R$^{n1}$R$^{n2}$, wherein each m is independently zero to 2; and R$^{n1}$ and R$^{n2}$ are independently selected from hydrogen and C$_{1-4}$ alkyl.

In certain embodiments, in formula T-III, $R^{t2}$ is guanidino or amidino.

In certain embodiments, in formula T-III, $R^{t2}$ is —(CH$_2$)$_m$—C(O)—O—(CH$_2$)$_m$—C(O)—N—R$^{n1}$R$^{n2}$, wherein m is one and R$^{n1}$ and R$^{n2}$ are methyl.

In certain embodiments, the trypsin inhibitor is a compound of formula T-IV:

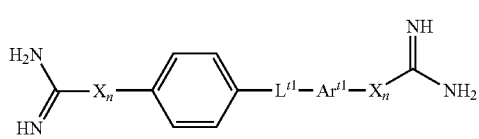

(T-IV)

wherein each X is NH;

each n is independently zero or one;

$L^{t1}$ is selected from —C(O)—O—; —O—C(O)—; —O—(CH$_2$)$_m$—O—; —OCH$_2$—Ar$^{t2}$—CH$_2$O—; —C(O)—NR$^{t3}$—; and —NR$^{t3}$—C(O)—;

$R^{t3}$ is selected from hydrogen, C$_{1-6}$ alkyl, and substituted C$_{1-6}$ alkyl;

Ar$^{t1}$ and Ar$^{t2}$ are independently a substituted or unsubstituted aryl group; and m is a number from 1 to 3.

In certain embodiments, in formula T-IV, Ar$^{t1}$ or Ar$^{t2}$ is phenyl.

In certain embodiments, in formula T-IV, Ar$^{t1}$ or Ar$^{t2}$ is naphthyl.

In certain embodiments, the trypsin inhibitor is Compound 109.

In certain embodiments, the trypsin inhibitor is

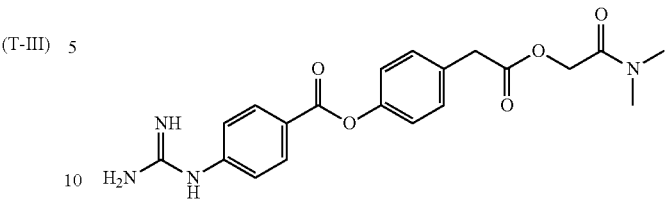

In certain embodiments, the trypsin inhibitor is Compound 110 or a bis-arylamidine variant thereof; see, for example, J. D. Geratz, M. C.-F. Cheng and R. R. Tidwell (1976) J Med. Chem. 19, 634-639.

It is to be appreciated that the invention also includes inhibitors of other enzymes involved in protein assimilation that can be used in combination with a methadone prodrug described herein to attenuate release of methadone from the prodrug.

Pharmaceutical Compositions and Methods of Use

As disclosed herein, the embodiments provide a composition, which comprises a methadone prodrug as described herein. The pharmaceutical composition according to the embodiments can further comprise a pharmaceutically acceptable carrier. The composition is conveniently formulated as described above in a form suitable for oral (including buccal and sublingual) administration, for example as a tablet, capsule, thin film, powder, suspension, solution, syrup, dispersion or emulsion. The composition can contain components conventional in pharmaceutical preparations, e.g. one or more carriers, binders, lubricants, excipients (e.g., to impart controlled release characteristics), pH modifiers, sweeteners, bulking agents, coloring agents or further active agents.

Patients can be humans, and also other mammals, such as livestock, zoo animals and companion animals, such as a cat, dog or horse.

In another aspect, the embodiments provide a pharmaceutical composition as described hereinabove for use in the treatment of pain. The pharmaceutical composition according to the embodiments is useful, for example, in the treatment of a patient suffering from, or at risk of suffering from, pain. Accordingly, the present disclosure provides methods of treating or preventing pain in a subject, the methods involving administering to the subject a disclosed composition. The present disclosure provides for a disclosed composition for use in therapy or prevention or as a medicament. The present disclosure also provides the use of a disclosed composition for the manufacture of a medicament, especially for the manufacture of a medicament for the treatment or prevention of pain.

The compositions of the present disclosure can be used in the treatment or prevention of pain including, but not limited to include, acute pain, chronic pain, neuropathic pain, acute traumatic pain, arthritic pain, osteoarthritic pain, rheumatoid arthritic pain, muscular skeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, muscular skeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain.

The present disclosure also provides use of a methadone prodrug as described herein in the treatment of pain. The present disclosure also provides use of a methadone prodrug as described herein in the prevention of pain.

The present disclosure provides use of a methadone prodrug as described herein in the manufacture of a medicament for treatment of pain. The present disclosure provides use of a methadone prodrug as described herein in the manufacture of a medicament for prevention of pain.

In another aspect, the embodiments provide a method of treating pain in a patient in need thereof, which comprises administering an effective amount of a pharmaceutical composition as described hereinabove. In another aspect, the embodiments provide a method of preventing pain in a patient in need thereof, which comprises administering an effective amount of a pharmaceutical composition as described hereinabove.

The amount of composition disclosed herein to be administered to a patient to be effective (i.e. to provide blood levels of methadone sufficient to be effective in the treatment or prophylaxis of pain) will depend upon the bioavailability of the particular composition, the susceptibility of the particular composition to enzyme activation in the gut, as well as other factors, such as the species, age, weight, sex, and condition of the patient, manner of administration and judgment of the prescribing physician. If the composition also comprises a trypsin inhibitor, the amount of composition disclosed herein to be administered to a patient would also depend on the amount and potency of trypsin inhibitor present in the composition. In general, the composition dose can be such that the methadone prodrug is in the range of from 0.01 milligrams prodrug per kilogram to 20 milligrams prodrug per kilogram (mg/kg) body weight.

For example, a composition comprising a methadone prodrug as described herein can be administered at a dose equivalent to administering free methadone in the range of from 0.02 to 0.5 mg/kg body weight or 0.01 mg/kg to 10 mg/kg body weight or 0.01 to 2 mg/kg body weight. In one embodiment, the composition can be administered at a dose such that the level of methadone achieved in the blood is in the range of from 0.5 ng/ml to 10 ng/ml.

Orally Administered Controlled-Release Compositions of Nafamostat or Pharmaceutically Acceptable Salt Thereof As summarized above, aspects of the present disclosure include oral compositions of nafamostat or a pharmaceutically acceptable salt thereof that provides for controlled release of nafamostat or pharmaceutically acceptable salt thereof to a subject for an extended period of time. As described herein, the compound nafamostat refers to 6-carbamimidoylnaphthalen-2-yl 4-(diaminomethyleneamino) benzoate:

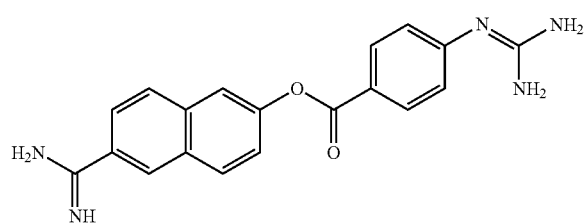 [SMILES: N=C(N)c1ccc2cc(OC(=O)c3ccc(N=C(N)N)cc3)ccc2c1]

Nafamostat (6-carbamimidoylnaphthalen-2-yl 4-(diaminomethyleneamino)benzoate)

In some embodiments, compositions include nafamostat free base. In other embodiments, compositions include a pharmaceutically acceptable salt of nafamostat. In embodiments, "salts" of nafamostat may include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In certain embodiments, the salt of nafamostat is nafamostat mesylate.

In embodiments, oral compositions of nafamostat or a pharmaceutically acceptable salt thereof provide post administration-activated, controlled release of nafamostat or pharmaceutically acceptable salt thereof to a subject for an extended period of time. In some embodiments, the controlled release composition provides for the sustained release of one or more doses of nafamostat or pharmaceutically acceptable salt thereof to the subject. In some instances, the sustained release of nafamostat is a zero-order sustained release. In other instances, the sustained release of nafamostat is a first-order sustained release. For example, controlled release nafamostat compositions may provide for sustained release of 0.000001 µg/min or more of the nafamostat, such as 0.000005 µg/min or more, such as 0.00001 µg/min or more, such as 0.0005 µg/min or more, such as 0.001 µg/min or more, such as 0.005 µg/min or more, such as 0.01 µg/min or more, such as 0.05 µg/min or more, such as 0.1 µg/min or more, such as 0.5 µg/min or more, such as 1 µg/min or more, such as 5 µg/min or more, such as 10 µg/min or more, such as 100 µg/min or more and including sustained release of 250 µg/min or more of nafamostat or pharmaceutically acceptable salt thereof.

In some embodiments, controlled release compositions of nafamostat provide for delayed immediate release of nafamostat or pharmaceutically acceptable salt thereof. The term "delayed immediate release" is used herein to refer to the timing that nafamostat or pharmaceutically acceptable salt thereof is released after administration, where an amount of the nafamostat is released from the composition at a predetermined period of time after administration to the subject. In some instances, delayed immediate release compositions of nafamostat are formulated to release 50% or more of nafamostat or pharmaceutically acceptable salt thereof at the predetermined period of time, such as formulated to release 60% or more, such as 70% or more, such as 80% or more, such as 90% or more, such as 95% or more, such as 97% or more, such as 99% or more and including being formulated to release all of the nafamostat in the composition (100%) at a predetermined period of time after administration of the composition to the subject. The period of time of the delayed release may vary, where in some instances, compositions of interest are formulated to release the nafamostat or pharmaceutically acceptable salt thereof 5 minutes or more after orally administering the composition to the subject, such as 10 minutes or more, such as 15 minutes or more, such as 20 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 10 hours or more, such as 12 hours or more, such as 18 hours or more and including 24 hours or more after orally administering the composition to the subject.

In certain embodiments, oral compositions of nafamostat or a pharmaceutically acceptable salt thereof are formulated as a plurality of controlled release beads where each bead includes a core, an active agent layer having nafamostat or a pharmaceutically acceptable salt thereof and a controlled release layer having one or more polymers formulated in an amount sufficient to provide for controlled release of the nafamostat or pharmaceutically acceptable salt thereof. In some embodiments, the size of the beads ranges from 0.001 mm to 5 mm in diameter, such as from 0.005 mm to 4.5 mm, such as from 0.01 mm to 4 mm, such as from 0.05 mm to 3.5 mm, such as from 0.1 mm to 3 mm, such as from 0.5 mm to 2.5 mm, such as from 1 mm to 3 mm and including from 0.2 mm and 3 mm in diameter.

In some instances, the core is formed from an inert substance. Such substances include a cellulose polymer, silicon dioxide, a sugar, starch, or a combination thereof. The sugar can be glucose, sucrose, lactose, mannitol, xylitol, sorbitol, or a combination thereof. In some embodiments, the core may be formed from microcrystalline cellulose, Cellets® cores, such as Cellets® 100, Cellets® 200, Cellets® 350, Cellets® 500, Cellets® 700, or Cellets® 1000 (Glatt Air Techniques Inc., Ramsey N.J.). In other embodiments, the core is prepared de novo, for example by preparing a polymer mixture, extruding the mixture, and spheronizing the extruded mixture to form spherical or semi-spherical beads. In some embodiments, the beads are swellable such that their exposure to aqueous media causes them to swell and release the active ingredient rapidly and efficiently. In some embodiments, the core comprises between about 10% to about 50% of the total weight of the finally-formulated bead. In some embodiments, the core comprises between about 15% to about 40% of the total weight of the finally-formulated bead. In some embodiments, the core comprises between about 20% to about 30% of the total weight of the finally-formulated bead. In some embodiments, the core comprises about 20% of the total weight of the finally-formulated bead. In some embodiments, the core comprises about 25% of the total weight of the finally-formulated bead. In certain embodiments, the core is a microcrystalline cellulose (MCC) bead, such as a Cellets microcrystalline cellulose bead.

In some embodiments, an active agent layer having nafamostat or a pharmaceutically acceptable salt thereof (e.g., nafamostat or nafamostat mesylate) is formed on the core. In some embodiments, the active agent layer comprises between about 1% to about 50% of the total weight of the bead. In some embodiments, the active agent layer comprises between about 2% to about 40% of the total weight of the bead. In some embodiments, the active agent layer comprises between about 5% to about 30% of the total weight of the bead. In some embodiments, the active agent layer comprises between about 7% to about 25% of the total weight of the bead. In some embodiments, the active agent layer comprises between about 8% to about 15% of the total weight of the bead. In some embodiments, the active agent layer comprises about 8% of the total weight of the bead. In some embodiments, the active agent layer comprises about 10% of the total weight of the bead. In some embodiments, the active agent layer comprises about 12% of the total weight of the bead. In some embodiments, the active agent layer comprises about 15% of the total weight of the bead.

In some embodiments, the application of the active agent layer causes a weight gain of between about 1% to about 50% of the weight prior to the application of the active agent layer. Thus, for example, if the weight of the core prior to the application of the active agent layer is X, then after the application of the active agent layer, the weight of each bead is 1.01×, if the weight gain is 1%, or the weight of each bead is 1.5×, if the weight gain is 50%. In some embodiments, the weight gain is between about 5% to about 45%. In some embodiments, the weight gain is between about 5% to about 40%. In some embodiments, the weight gain is between about 5% to about 35%. In some embodiments, the weight gain is between about 5% to about 30%. In some embodiments, the weight gain is between about 10% to about 25%.

Nafamostat or a pharmaceutically acceptable salt thereof may be present in the active agent layer of each bead in an amount of 0.000001 mg or more, such as 0.00001 mg or more, such as 0.0001 mg or more, such as 0.001 mg or more, such as 0.01 mg or more, such as 0.1 mg or more, such as 0.5 mg or more, such as 1 mg or more and including 2 mg or more. In some embodiments, the drug loading of nafamostat or pharmaceutically acceptable salt thereof of each bead is from 1% w/w to 25% w/w, such as from 2% w/w to 24% w/w, such as from 3% w/w to 23% w/w, such as from 4% w/w to 22% w/w, such as from 5% w/w to 21% w/w, such as from 6% w/w to 20% w/w, such as from 7% w/w to 19% w/w, such as from 8% w/w to 18% w/w, such as from 9% w/w to 15% w/w and including from 11% w/w to 13% w/w. As described in greater detail below, oral compositions of nafamostat according to embodiments of the present disclosure may include 10 mg or more of nafamostat or a pharmaceutically acceptable salt thereof, such as 15 mg or more, such as 20 mg or more, such as 25 mg or more, such as 30 mg or more, such as 35 mg or more, such as 40 mg or more, such as 45 mg or more, such as 50 mg or more, such as 60 mg or more, such as 70 mg or more, such as 80 mg or more, such as 90 mg or more, such as 100 mg or more, such as 150 mg or more and including 200 mg or more.

In addition to nafamostat or a pharmaceutically acceptable salt thereof, the active agent layer can further contain a binder. The binder can be a pharmaceutically acceptable polymer, such as a hydroxyalkyl cellulose, maltodextrin, cellulose acetate phthalate, sucrose, modified starch, a salt of alginic acid, soluble gums, carrageenan, an alkyl cellulose, corn starch, polyethylene glycol, polyethylene oxide, hydroxypropylmethylcellulose phthalate, insoluble gums, polymethacrylate, polyvinylpyrrolidone (PVP) or polyvinylpolypyrrolidone (PVPP), polyvinyl alcohol, shellac, and polyvinyl acetate phthalate or any combination thereof. A hydroxyalkyl cellulose can be hydroxypropyl cellulose, hydroxyethyl cellulose, hydroxypropylmethyl cellulose, or any combination thereof. An alkyl cellulose can be cellulose, ethyl cellulose, ethylmethyl cellulose, or any combination thereof. In certain embodiments, the binder comprises hydroxypropyl methylcellulose.

In some embodiments, the active agent layer containing nafamostat or a pharmaceutically acceptable salt thereof may further include a de-tackifier or glidant, such as talc, a monoglyceride, a diglyceride, glyceryl monostearate, calcium stearate, and magnesium stearate.

In other embodiments, the active agent layer containing the nafamostat or a pharmaceutically acceptable salt thereof includes a lipid excipient, such as glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl monooleate, medium chain mono- & diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. Glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene myristyl ether, polyoxypropylene 10 cetostearyl ether, palm kernelamide diethanolamide, triglycerol mono-oleate, sasol products, hydrogenated coco-glycerides, cetyl palmitate, trimyristin, tripalmitin, tristearin, hydrogenated palm oil, glyceryl monostearate, glyceryl stearate, cetearyl alcohol, cetyl alcohol, capric triglyceride, acetylated glycerides, glyceryl cocoate, and polyethylene glycol or combinations thereof.

In certain embodiments, the active agent layer containing nafamostat or a pharmaceutically acceptable salt thereof includes nafamostat or a pharmaceutically acceptable salt thereof and hydroxypropyl methylcellulose.

In some embodiments, the controlled release beads include a controlled release layer having one or more polymers formulated to provide for controlled release of the nafamostat or pharmaceutically acceptable salt thereof. The polymers are pharmaceutically acceptable and suitable for providing controlled release of nafamostat over an extended period of time as described above. In some instances, polymers of the controlled release layer include but are not limited to cellulose ethers such as Ethocel™, acrylate polymers, methacrylate polymers, neutral (meth)acrylate-based polymers such as Eudragit™ NE 30D, ionic (meth)acrylate-based polymers such as Eudragit™ RS or RL, polyvinyl acetate, or combinations thereof. In certain embodiments, polymers of the controlled release layer are stabilized with polyvinylpyrrolidone (PVP), such as Kollicoat™ SR.

In some embodiments, the controlled release layer includes an acrylate copolymer. Acrylate copolymers can include copolymers of various monomers, such as "soft" monomers, "hard" monomers or "functional" monomers. The acrylate copolymers can be composed of a copolymer including a bipolymer (i.e., made with two monomers), a terpolymer (i.e., made with three monomers), or a tetrapolymer (i.e., made with four monomers), or copolymers having greater numbers of monomers. The acrylate copolymers may be crosslinked or non-crosslinked. The polymers can be cross-linked by known methods to provide the desired polymers. The monomers from of the acrylate copolymers may include two or more components selected from the group including acrylic acids, alkyl acrylates, methacrylates, copolymerizable secondary monomers or monomers with functional groups. Monomers ("soft" and "hard" monomers) may be methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. In certain embodiments, the controlled release layer includes a methacrylate acrylate copolymer or a mixture of two or more methacrylate acrylate copolymers. In some instances, methacrylate acrylate copolymers of interest are substantially the same as Eudragit™ acrylate copolymers, as described below. In certain instances, the controlled release layer includes an acrylate copolymer that is substantially the same as Eudragit RS. In certain instances, the controlled release layer includes an acrylate copolymer that is substantially the same as Eudragit RL. In certain instances, the controlled release layer includes a first acrylate copolymer that is substantially the same as Eudragit RS and a second acrylate copolymer that is substantially the same as Eudragit RL.

In some embodiments, the controlled release layer includes two different polymers (e.g., two different acrylate copolymers). In some instances, the first polymer is present in the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight. In some instances, the second polymer is present in the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight.

The ratio by weight of the first polymer (e.g., first acrylate copolymer) to the second polymer (e.g., second acrylate copolymer) in the controlled release layer to may vary, such as from 1:99 to 99:1, such as from 5:95 to 95:5, such as from 10:90 to 90:10, such as from 20:80 to 80:20, such as from 30:70 to 70:30, such as from 40:60 to 60:40 and including where the ratio by weight of the first polymer to the second polymer in the controlled release layer is 50:50.

In some instances, the controlled release layer includes a copolymer of ethylacrylate, methyl methacrylate and chlorotrimethyl-aminonioethyl methacrylate. In certain instances, the polymer is poly(ethylacrylate, methyl-methacrylate and chlorotrimethyl-ammonioethyl methacrylate) containing quaternary ammonium groups. For example, the acrylate copolymer may be a combination of: 1) poly(ethylacrylate, methyl-methacrylate and chlorotrimethyl-ammonioethyl methacrylate) containing about 50 mEq of quaternary ammonium groups per 100 g of polymer (hereinafter, "acrylate copolymer A"; where in some instances, acrylate copolymer A is substantially the same as Eudragit™ RL) and 2) poly(ethylacrylate, methyl-methacrylate and chlorotrimethyl-ammonioethyl methacrylate) containing about 25 mEq of quaternary ammonium groups per 100 g of polymer (hereinafter, "acrylate copolymer B"; where in some instances, acrylate copolymer B is substantially the same as Eudragit™ RS). In some instances, the acrylate copolymer A is present in the polymer of the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight. In some instances, acrylate copolymer B is present in the polymer of the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight.

The ratio by weight of acrylate copolymer A to acrylate copolymer B in the controlled release layer to may vary, such as from 1:99 to 99:1, such as from 5:95 to 95:5, such as from 10:90 to 90:10, such as from 20:80 to 80:20, such as from 30:70 to 70:30, such as from 40:60 to 60:40 and including where the ratio by weight of the acrylate copolymer A to acrylate copolymer B in the controlled release layer is 50:50.

In certain cases, the polymer of the controlled release layer comprises 20% by weight acrylate copolymer B and 80% by weight acrylate copolymer A.

In certain cases, the polymer of the controlled release layer comprises 50% by weight acrylate copolymer B and 50% by weight acrylate copolymer A.

In certain cases, the polymer of the controlled release layer comprises 80% by weight acrylate copolymer B and 20% by weight acrylate copolymer A.

In certain cases, the polymer of the controlled release layer comprises 100% by weight acrylate copolymer B.

In certain cases, the polymer of the controlled release layer comprises 100% by weight acrylate copolymer A.

In certain cases, the polymer of the controlled release layer comprises 93% by weight acrylate copolymer B and 7% by weight acrylate copolymer A.

In certain cases, the polymer of the controlled release layer comprises 87% by weight acrylate copolymer B and 13% by weight acrylate copolymer A.

Certain non-limiting examples of compositions of nafamostat mesylate are provided in Tables 1 and 2 below:

TABLE 1

Composition of Drug Product, Formulations I to IV

| Component | Amount Dose Unit (mg) | | | |
| --- | --- | --- | --- | --- |
| | Formulation I (95:5 RS:RL) | Formulation II (80:20 RS:RL) | Formulation III (80:20 RS:RL) | Formulation IV (95:5 RS:RL) |
| Nafamostat mesylate | 100 | 100 | 1 | 1 |
| Hypromellose capsule | one unit | one unit | one unit | one unit |
| Microcrystalline cellulose spheres | 526.4 | 526.4 | 5.264 | 5.264 |
| Hypromellose | 100 | 100 | 1 | 1 |
| Ammonio methacrylate copolymers type A (Eudragit RL) | 4.5 | 18.1 | 0.181 | 0.045 |
| Ammonio methacrylate copolymers type B (Eudragit RS) | 86.2 | 72.6 | 0.726 | 0.862 |
| Triethyl citrate | 9.1 | 9.1 | 0.091 | 0.091 |
| Talc | 45.4 | 45.4 | 0.454 | 0.454 |
| TOTAL | 871.6 | 871.6 | 8.72 | 8.72 |

Formulation I = High Dose, Slow Release Rate
Formulation II = High Dose, Fast Release Rate
Formulation III = Low Dose, Fast Release Rate
Formulation IV = Low Dose, Slow Release Rate

TABLE 2

Nafamostat Controlled Release Bead Formulations

|  | Formulation V (100:0 RS:RL) | Formulation VI (87:13 RS:RL) | Formulation VII (100:0 RS:RL) | Formulaion VIII (93:7 RS:RL) |
|---|---|---|---|---|
| Core | Microcrystalline Cellulose Spheres 63.01% w/w | Microcrystalline Cellulose Spheres 60.3865% w/w | Microcrystalline Cellulose Spheres 60.39% w/w | Microcrystalline Cellulose Spheres 60.3865% w/w |
| Active Agent Layer | Nafamostat 11.97% w/w Hydroxypropyl methylcellulose 11.97% w/w | Nafamostat 11.4734% w/w Hydroxypropyl methylcellulose 11.4734% w/w | Nafamostat 11.47% w/w Hydroxypropyl methylcellulose 11.47% w/w | Nafamostat 11.4734% w/w Hydroxypropyl methylcellulose 11.4734% w/w |
| Controlled Release Layer | Ammonio methacrylate copolymers type B (Eudragit RSPO) 8.15% w/w Ammonio methacrylate copolymers type A (Eudragit RLPO) 0.0% w/w Triethyl Citrate 0.82% w/w Talc 4.08% w/w | Ammonio methacrylate copolymers type B (Eudragit RSPO) 9.0625% w/w Ammonio methacrylate copolymers type A (Eudragit RLPO) 1.3542% w/w Triethyl Citrate 1.0417% w/w Talc 5.2083% w/w | Ammonio methacrylate copolymers type B (Eudragit RSPO) 10.42% w/w Ammonio methacrylate copolymers type A (Eudragit RLPO) 0.0% w/w Triethyl Citrate 1.04% w/w Talc 5.21% w/w | Ammonio methacrylate copolymers type B (Eudragit RSPO) 9.6875% w/w Ammonio methacrylate copolymers type A (Eudragit RLPO) 0.7292% w/w Triethyl Citrate 10.417% w/w Talc 5.2083% w/w |

In some embodiments, the controlled release layer further includes mold release agents, such as glycerol monostearate. In some embodiments, the controlled release layer also contains one or more plasticizers. In some embodiments, the plasticizer is selected from the group consisting of a phthalate-based plasticizer, a trimellitate, an adipate-based plasticizer, a sebacate-based plasticizer, an organophosphate, a maleate, a sulfonamide, a glycols or polyether, an acetylated monoglyceride, and an alkyl citrate. In certain embodiments, the sebacate-based plasticiser is dibutyl sebacate (DBS). In certain embodiments, the plasticizer is triethyl citrate. In some embodiments, the plasticizer is present in between about 1% to about 20% of the weight of the controlled release layer, or between about 5% to about 15% by weight, or between about 7% to about 10% by weight. In certain embodiments, the controlled release layer can further contain a flavouring agent. In certain cases, the active agent layer and/or the controlled release layer comprise magnesium silicate.

In certain embodiments, the plurality of controlled release beads includes an immediate release layer of nafamostat or pharmaceutically acceptable salt thereof that is coated on top of the controlled release layer. In some instances, the immediate release layer of nafamostat or pharmaceutically acceptable salt thereof is formulated to release 50% or more of the nafamostat or pharmaceutically acceptable salt thereof within 10 minutes or less of administration of the composition to the subject, such as 60% or more, such as 75% or more, such as 90% or more, such as 95% or more and including 99% or more within 10 minutes or less of administration of the composition to the subject. In certain instances, the immediate release layer of nafamostat or pharmaceutically acceptable salt thereof is formulated to release all (i.e., 100%) of the nafamostat or pharmaceutically acceptable salt thereof within 10 minutes or less of administration of the composition to the subject. In certain instances, the immediate release layer of nafamostat or pharmaceutically acceptable salt thereof is formulated to release 50% or more of nafamostat or a pharmaceutically acceptable salt thereof immediately after administration of the composition to the subject, such as 60% or more, such as 75% or more, such as 90% or more, such as 95% or more and including 99% or more immediately after administration of the composition to the subject.

The amount of nafamostat or a pharmaceutically acceptable salt thereof present in the immediate release layer of each bead may be 0.000001 mg or more, such as 0.00001 mg or more, such as 0.0001 mg or more, such as 0.001 mg or more, such as 0.01 mg or more, such as 0.1 mg or more, such as 0.5 mg or more, such as 1 mg or more and including 2 mg or more. In some embodiments, the drug loading of nafamostat or pharmaceutically acceptable salt thereof in the immediate release layer of each bead is from 1% w/w to 25% w/w, such as from 2% w/w to 24% w/w, such as from 3% w/w to 23% w/w, such as from 4% w/w to 22% w/w, such as from 5% w/w to 21% w/w, such as from 6% w/w to 20% w/w, such as from 7% w/w to 19% w/w, such as from 8% w/w to 18% w/w, such as from 9% w/w to 15% w/w and including from 11% w/w to 13% w/w.

The oral composition of controlled release nafamostat or pharmaceutically acceptable salt thereof may be formulated in any convenient form suitable for oral (including buccal and sublingual) administration for example as a tablet, capsule, powder, suspension, dispersion or emulsion. The composition can contain components conventional in pharmaceutical preparations, e.g., one or more carriers, binders, lubricants, excipients (e.g., to impart controlled release characteristics), pH modifiers, sweeteners, bulking agents, coloring agents or further active agents as described above. The pharmaceutical composition according to the embodiments can further comprise a pharmaceutically acceptable carrier.

The amount of nafamostat or a pharmaceutically acceptable salt thereof in a unit composition, for example, a capsule of the controlled release nafamostat or pharmaceutically acceptable salt thereof, may include from 1 mg and 500 mg of nafamostat or pharmaceutically acceptable salt thereof, for example, between: 1 and 10 mg, 10 and 20 mg, 20 and 30 mg, 30 and 40 mg, 40 and 50 mg, 50 and 60 mg, 60 and 70 mg, 70 and 80 mg, 80 and 90 mg, 90 and 100 mg, 100 and 110 mg, 110 and 120 mg, 120 and 130 mg, 130 and 140 mg, 140 and 150 mg, 150 and 160 mg, 160 and 170 mg, 170 and 180 mg, 180 and 190 mg, 190 and 200 mg, 200 and 210 mg, 210 and 220 mg, 220 and 230 mg, 230 and 240 mg, 240 and 250 mg, 250 and 260 mg, 260 and 270 mg, 270 and 280 mg, 280 and 290 mg, 290 and 300 mg, 300 and 310 mg, 310 and 320 mg, 320 and 330 mg, 330 and 340 mg, 340 and 350 mg, 350 and 360 mg, 360 and 370 mg, 370 and 380 mg, 380 and 390 mg, 390 and 400 mg, 400 and 410 mg, 410 and 420 mg, 420 and 430 mg, 430 and 440 mg, 440 and 450 mg, 450 and 460 mg, 460 and 470 mg, 470 and 480 mg, 480 and 490 mg and between 490 and 500 mg.

In certain embodiments, the controlled release oral compositions further includes an amount of immediate release nafamostat or pharmaceutically acceptable salt thereof, such as included within a capsule of the controlled release beads. In some instances, the immediate release nafamostat or pharmaceutically acceptable salt thereof is present in the composition (e.g., within the capsule) in form of a powder. In other instances, the immediate release nafamostat or pharmaceutically acceptable salt thereof is present in the composition (e.g., within the capsule) in form of a granulate. The amount of immediate release nafamostat or pharmaceutically acceptable salt thereof present in the oral composition may range from 1 mg to 200 mg, such as from 2 mg to 190 mg, such as from 3 mg to 180 mg, such as from 4 mg to 170 mg, such as from 5 mg to 160 mg, such as from 6 mg to 150 mg, such as from 7 mg to 140 mg, such as from 8 mg to 130 mg, such as from 9 mg to 120 mg and including from 10 mg to 100 mg.

In certain embodiments, controlled-release compositions of nafamostat include those described in U.S. Provisional Patent Application No. 63/158,663, filed Mar. 9, 2021, the disclosure of which is herein incorporated by reference.

Methods for Administering a Methadone Prodrug and an Orally Administered Controlled-Release Composition of Nafamostat or Pharmaceutically Acceptable Salt Thereof Aspects of the present disclosure also include methods for administering to a subject a methadone prodrug and a controlled-release composition of nafamostat or a pharmaceutically acceptable salt thereof.

In practicing the subject methods according to certain embodiments, one or more doses of the methadone prodrugs described herein are orally (including buccally or sublingually) administered with a controlled release nafamostat composition to the subject. The desired protocol used to administer the methadone prodrug and the controlled-release nafamostat composition and the appropriate dosage as described herein may, in certain embodiments, be determined by a qualified healthcare professional (e.g., a physician).

In some instances, the methadone prodrug is administered simultaneously with the controlled release nafamostat composition. Where the methadone prodrug is administered simultaneously with the controlled release nafamostat composition, the methadone prodrug may be administered as a separate composition (e.g., as a pharmaceutical composition that contains the methadone prodrug and one or more pharmaceutically acceptable excipients) or may be co-formulated with the controlled release nafamostat composition. Where the active agent prodrug is co-formulated with the controlled release nafamostat composition, the two components may be combined in a capsule. In some instances, the two components (i.e., methadone prodrug and nafamostat composition) are co-mixed within the capsule. In other instances, the two components are separated within the capsule, such as with a barrier (e.g., a water soluble membrane).

In some cases, the methadone prodrug and the controlled release nafamostat composition are administered sequentially. In some cases, the controlled release nafamostat composition is orally administered to the subject a predetermined period of time before administering the methadone prodrug. For example, the controlled release nafamostat composition may be orally administered to the subject 1 minute or more before administering the methadone prodrug, such as 2 minutes or more, such as 3 minutes or more, such as 4 minutes or more, such as 5 minutes or more, such as 10 minutes or more, such as 15 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 12 hours or more, such as 16 hours or more, such as 20 hours or more and including administering the controlled release nafamostat composition may be orally administered to the subject 24 hours or more before administering the methadone prodrug.

In some cases, the controlled release nafamostat composition is orally administered to the subject a predetermined period of time after administering the methadone prodrug. For example, the controlled release nafamostat composition may be orally administered to the subject 1 minute or more after administering the methadone prodrug, such as 2 minutes or more, such as 3 minutes or more, such as 4 minutes or more, such as 5 minutes or more, such as 10 minutes or more, such as 15 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 12 hours or more, such as 16 hours or more, such as 20 hours or more and including administering the controlled release nafamostat composition may be orally administered to the subject 24 hours or more after administering the methadone prodrug.

The dosage amount of the methadone prodrug administered to the subject may vary, ranging from about 0.1 mg/kg to 200 mg/kg per day, such as from 0.5 mg/kg to 100 mg/kg per day, such as 1.0 mg/kg to 50 mg/kg per day, such as 2 mg/kg to 40 mg/kg per day, such as 5 mg/kg to 30 mg/kg per day, and including 10 mg/kg to 20 mg/kg per day. In embodiments, the methadone prodrug may be administered to the subject once per day, twice per day, three times per day, four times per day, five times per day or at some other interval. In one embodiment the methadone prodrug is administered at a dose such that the level of the active agent achieved in the blood is in the range of from 0.001 ng/ml to 500 ng/ml, such as from 0.005 ng/ml to 450 ng/ml, such as from 0.01 ng/ml to 400 ng/ml, such as from 0.05 ng/ml to 350 ng/ml, such as from 0.1 ng/ml to 300 ng/ml, such as from 0.5 ng/ml to 250 ng/ml, such as from 1 ng/ml to 200 ng/ml, such as from 1.5 ng/ml to 100 ng/ml, such as from 2 ng/ml to 50 ng/ml and including from 3 ng/ml to 25 ng/ml.

Each treatment interval with the methadone prodrug may be 1 day or longer, such as 2 days or longer, such as 3 days or longer, such as 4 days or longer, such as 5 days or longer, such as 6 days or longer, such as 7 days or longer, such as 2 weeks or longer, such as 3 weeks or longer, such as 4 weeks or longer, such as 8 weeks or longer, such as 12 weeks or longer, such as 16 weeks or longer, such as 20 weeks or longer, such as 24 weeks or longer, such as 28 weeks or longer, such as 32 weeks or longer, such as 36 weeks or longer, such as 40 weeks or longer, such as 44 weeks or longer, such as 48 weeks or longer and including 52 weeks or longer. In certain embodiments, protocols may include multiple dosage intervals. In practicing methods of the present disclosure, treatment regimens may include two or more dosage intervals, such as three or more dosage intervals, such as four or more dosage intervals, such as five or more dosage intervals, including ten or more dosage intervals.

In some instances, the methadone prodrug is administered to the subject once or more per day in a cycle for a duration of 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days or 2 days or 1 day. In some instances, the methadone prodrug is administered to the subject once per day for a duration of from about 1 day to about 30 days, such as once per day for a duration of from about 1 day to about 28 days, from 1 day to 21 days, from 7 days to 14 days. In certain instances, the methadone prodrug is administered to the subject once per day for a duration of 14 days. In other instances, the methadone prodrug is administered to the subject twice per day for a duration of from about 1 day to about 30 days, such as once per day for a duration of from about 1 day to about 28 days, from 1 day to 21 days, from 7 days to 14 days. In certain instances, the methadone prodrug is administered to the subject twice per day for a duration of 14 days.

The dosage amount of the controlled release nafamostat composition administered to the subject may vary, ranging from about 0.01 mg/kg to 20 mg/kg per day, such as from 0.05 mg/kg to 19 mg/kg per day, such as 0.1 mg/kg to 18 mg/kg per day, such as 0.5 mg/kg to 17 mg/kg per day, such as 1 mg/kg to 16 mg/kg per day, and including 1 mg/kg to 15 mg/kg per day. In embodiments, the controlled release nafamostat composition may be administered to the subject once per day, twice per day, three times per day, four times per day, five times per day or at some other interval.

Each treatment interval with the controlled release nafamostat composition may be 1 day or longer, such as 2 days or longer, such as 3 days or longer, such as 4 days or longer, such as 5 days or longer, such as 6 days or longer, such as 7 days or longer, such as 2 weeks or longer, such as 3 weeks or longer, such as 4 weeks or longer, such as 8 weeks or longer, such as 12 weeks or longer, such as 16 weeks or longer, such as 20 weeks or longer, such as 24 weeks or longer, such as 28 weeks or longer, such as 32 weeks or longer, such as 36 weeks or longer, such as 40 weeks or longer, such as 44 weeks or longer, such as 48 weeks or longer and including 52 weeks or longer. In certain embodiments, protocols may include multiple dosage intervals. In practicing methods of the present disclosure, treatment regimens may include two or more dosage intervals, such as three or more dosage intervals, such as four or more dosage intervals, such as five or more dosage intervals, including ten or more dosage intervals.

In some instances, the controlled release nafamostat composition is administered to the subject once or more per day in a cycle for a duration of 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days or 2 days or 1 day. In some instances, the controlled release nafamostat composition is administered to the subject once per day for a duration of from about 1 day to about 30 days, such as once per day for a duration of from about 1 day to about 28 days, from 1 day to 21 days, from 7 days to 14 days. In certain instances, the controlled release nafamostat composition is administered to the subject once per day for a duration of 14 days. In other instances, the controlled release nafamostat composition is administered to the subject twice per day for a duration of from about 1 day to about 30 days, such as once per day for a duration of from about 1 day to about 28 days, from 1 day to 21 days, from 7 days to 14 days. In certain instances, the controlled release nafamostat composition is administered to the subject twice per day for a duration of 14 days.

The duration between dosage intervals in a multiple dosage interval treatment protocol may vary, depending on the physiology of the subject or by the treatment protocol as determined by a health care professional. For example, the duration between dosage intervals in a multiple treatment protocol may be predetermined and follow at regular intervals. As such, the time between dosage intervals may vary and may be 1 day or longer, such as 2 days or longer, such as 4 days or longer, such as 6 days or longer, such as 8 days or longer, such as 12 days or longer, such as 16 days or longer and including 24 days or longer. In certain embodiments, multiple dosage interval protocols provide for a time between dosage intervals of 1 week or longer, such as 2 weeks or longer, such as 3 weeks or longer, such as 4 weeks or longer, such as 5 weeks or longer, including 6 weeks or longer.

In some embodiments, dosing is administered in cycles of administration of methadone prodrug and the controlled release nafamostat composition. In some embodiments, the cycle is 21 days or more, in some instances the cycle is 28 days or more. The cycles of drug administration may be repeated for 1, 2, 3, 4, 5, 6, 7, 8 or more than 8 dosage cycles, for a total period of 6 months or 1 year or 2 years or 3 years or 4 years or more. This administration cycle may be repeated, such as 2 or more times, such as 3 or more times, such as 4 or more times, such as 5 or more times, such as 6 or more time, such as 7 or more times, such as 8 or more times, such as 9 or more times and including 10 or more times.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

General Procedure for the In Situ PNP-Activation of Methadone and Coupling to the Amines (G-PNP)

Methadone (1.00 eq.) was dissolved in dry (over mol. sieves) tetrahydrofurane (20 vol.) and cooled down to −78° C. To this solution was added dropwise a solution of potassium bis(trimethylsilyl)amide (0.5M, 1.00 eq.) in toluene (over 5 min.) keeping the temperature below −60° C. The yellowish solution was stirred for 45 min. at −78° C.

A solution of 4-nitrophenyl carbonochloridate (1.03 eq.) in tetrahydrofurane (15 vol.) was cooled to −78° C. The above prepared enolate solution was added dropwise with a cannula, keeping the temperature below −70° C., and the reaction mixture stirred for 120 min at −78° C. A sample in diluted in acetonitrile/water was analyzed by HPLC-MS (mass 474 of the activated methadone).

A solution of (R)—N-(2-(methylamino)ethyl)-5-(3-((2,2,4,6,7-pentamethyl-2,3-dihydrobenzofuran-5-yl)sulfonyl)¬gua¬ni¬dino)-2-propionamidopentanamide (1 eq.) in tetrahydrofurane (10 vol.) was dropwise added and the reaction mixture allowed to warm to room temperature and stirred for 18-60 hours. A sample diluted in acetonitrile/water was analyzed by HPLC-MS (typically 5-20% methadone and 10-50% product visible).

The slurry was poured into a cold mixture of water (50 ml) and dichloromethane (50 ml). The organic layer was collected, washed with NaHCO₃ (aq. sat.), dried over Na2SO4, filtered and concentrated in vacuo to give a yellow solid, which was analyzed by HPLC-MS (typically containing 5-25% methadone and 10-45% of the product).

The crude material was purified by automated silica gel column chromatography with dichloromethane/methanol gradient from 3 to 25% (crude compound dissolved in DCM). The product was the last and broadest eluting peak, with some methadone tailing into the product peak. The appropriate fractions were evaporated and dried in vacuo to afford a mixture of compounds, that had to be purified again by RP-prep. HPLC for all branched aliphatic tethered prodrugs.

Synthesis of Intermediate for Methadone Pro-Drug

Figure 2:
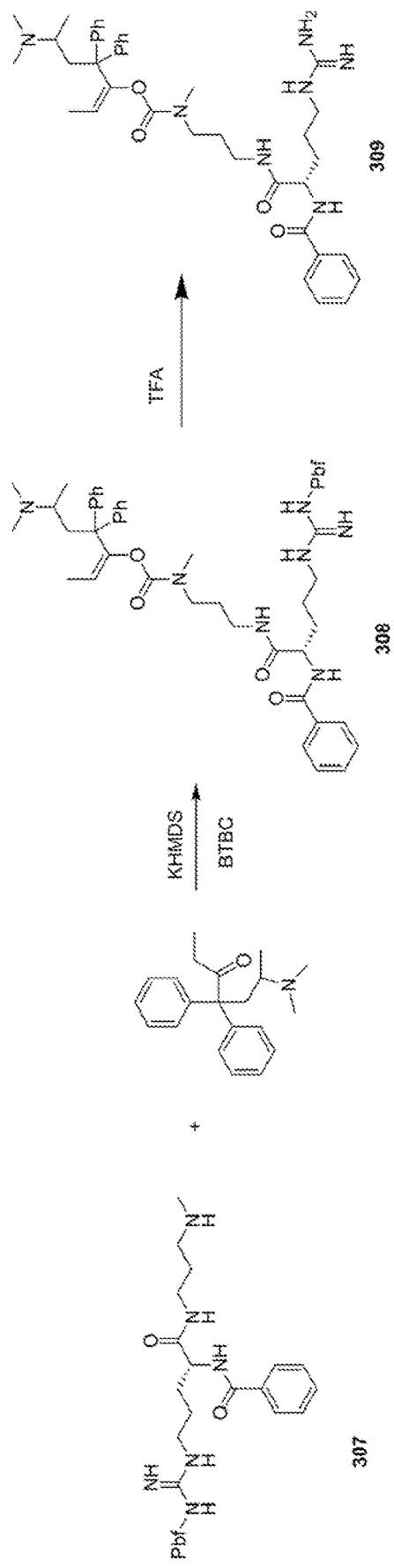
FIG. 2 depicts an example synthetic scheme of an intermediate for methadone prodrug according to certain embodiments.

FIG. 1 depicts an example synthetic scheme of an intermediate for methadone prodrug according to certain embodiments. FIG. 2 depicts an example synthetic scheme of an intermediate for methadone prodrug according to certain embodiments.

Synthesis of N-methyl-ethane-tether Methadone Pro-Drug

Figure 3:
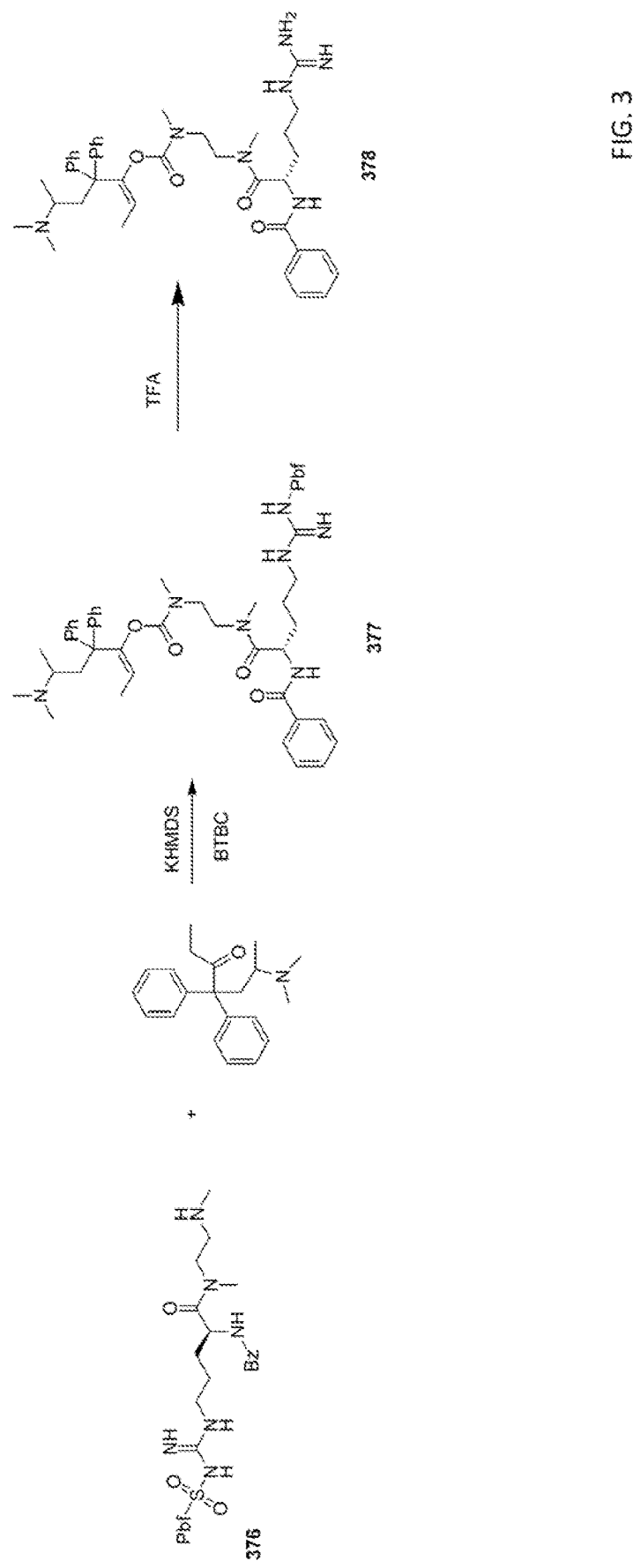
FIG. 3 depicts an example synthetic scheme of an N-methyl-ethane-tether methadone prodrug according to certain embodiments.

FIG. 3 depicts an example synthetic scheme of an N-methyl-ethane-tether methadone prodrug according to certain embodiments.

Synthesis of 2-methylethane-tether Intermediate for Methadone Pro-Drug

Figure 4:
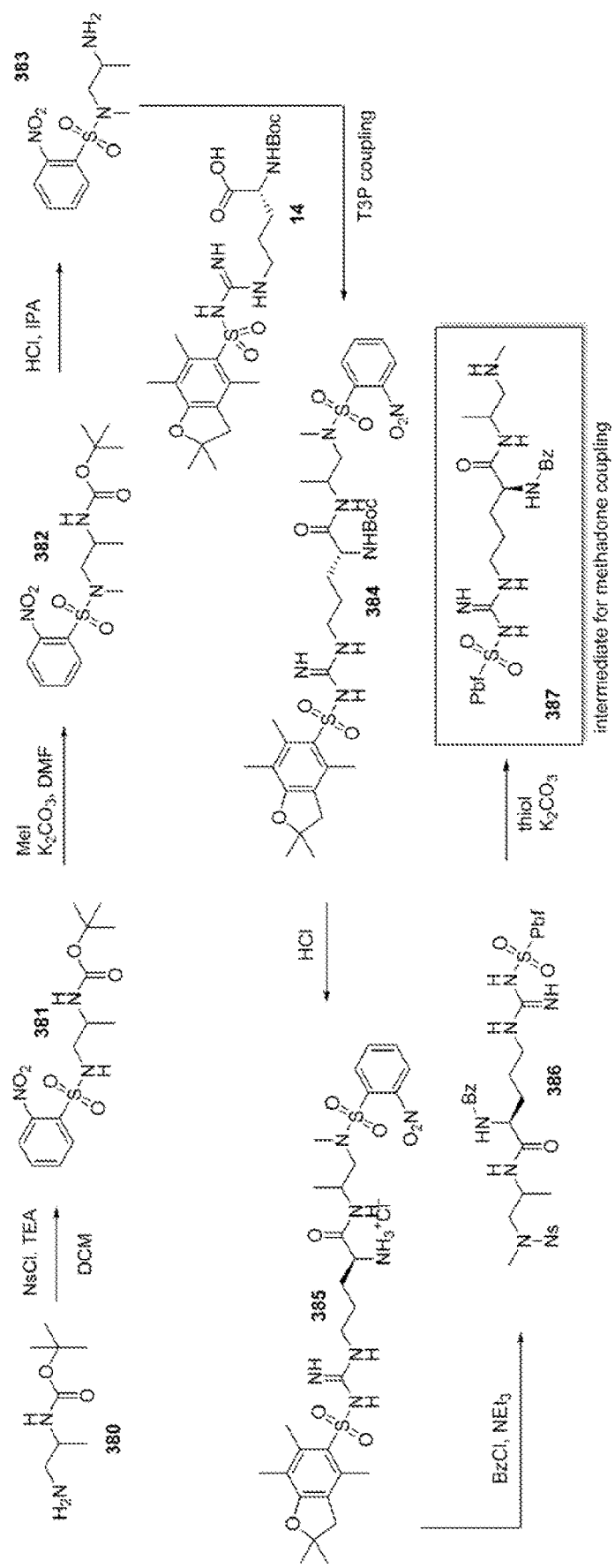
FIG. 4 depicts an example synthetic scheme of a 2-methylethane-tether intermediate for a methadone prodrug according to certain embodiments.

FIG. 4 depicts an example synthetic scheme of a 2-methylethane-tether intermediate for a methadone prodrug according to certain embodiments.

Synthesis of 1,3-homologuous N-methyl-pyrrolidine Tether Methadone Pro-Drug

Figure 5:
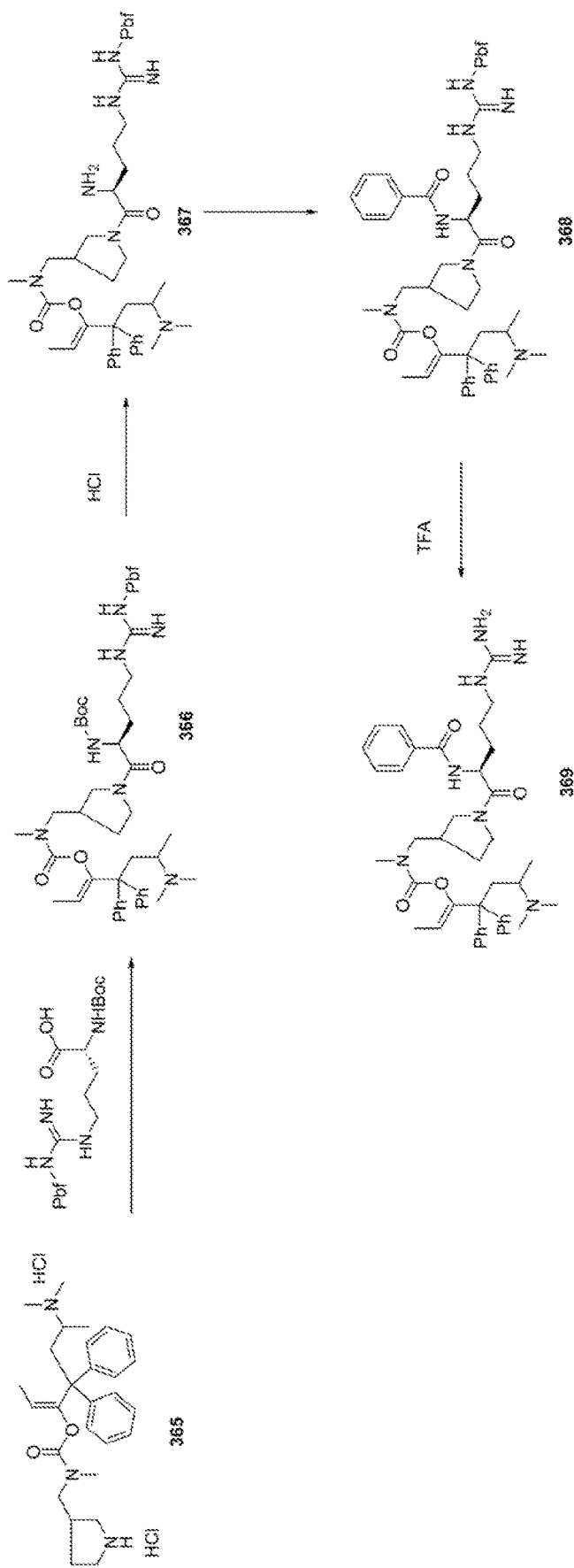
FIG. 5 depicts an example synthetic scheme of a 1,3-homologuous N-methyl-pyrrolidine tether methadone prodrug according to certain embodiments.

FIG. 5 depicts an example synthetic scheme of a 1,3-homologuous N-methyl-pyrrolidine tether methadone prodrug according to certain embodiments.

General Procedure for the Global TFA Deprotection to the Final Prodrugs (G-TFA)

To the protected pro-drug (1 eq.) in dichloromethane (20 vol.) was added a drop water and trifluoroacetic acid (115 eq.). The solution was stirred over night and a sample taken and diluted in acetonitrile for HPLC-MS analysis (full conversion). The reaction mixture was concentrated at the rotary evaporator to afford a heavy oil. This heavy oil was dropwise added to tert-butyl methyl ether (120 vol.). After sonication and cooling to 5° C. a white solid was collected by filtration and washed with tert-butyl methyl ether (60 vol.). Drying in vacuo gave the final pro-drug as bis TFA salt.

Pbf Protected 1-Methylethane N-Benzoylarginine Methadone Prodrug

Following general procedure G-PNP methadone (1.22 g, 3.05 mmol) was reacted with N-((2R)-1-((2-(methylamino)propyl)amino)-1-oxo-5-(3-((2,2,4,6,7-pentamethyl-2,3-dihydrobenzofuran-5-yl)sulfonyl)guanidino)pentan-2-yl)benzamide (2.50 g, 3.95 mmol). After work-up and isolation by normal and then RP-phase column chromatography 6-(dimethylamino)-4,4-diphenylhept-2-en-3-yl (1-((S)-2-benzamido-5-(3-((2,2,4,6,7-pentamethyl-2,3-dihydrobenzofuran-5-yl)sulfonyl)guanidino)pentanamido)propan-2-yl)(methyl)carbamate (235 mg, 6.35% yield) was isolated in 93.9% purity (HPLC-MS).

1-Methylethane N-benzoylarginine Methadone Prodrug

Following general procedure G-TFA 6-(dimethylamino)-4,4-diphenylhept-2-en-3-yl (1-((S)-2-benzamido-5-(3-((2,2,4,6,7-pentamethyl-2,3-dihydrobenzofuran-5-yl)sulfonyl)guanidino)pentanamido)propan-2-yl)(methyl)carbamate (303 mg, 0.236 mmol) was deprotected to give 6-(dimethylamino)-4,4-diphenylhept-2-en-3-yl (1-((S)-2-benzamido-5-guanidinopentanamido)propan-2-yl)(methyl)carbamate (173 mg, 92.2%), which was isolated by trituration in 92.2% purity (HPLC-MS) as a bis TFA salt. The HPLC-MS spectrum shows a peak splitting for the E- and Z-isomers.

Pbf Protected 2-Methylethane N-benzoylarginine Methadone Prodrug

Following general procedure G-PNP methadone (417 mg, 1.34 mmol) was reacted with N-((2R)-1-((1-(methylamino)propan-2-yl)amino)-1-oxo-5-(3-((2,2,4,6,7-pentamethyl-2,3-dihydrobenzofuran yl)sulfonyl)guanidino)pentan-2-yl)benzamide (850 mg, 1.34 mmol). After work-up and isolation by normal and then RP-phase column chromatography 6-(dimethylamino)-4,4-diphenylhept-2-en-3-yl (2-((S)-2-benzamido-5-(3-((2,2,4,6,7-pentamethyl-2,3-dihydrobenzofuran yl)sulfonyl)guanidino)pentanamido)propyl)(methyl)carbamate (240 mg, 12% yield) was isolated in 62% purity (HPLC-MS).

2-Methylethane N-benzoylarginine Methadone prodrug

Following general procedure G-TFA 6-(dimethylamino)-4,4-diphenylhept-2-en-3-yl (2-((S)-2-benzamido-5-(3-((2,2,4,6,7-pentamethyl-2,3-dihydrobenzofuran-5-yl)sulfonyl)guanidino)pentanamido)propyl)(methyl)carbamate (220 mg, 0.235 mmol) was deprotected to give 6-(dimethylamino)-4,4-diphenylhept-2-en-3-yl (2-((S)-2-benzamido-5-guanidinopentanamido)propyl)(methyl)carbamate (144 mg, 73.3% yield), which was isolated by trituration in 92.2% purity (HPLC-MS) as a bis TFA salt. The HPLC-MS spectrum shows no peak splitting for the E- and Z-isomers.

Pbf Protected 2-Ethylethane N-benzoylarginine Methadone Prodrug

Following general procedure G-PNP methadone (400 mg, 1.29 mmol) was reacted with N-((2R)-1-((1-(methylamino)butan-2-yl)amino)-1-oxo-5-(3-((2,2,4,6,7-pentamethyl-2,3-dihydrobenzofuran-5-yl)sulfonyl)guanidino)pentan-2-yl)benzamide (837 mg, 1.29 mmol). After work-up and isolation by normal and then RP-phase column chromatography 6-(dimethylamino)-4,4-diphenylhept-2-en-3-yl (2-((S)-2-benzamido-5-(3-((2,2,4,6,7-pentamethyl-2,3-dihydrobenzofuran-5-yl)sulfonyl)guanidino)pentanamido)butyl)(methyl)carbamate (107 mg, 8.7% yield) was isolated in 99.8% purity (HPLC-MS).

2-Ethylethane N-benzoylarginine Methadone Prodrug

Following general procedure G-TFA 6-(dimethylamino)-4,4-diphenylhept-2-en-3-yl (2-((S)-2-benzamido-5-(3-((2,2,4,6,7-pentamethyl-2,3-dihydrobenzofuran-5-yl)sulfonyl)guanidino)pentanamido)butyl)(methyl)carbamate (107 mg, 0.113 mmol) was deprotected to give 6-(dimethylamino)-4,4-diphenylhept-2-en-3-yl (2-((S)-2-benzamido-5-guanidinopentanamido)butyl)(methyl)carbamate (106 mg, 57.0% yield), which was isolated by trituration in 93.0% purity (HPLC-MS) as a bis TFA salt. The HPLC-MS spectrum shows significant peak splitting for the E- and Z-isomers.

Digestion with Trypsin

Figure 6:
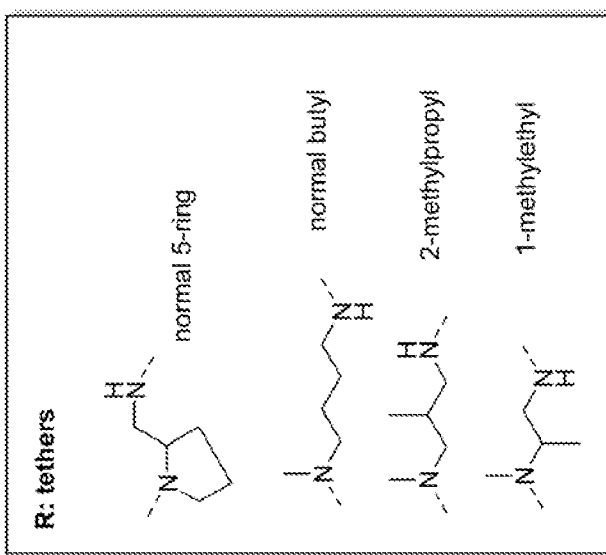
FIG. 6 depicts an example of trypsin digestion of methadone prodrugs according to certain embodiments.
Figure 6:
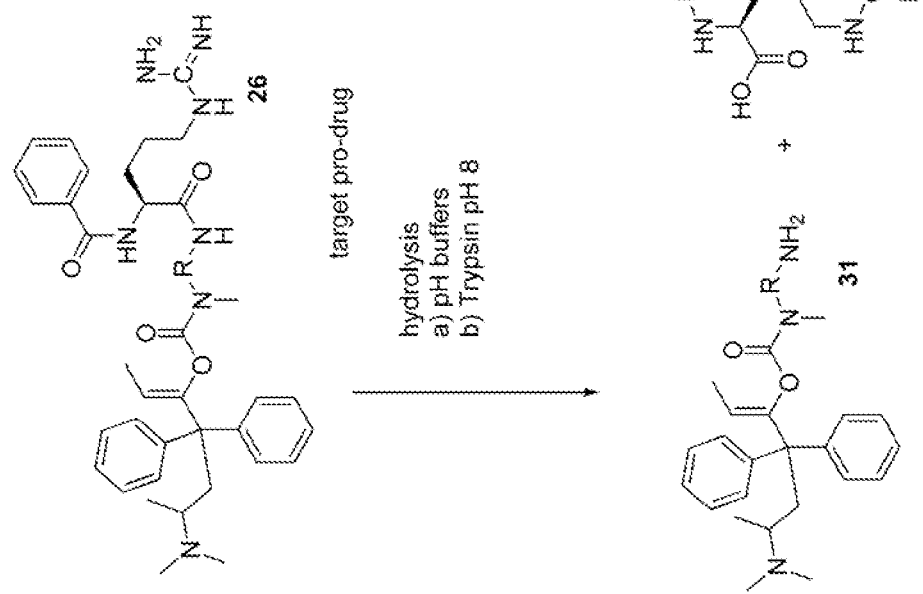
Figure 7A:
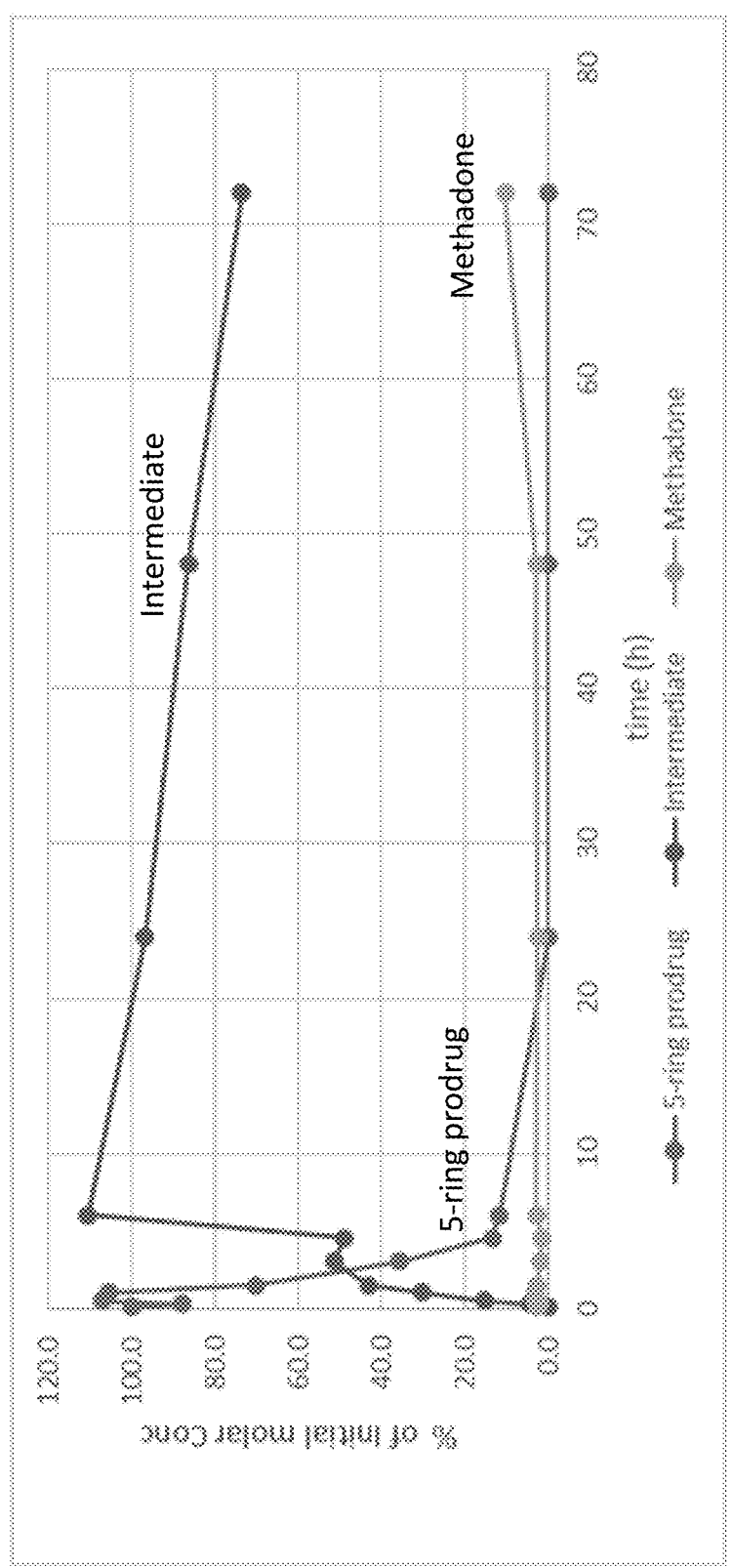
FIGS. 7A-7D depicts methadone release from methadone prodrugs according to certain embodiments.
Figure 7B:
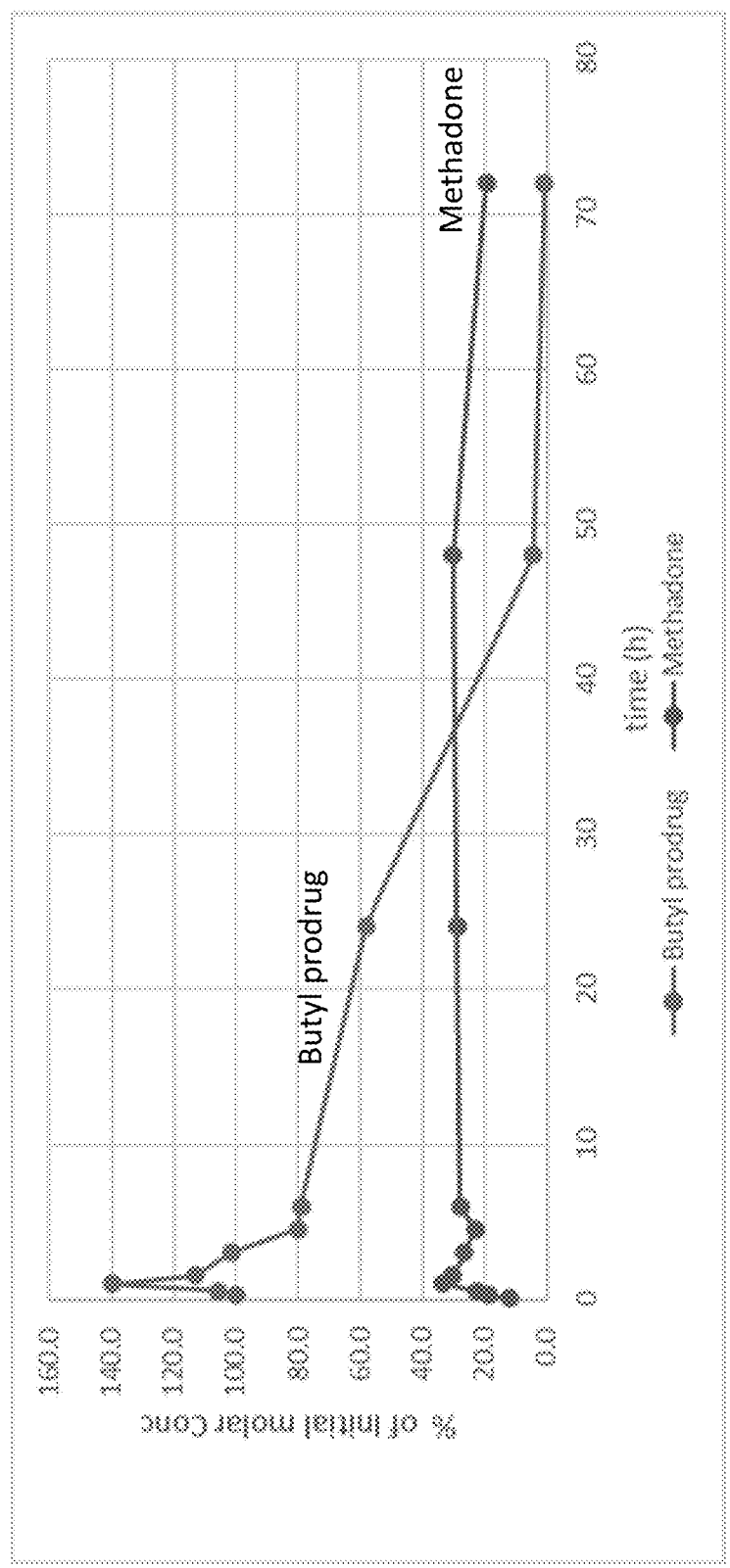
Figure 7C:
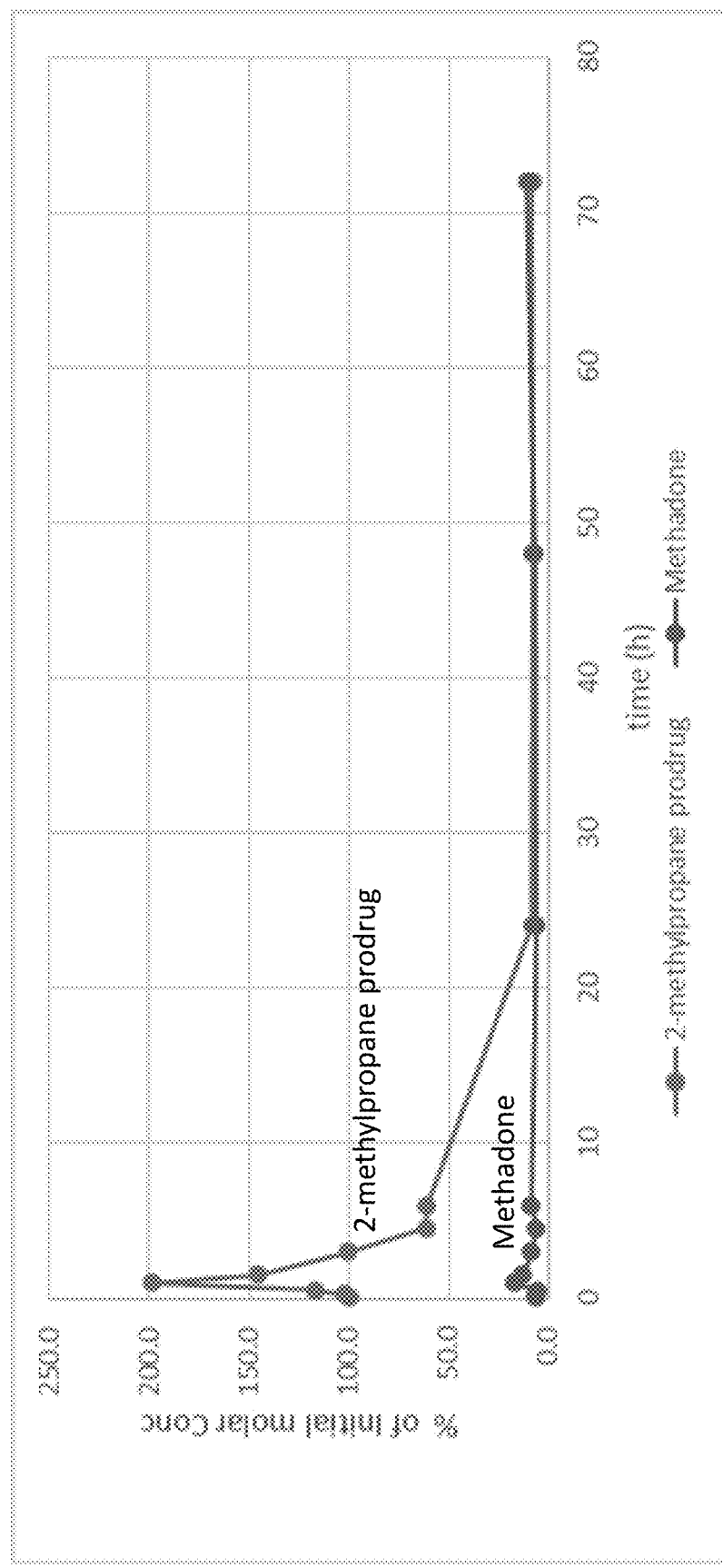
Figure 7D:
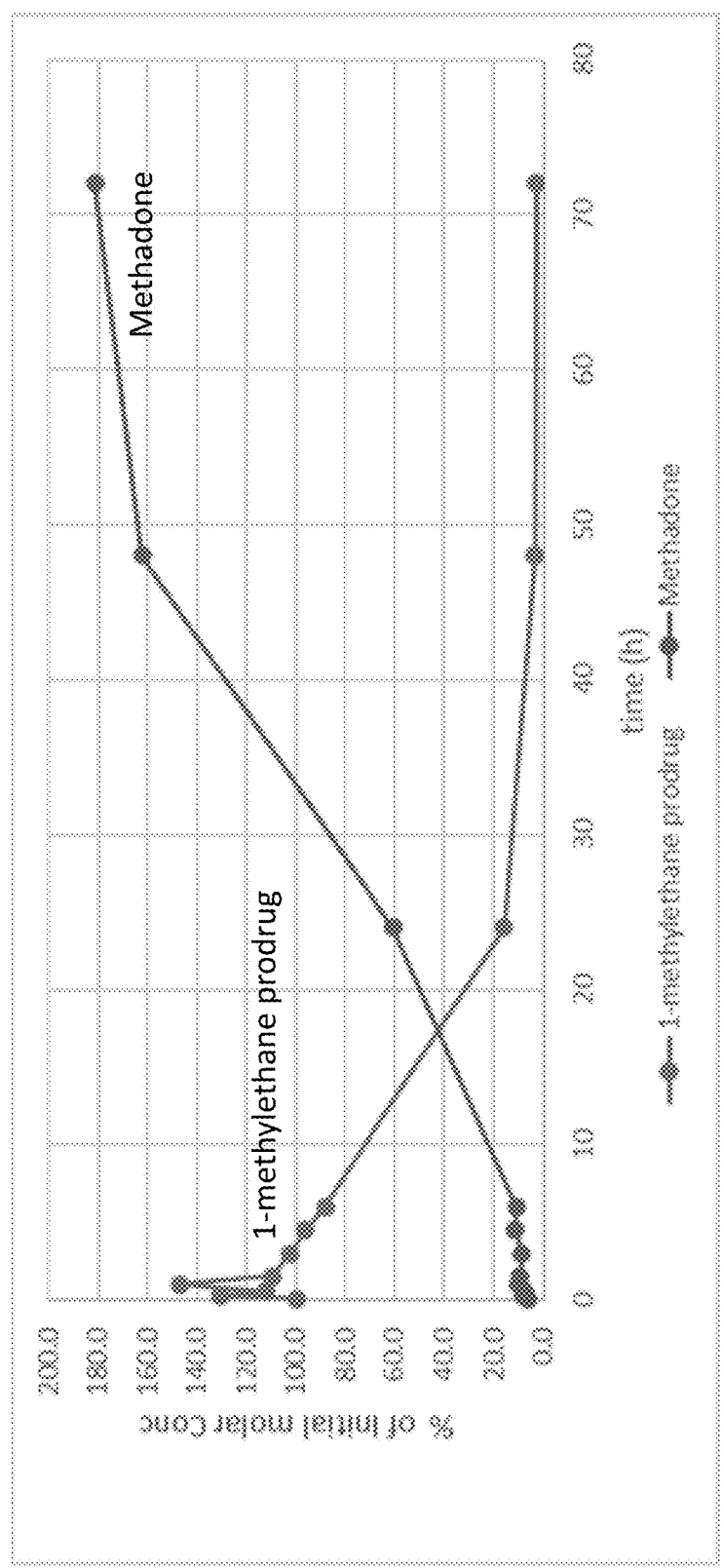

FIG. 6 depicts an example of trypsin digestion of methadone prodrugs according to certain embodiments. All prodrugs are digested fully within 8-24 h. The pro-drug with 1-methylethyl linker is slightly slower, requiring 24-48 h. Only the pro-drug with the 1-methylethyl linker shows rapid release to methadone, in all other pro-drugs the release intermediate seems stable, with the 5-ring release intermediate showing a very slow release, which was not seen during the stability testing of this release intermediate. FIGS. 7A-7D depicts methadone release from methadone prodrugs as shown in FIG. 6.

Synthesis of Levomethadone Precursor with Butane Tether

Figure 8:
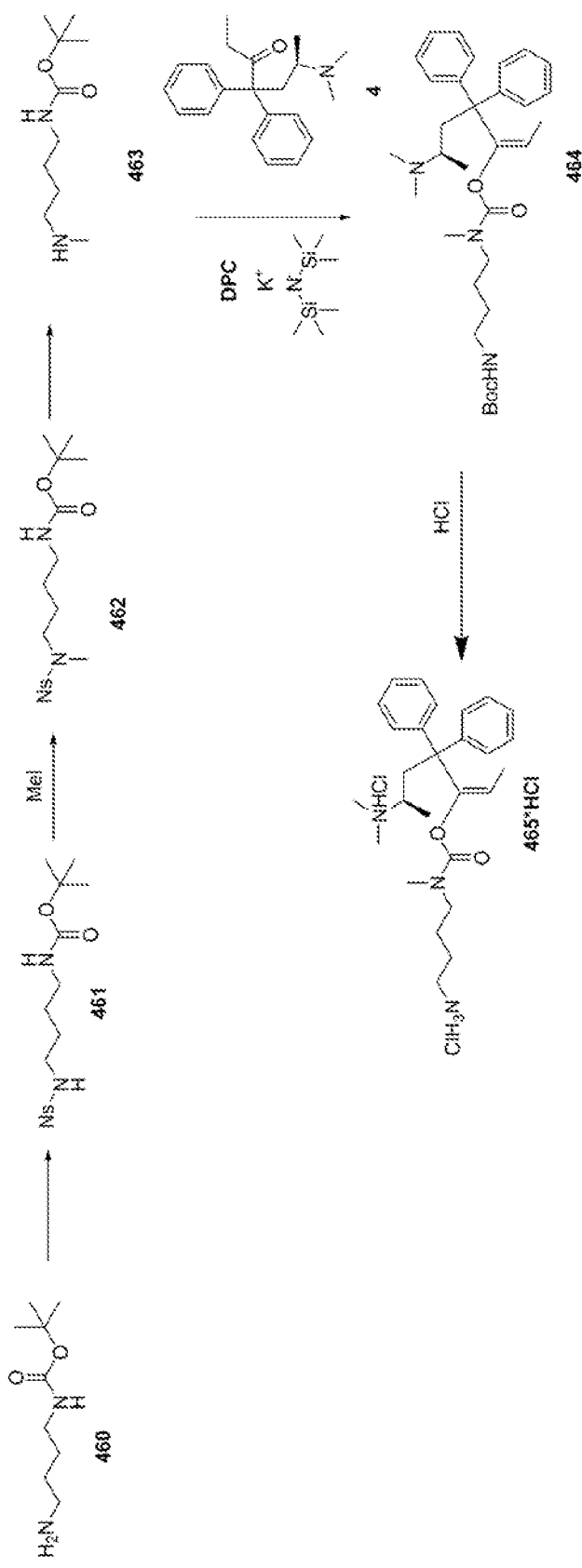
FIG. 8 depicts an example scheme for the synthesis of levomethadone precursor with butane tether according to certain embodiments.
Figure 9:
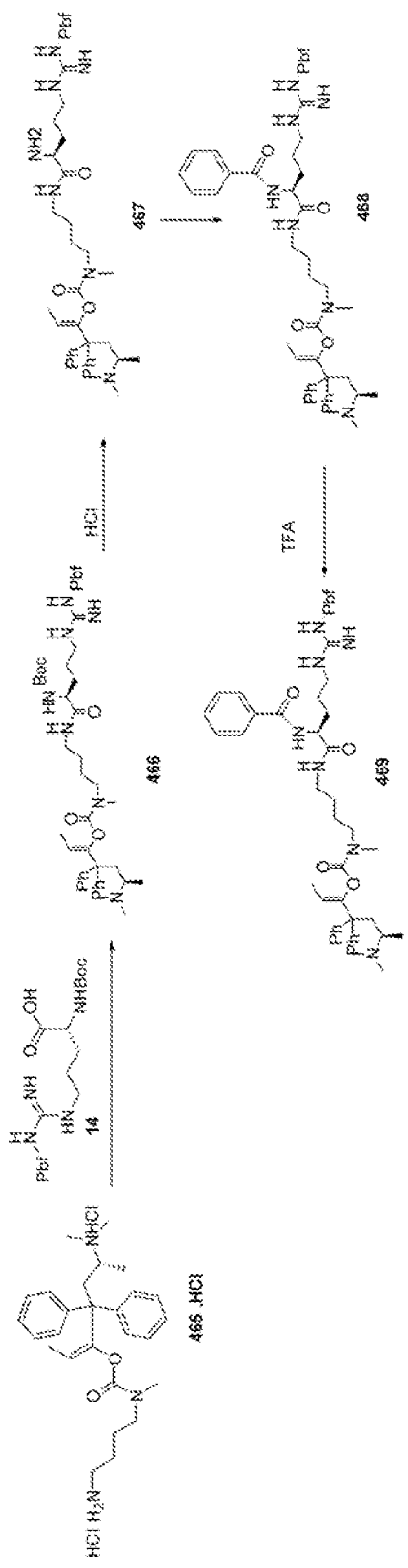
FIG. 9 depicts an example scheme for the synthesis of levomethadone BU according to certain embodiments.

FIG. 8 depicts an example scheme for the synthesis of levomethadone precursor with butane tether according to certain embodiments. DPC coupling was performed with 2.29 g of levomethadone. 5.70 g of crude material was isolated. Purification was conducted by automated column chromatography. About 1.9 g of compound 464 was isolated (HPLC purity 78%). After boc-protections, an amount 2.1 g (quant) of the HCl salt of 465 was obtained. Compound 465 was used for T3P coupling with protected Arg as shown in FIG. 9. T3P coupling to 466 was conducted. The conversion was about 85% with a crude yield of 466 of about 2.5 g. 1.67 g (58%) of compound 466 was isolated upon trituration with TBME and diethyl ether. The purity of 3 different batches was about 84-92% with about 0.85 g, 0.45 g and 0.38 g isolated. Compound 466 was boc-protected with HCl in isopropyl alcohol. The crude primary amine 467 was benzoyl protected. Purification was conducted by chromatography. About 750 mg of compound 468 was isolated.

Synthesis of Levomethadone Precursor with R 2-MeEt Tether

Figure 10:
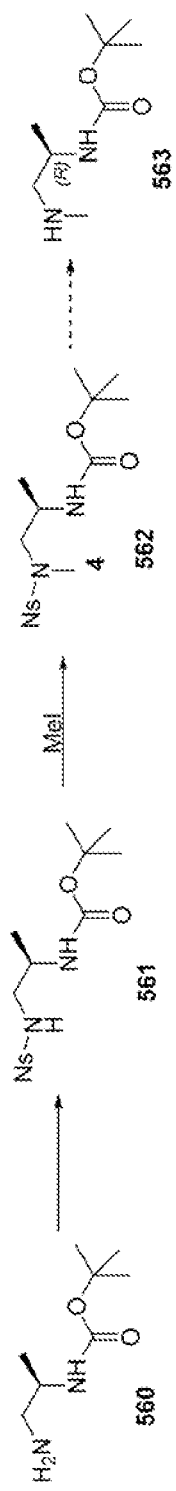
FIG. 10 depicts an example scheme for the synthesis of levomethadone precursor with R 2-MeEt tether according to certain embodiments.

FIG. 10 depicts an example scheme for the synthesis of levomethadone precursor with R 2-MeEt tether according to certain embodiments. 4.8 g of tert-butyl (R)-(1-aminopropan-2-yl)carbamate 560 was nosyl-protected. The yield was 8 g (82%) of compound 561. N-methylation was performed and compound 562 was isolated in quantitative yield with a purity of 95% as determined by liquid chromatography. The crude produce was used for nosyl protection. After 2 days at 45° C., the reaction was complete.

Synthesis of Levomethadone Precursor with S 2-MeEt Tether

Figure 11:
FIG. 11 depicts an example scheme for the synthesis of levomethadone precursor with S 2-MeEt tether according to certain embodiments.

FIG. 11 depicts an example scheme for the synthesis of levomethadone precursor with S 2-MeEt tether according to certain embodiments. 4.8 g of compound 660 was nosyl-protected.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. Compound MD-112, shown below:

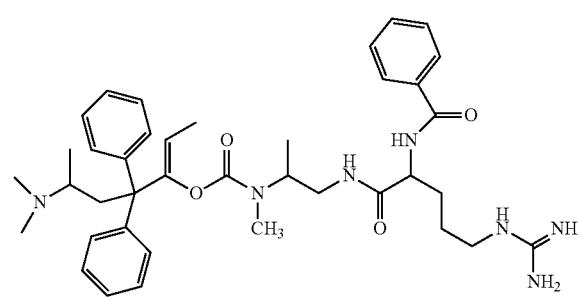

Compound MD-112 or a salt, hydrate or solvate thereof.

2. A composition comprising:
Compound MD-112:
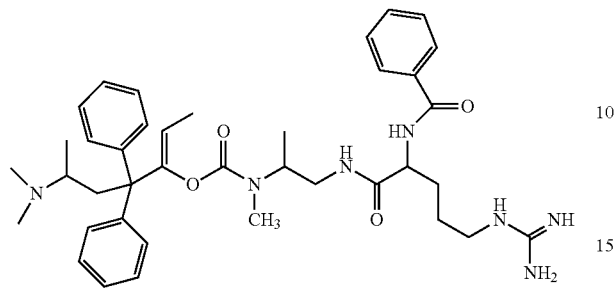
or a salt, hydrate or solvate thereof; and
a GI enzyme inhibitor.
3. A method comprising administering to a subject the composition of claim 2.
* * * * *